(12) United States Patent
Bosanac et al.

(10) Patent No.: US 10,624,882 B2
(45) Date of Patent: *Apr. 21, 2020

(54) RHO KINASE INHIBITORS

(71) Applicant: Aerie Pharmaceuticals, Inc., Irvine, CA (US)

(72) Inventors: Todd Bosanac, New Milford, CT (US); John David Ginn, New Milford, CT (US); Eugene Richard Hickey, Ridgefield, CT (US); Thomas Martin Kirrane, Jr., Middlebury, CT (US); Weimin Liu, Sandy Hook, CT (US); Anthony S. Prokopowicz, Stormville, NY (US); Sabine K. Schlyer, New Milford, CT (US); Cheng-Kon Shih, Danbury, CT (US); Roger John Snow, Danbury, CT (US); Michael Robert Turner, Danbury, CT (US); Frank Wu, Ridgefield, CT (US); Erick Richard Young, Danbury, CT (US)

(73) Assignee: Aerie Pharmaceuticals, Inc., Bedminster, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/858,995

(22) Filed: Dec. 29, 2017

(65) Prior Publication Data

US 2018/0344723 A1    Dec. 6, 2018

Related U.S. Application Data

(60) Continuation of application No. 15/142,448, filed on Apr. 29, 2016, now abandoned, which is a continuation of application No. 14/754,787, filed on Jun. 30, 2015, now abandoned, which is a continuation of application No. 14/461,597, filed on Aug. 18, 2014, now abandoned, which is a division of application No. 11/856,740, filed on Sep. 18, 2007, now Pat. No. 8,809,326.

(60) Provisional application No. 60/864,484, filed on Nov. 6, 2006, provisional application No. 60/826,284, filed on Sep. 20, 2006.

(51) Int. Cl.

| | |
|---|---|
| *C07D 487/08* | (2006.01) |
| *A61K 31/472* | (2006.01) |
| *A61K 31/517* | (2006.01) |
| *C07D 239/88* | (2006.01) |
| *C07D 239/90* | (2006.01) |
| *C07D 401/14* | (2006.01) |
| *C07D 403/12* | (2006.01) |
| *C07D 405/12* | (2006.01) |
| *C07D 409/12* | (2006.01) |
| *C07D 413/12* | (2006.01) |
| *A61P 9/00* | (2006.01) |
| *A61P 27/06* | (2006.01) |
| *C07D 217/24* | (2006.01) |
| *C07D 401/12* | (2006.01) |
| *A61K 31/4725* | (2006.01) |
| *A61K 31/496* | (2006.01) |
| *A61K 31/5377* | (2006.01) |
| *A61K 31/541* | (2006.01) |

(52) U.S. Cl.
CPC ........ *A61K 31/472* (2013.01); *A61K 31/4725* (2013.01); *A61K 31/496* (2013.01); *A61K 31/517* (2013.01); *A61K 31/5377* (2013.01); *A61K 31/541* (2013.01); *A61P 9/00* (2018.01); *A61P 27/06* (2018.01); *C07D 217/24* (2013.01); *C07D 239/88* (2013.01); *C07D 239/90* (2013.01); *C07D 401/12* (2013.01); *C07D 401/14* (2013.01); *C07D 403/12* (2013.01); *C07D 405/12* (2013.01); *C07D 409/12* (2013.01); *C07D 413/12* (2013.01); *C07D 487/08* (2013.01)

(58) Field of Classification Search
CPC .................................................. C07D 487/08
See application file for complete search history.

(56) References Cited

U.S. PATENT DOCUMENTS

| | | | |
|---|---|---|---|
| 4,146,637 A | 3/1979 | Metz et al. | |
| 4,337,256 A | 6/1982 | Yasushi et al. | |
| 4,456,757 A | 6/1984 | Hidaka et al. | |
| 4,709,032 A | 11/1987 | Hidaka et al. | |
| 4,911,928 A | 3/1990 | Wallach | |
| 4,954,512 A | 9/1990 | Oguro et al. | |
| 5,508,288 A | 4/1996 | Forbes et al. | |
| 5,519,036 A | 5/1996 | Himmelsbach et al. | |
| 5,798,380 A | 8/1998 | Kaufman et al. | |
| 5,891,646 A | 4/1999 | Barak et al. | |
| 6,110,693 A | 8/2000 | Barak et al. | |
| 6,110,912 A | 8/2000 | Kaufman et al. | |
| 6,362,177 B1 | 3/2002 | Shiota et al. | |
| 6,586,425 B2 | 7/2003 | Kaufman et al. | |

(Continued)

FOREIGN PATENT DOCUMENTS

| | | |
|---|---|---|
| EP | 0109023 | 5/1984 |
| EP | 0232569 | 8/1987 |

(Continued)

OTHER PUBLICATIONS

Wermuth, Camille G. "Molecular Variation Based on Isosteric Replacements" in Chapter 13, The Practice of Medicinal Chemistry, Academic: 1996, pp. 203-237.*

(Continued)

*Primary Examiner* — David K O'Dell
(74) *Attorney, Agent, or Firm* — K&L Gates LLP; Louis C. Cullman; Benjamin D. Heuberger

(57) ABSTRACT

Disclosed are novel substituted 2H-isoquinolin-1-one and 3H-quinazolin-4-one derivatives useful as inhibitors of Rho kinase and for treating a variety of diseases and disorders that are mediated or sustained through the activity of Rho kinase, including cardiovascular diseases, pharmaceutical compositions comprising such compounds, methods for using such compounds and processes for making such compounds.

19 Claims, No Drawings

(56) References Cited

U.S. PATENT DOCUMENTS

| | | |
|---|---|---|
| 6,699,891 B1 | 3/2004 | Kawanishi et al. |
| 6,787,534 B2 | 9/2004 | Haneda |
| 7,268,143 B2 | 9/2007 | Jagtap et al. |
| 7,329,684 B2 | 2/2008 | Mjalli et al. |
| 7,345,158 B2 | 3/2008 | Egashira et al. |
| 7,361,678 B2 | 4/2008 | Mjalli |
| 7,374,891 B2 | 5/2008 | Shahbaz |
| 7,378,498 B2 | 5/2008 | Worley et al. |
| 7,470,787 B2 | 12/2008 | deLong et al. |
| 7,671,205 B2 | 3/2010 | deLong et al. |
| 8,034,943 B2 | 10/2011 | deLong et al. |
| 8,129,411 B2 | 3/2012 | Ehara et al. |
| 8,357,699 B2 | 1/2013 | deLong et al. |
| 8,394,826 B2 | 3/2013 | deLong et al. |
| 8,450,344 B2 | 5/2013 | deLong et al. |
| 8,455,513 B2 | 6/2013 | deLong et al. |
| 8,455,514 B2 | 6/2013 | deLong et al. |
| 8,455,647 B2 | 6/2013 | deLong et al. |
| 8,716,310 B2 | 5/2014 | deLong et al. |
| 8,759,388 B2 | 7/2014 | deLong et al. |
| 8,809,326 B2 | 8/2014 | Bosanac et al. |
| 8,871,757 B2 | 10/2014 | deLong et al. |
| 8,921,392 B2 | 12/2014 | deLong et al. |
| 9,096,569 B2 | 8/2015 | deLong et al. |
| 9,643,927 B1 | 5/2017 | Sturdivant et al. |
| 9,849,122 B2 | 12/2017 | Kopczynski et al. |
| 2004/0091946 A1 | 5/2004 | Oakley et al. |
| 2004/0176462 A1 | 9/2004 | Kawanishi et al. |
| 2005/0032125 A1 | 2/2005 | Oakley et al. |
| 2005/0176712 A1 | 8/2005 | Wakabayashi et al. |
| 2005/0245509 A1 | 11/2005 | Nakajima et al. |
| 2005/0282805 A1 | 12/2005 | Hangeland et al. |
| 2006/0270670 A1 | 11/2006 | Chew et al. |
| 2007/0111983 A1 | 5/2007 | Fong |
| 2007/0123561 A1 | 5/2007 | Lee et al. |
| 2007/0129404 A1 | 6/2007 | Hagihara et al. |
| 2007/0135499 A1 | 6/2007 | deLong et al. |
| 2007/0149473 A1 | 6/2007 | Chatterton et al. |
| 2007/0149548 A1 | 6/2007 | Hellberg et al. |
| 2007/0167444 A1 | 7/2007 | Kuramochi et al. |
| 2007/0238741 A1 | 10/2007 | Nagarathnam et al. |
| 2008/0021026 A1 | 1/2008 | Kahraman et al. |
| 2008/0021217 A1 | 1/2008 | Borchardt |
| 2008/0058384 A1 | 3/2008 | Lee et al. |
| 2008/0096238 A1 | 4/2008 | Sharif et al. |
| 2008/0125427 A1 | 5/2008 | Sehon et al. |
| 2008/0139595 A1 | 6/2008 | Schirok et al. |
| 2008/0153799 A1 | 6/2008 | Laurent et al. |
| 2008/0153813 A1 | 6/2008 | Chen et al. |
| 2008/0194584 A1 | 8/2008 | Birault et al. |
| 2008/0275029 A1 | 11/2008 | Berdini et al. |
| 2009/0005321 A1 | 1/2009 | Zimmer et al. |
| 2009/0069371 A1 | 3/2009 | deLong et al. |
| 2009/0186917 A1 | 7/2009 | deLong et al. |
| 2010/0093790 A1 | 4/2010 | deLong et al. |
| 2010/0105650 A1 | 4/2010 | Plettenburg et al. |
| 2010/0144713 A1 | 6/2010 | deLong et al. |
| 2010/0280011 A1 | 11/2010 | deLong et al. |
| 2011/0015204 A1 | 1/2011 | Bencsik et al. |
| 2012/0135984 A1 | 5/2012 | deLong et al. |
| 2012/0196916 A1 | 8/2012 | deLong et al. |
| 2013/0137721 A1 | 5/2013 | deLong et al. |
| 2014/0187617 A1 | 7/2014 | deLong et al. |
| 2014/0275160 A1 | 9/2014 | Kopczynski |
| 2014/0275161 A1 | 9/2014 | Kopczynski |
| 2014/0288056 A1 | 9/2014 | Cui et al. |
| 2014/0357652 A1 | 12/2014 | Bosanac et al. |
| 2015/0119419 A1 | 4/2015 | deLong et al. |
| 2015/0175549 A1 | 6/2015 | deLong et al. |
| 2015/0297581 A1 | 10/2015 | Bosanac et al. |
| 2015/0299159 A1 | 10/2015 | deLong et al. |
| 2016/0016951 A1 | 1/2016 | Schiemann et al. |
| 2016/0243102 A1 | 8/2016 | Bosanac et al. |
| 2016/0272589 A1 | 9/2016 | deLong et al. |
| 2016/0280656 A1 | 9/2016 | deLong et al. |
| 2018/0370919 A1 | 12/2018 | Sturdivant et al. |

FOREIGN PATENT DOCUMENTS

| | | |
|---|---|---|
| EP | 0389995 | 10/1990 |
| EP | 0482939 | 4/1992 |
| EP | 1541151 | 6/2005 |
| EP | 1550660 | 7/2005 |
| JP | 2005227441 | 8/2005 |
| JP | 2007236388 | 9/2007 |
| JP | 2007246466 | 9/2007 |
| WO | 1993/018028 | 9/1993 |
| WO | 2000/076970 | 12/2000 |
| WO | 2001/037826 | 5/2001 |
| WO | 2001/047891 | 7/2001 |
| WO | 2001/053268 | 7/2001 |
| WO | 2001/053274 | 7/2001 |
| WO | 2001/056607 | 8/2001 |
| WO | 2002/022576 | 3/2002 |
| WO | 2002/032864 | 4/2002 |
| WO | 2002/085857 | 10/2002 |
| WO | 2002/085859 | 10/2002 |
| WO | 2003/064397 | 8/2003 |
| WO | 2003/073999 | 9/2003 |
| WO | 2003/080578 | 10/2003 |
| WO | 2004/029045 | 4/2004 |
| WO | 2004/078747 | 9/2004 |
| WO | 2005/020921 | 3/2005 |
| WO | 2005/035503 | 4/2005 |
| WO | 2005/037257 | 4/2005 |
| WO | 2006/041119 | 4/2006 |
| WO | 2006/051290 | 5/2006 |
| WO | 2006/062982 | 6/2006 |
| WO | 2006/076706 | 7/2006 |
| WO | 2007/008926 | 1/2007 |
| WO | 2007/008942 | 1/2007 |
| WO | 2007/060028 | 5/2007 |
| WO | 2007/065916 | 6/2007 |
| WO | 2007/076360 | 7/2007 |
| WO | 2007/076367 | 7/2007 |
| WO | 2007/100880 | 9/2007 |
| WO | 2007/142323 | 12/2007 |
| WO | 2008/011557 | 1/2008 |
| WO | 2008/011560 | 1/2008 |
| WO | 2008/016016 | 2/2008 |
| WO | 2008/036459 | 3/2008 |
| WO | 2008/036540 | 3/2008 |
| WO | 2008/049000 | 4/2008 |
| WO | 2008/049919 | 5/2008 |
| WO | 2008/054599 | 5/2008 |
| WO | 2008/077057 | 6/2008 |
| WO | 2008/077550 | 7/2008 |
| WO | 2008/077551 | 7/2008 |
| WO | 2008/077552 | 7/2008 |
| WO | 2008/077553 | 7/2008 |
| WO | 2008/077554 | 7/2008 |
| WO | 2008/077555 | 7/2008 |
| WO | 2008/077556 | 7/2008 |
| WO | 2008/079880 | 7/2008 |
| WO | 2008/079945 | 7/2008 |
| WO | 2008/086269 | 7/2008 |
| WO | 2008/124665 | 10/2008 |
| WO | 2009/091898 | 7/2009 |
| WO | 2010/011853 | 1/2010 |
| WO | 2010/126626 | 11/2010 |
| WO | 2010/127329 | 11/2010 |
| WO | 2010/127330 | 11/2010 |
| WO | 2012/105674 | 8/2012 |
| WO | 2014/144781 A1 | 9/2014 |
| WO | 2017/086941 A1 | 5/2017 |

OTHER PUBLICATIONS

Japanese Patent Office Action for Application No. 2009-529306 dated Oct. 18, 2012 (1 page, English Translation Only).

(56) References Cited

OTHER PUBLICATIONS

Karaman, M.W. et al., "A quantitative analysis of kinase inhibitor selectivity," Nature Biotech. (2008) 26(1):127-132.
Katritzky, A.R. et al., "Benzotriazole mediated amino-, amide-, alkoxy- and alkylthio-alkylation," Tetrahedron (2005) 61:2555-2581.
Lala, P.K. et al., "Role of nitric oxide in tumor progression: lessons from experimental tumors," Cancer and Metastasis Reviews (1998) 17:91-106.
Liljebris, C. et al., "Derivatives of 17-Pheny 1-18,19 ,20-trinorprostaglandin F2a Isopropyl Ester: Antiglaucoma Agents," J. Med. Chem. (1995) 38(2):289-304.
Loge, C; Siomboing, X et al. J, of Enzy Inhib & Med Chem, 2003, 18, 127-128.
Matsui, T. et al., "Novel 5-HT3 antagonists. Isoquinolinones and 3-aryl-2-pyridones," J. Med. Chem. (1992) 35:3307-3319.
McCutcheon's, "Emulsifiers & Detergents", North American Edition (1994) vol. 1:236-239.
Meanwell, "Synopsis of some recent tactocal application of bioisosteres in drug design," J. Med. Chem., 2011, vol. 54, pp. 2529-2591.
Nakanishi et al. FEBS Letters 368, (1995) 411-414.
Oakley, R.H. et al. "The Cellular Distribution of Fluorescently Labeled Arrestins Provides a Robust, Sensitive and Universal Assay for Screening G Protein-Coupled Receptors," Assay and Drug Development Technologies (2002) 1 (1-1):21-30.
Olson, "Application for ROCK kinase inhibition," Current Opinion in Cell Biology, 2008, vol. 20, pp. 242-248.
Parang, K. et al., "Design strategies for protein kinase inhibitors," Curr. Opin. In Drug Disc. & Dev. (2004) 7 (5):617-629.
Pardridge, "The Blood-Brain Barrier: Bottleneck in Brain Drug development," J. Am. Soc. Exper. NeuroTherapeutics, 2005, vol. 2, p. 3-14.
Partial International Search for Application No. PCT/US2009/031117 dated Apr. 16, 2009 ( 4 pages).
Penmetsa, K.V. et al., "Development of Reversed-Phase Chiral HPLC Methods Using Mass Spectrometry compatible Mobile Phases", J. Liquid Chroma. Rel. Tech. (2000) 23(6-10):831-839.
Penn, R.B. et al., "Pharmacological Inhibition of Protein Kinases in Intact Cells: Antagonism of Beta Adrenergic Receptor Ligand Binding by H-89 Reveals Limitations of Usefulness." J. Pharm. Exp. Ther. (1999) 288(2):428-437.
Pharmasolve (N-Methyl-2-Pyrrolidone) product specification, International Specialty Products, 2000, 10 pages.
PubChem, AC1 NQAJU (compound summary for CID 5172372) '372' date created: Sep. 26, 2005 date access: Jan. 5, 2016, 10 pages.
Rashid et al., "Development of Rho-kinase inhibitors for cardiovascular medicine," Trends in Pharmacological Science, 2007, vol. 28, pp. 296-302.
Shankar, G. et al., "Protein-kinase-specific inhibitors block Langerhans' cell migration by inhibiting interleukin-1arelease", Immunology (1999) 96:230-235.
Stirewalt, D.L. et al., "The Role of FLT3 in Haematopoietic Malignancies", Nature Reviews Cancer (2003) 3:650-665.
STN Registry Database entry for CAS RN 309903-43-6, Published in database Dec. 20, 2000.
Tamura, M., et al., "Development of specific Rho-kinase inhibitors and their clinical application," Biochimica et Biophysica Acta, 2005, vol. 1754, pp. 245-252.
Torres, G.E. et al. (2003). "Plasma membrane monoamine transporters: structure, regulation and function". Nat. Rev. Neurosci. 4 (1): 13-25.
United States Office Action for U.S. Appl. No. 11/485,182 dated Apr. 16, 2009 (13 pages).
United States Office Action for U.S. Appl. No. 11/621,892 dated Aug. 8, 2008 (9 pages).
United States Office Action for U.S. Appl. No. 11/621,892 dated Mar. 9, 2009 (6 pages).
United States Office Action for U.S. Appl. No. 12/274,887 dated Jun. 16, 2009 (11 pages).
United States Patent Office Action for U.S. Appl. No. 11/621,887 dated May 18, 2010 (8 pages).
United States Patent Office Action for U.S. Appl. No. 11/621,887 dated Oct. 29, 2010 (14 pages).
United States Patent Office Action for U.S. Appl. No. 11/856,740 dated Aug. 16, 2013 (14 pages).
United States Patent Office Action for U.S. Appl. No. 11/856,740 dated Dec. 6, 2010 (12 pages).
United States Patent Office Action for U.S. Appl. No. 11/856,740 dated Jun. 29, 2010 (10 pages).
United States Patent Office Action for U.S. Appl. No. 12/009,326 dated Feb. 3, 2011 (8 pages).
United States Patent Office Action for U.S. Appl. No. 12/180,259 dated Jul. 5, 2011 (11 pages).
United States Patent Office Action for U.S. Appl. No. 12/639,670 dated Jan. 31, 2011 (8 pages).
United States Patent Office Action for U.S. Appl. No. 12/639,670 dated Jul. 27, 2011 (5 pages).
United States Patent Office Action for U.S. Appl. No. 12/694,965 dated May 17, 2012 (13 pages).
United States Patent Office Action for U.S. Appl. No. 12/701,963 dated May 10, 2011 (3 pages).
United States Patent Office Action for U.S. Appl. No. 12/704,822 dated Apr. 30, 2012 (34 pages).
United States Patent Office Action for U.S. Appl. No. 12/704,822 dated May 8, 2014 (13 pages).
United States Patent Office Action for U.S. Appl. No. 12/704,822 dated Oct. 10, 2013 (11 pages).
United States Patent Office Action for U.S. Appl. No. 13/017,708 dated Apr. 3, 2012 (11 pages).
United States Patent Office Action for U.S. Appl. No. 13/230,105 dated Mar. 5, 2012 (8 pages).
United States Patent Office Action for U.S. Appl. No. 13/318,457 dated Jun. 6, 2013 (12 pages).
United States Patent Office Action for U.S. Appl. No. 13/723,811 dated Jan. 27, 2014 (8 pages).
United States Patent Office Action for U.S. Appl. No. 13/723,811 dated Jun. 17, 2014 (6 pages).
United States Patent Office Action for U.S. Appl. No. 13/768,594 dated Jul. 10, 2013 (14 pages).
"Cancer", MedlinePlus (retrieved Jul. 6, 2007) 10 pages, http://www.nlm.nih.gov/medlineplus/cancer.html.
Anonymous, "Aerie Pharmaceuticals, Inc. Gets Good News on Glaucoma Treatment" (20 Dec. 2, 2011) Retrieved from the Internet: URL:http://www.biospace.com.
Banker, G.S. et al., Modern Pharmaceutics, Marcel Dekker, Inc., New York, (1979) Chapters 9 and 10.
Berge et al, 1977, "Pharmaceutically Acceptable Salts." J. Pharm. Sci. vol. 66, pp. 1-19.
Bird, G.J. et al., "N-methyl as a bioisostere for the oxygen link between the aromatic rings of aryloxyphenoxypropionate herbicides," Bioorg. Med. Chem. Lett. (1997) 7:1489-1492.
Blough BE, Keverline KI, Nie Z, Navarro H, Kuhar MJ, Carroll FI (2002). "Synthesis and transporter binding properties of 3beta-[4'-(phenylalkyl, phenylalkenyl, and phenylalkynyl) phenyltropane]-2beta-carboxylic acid methyl esters: evidence of a remote phenyl binding domain on the dopamine transporter". J. Med. Chem. 45 (18):4029-37.
C.T.F.A. Cosmetic Ingredient Handbook, "Surfactants—Emulsifying Agents", Second Edition, The Cosmetic, Toiletry, and Fragrance Association, New York, Wenninger, J.A. et al., eds. (1992) 587-592.
Calmes et al., Eur. J. Org. Chem. 2000, 2459-2466.
Canadian Patent Office Action for Application No. 2,664,335 dated May 17, 2013 (2 pages).
Canadian Patent Office Action for Application No. 2,664,335 dated Nov. 15, 2013 (2 pages).
Capdeville, R. et al., "Glivec (STI571, IMATINIB), A Rationally Developed, Targeted Anticancer Drug", Nature Reviews Drug Discovery (2002) 1:493-502.
Chen, P. et al., "Identification of novel and potent isoquinoline aminooxazole-based IMPDH inhibitors," Bioorg. Med. Chem. Lett. (2003) 13(7):1345-1348.

(56) References Cited

OTHER PUBLICATIONS

Cheung, S.T. et al. Can. J. Chem. 1977, 55,906-910.
Dancey, J. et al., "Issues and Progress with Protein Kinase Inhibitors for Cancer Treatment", Nature Reviews Drug Discovery (2003) 2:296-313.
DeLong et al., "Discovery and SAR of a Class of Oculary-active Compounds Displaying a Dual Mechanism of Activity for the Treatment of Glaucoma" (20 Dec. 5, 2006) Retrieved from the Internet: URL:http://www.aeriepharma.com.
Dorwald, F.Z., Side Reactions in Organic Synthesis. A Guide to Successful Synthesis Design, Wiley-VCH, Weinheim (2005) IX of Preface and 1-15.
Dowton et al., "Influence of Liposomal Composition on Topical Delivery of Encapsulated Cyclosporin A", S.T.P. Pharma Sciences, vol. 3, pp. 404-407 (1993).
European Patent Office Action for Application No. 07814835.0 dated Jan. 4, 2016 (6 pages).
European Patent Office Action for Application No. 09702189.3 dated Dec. 28, 2011 (5 pages).
European Patent Office Action for Application No. 09702189.3 dated Feb. 1, 2011 (5 pages).
European Patent Office Action for Application No. 09790775.2 dated Oct. 24, 2011 (5 pages).
European Patent Office Action for Application No. 12003567.0 dated Jul. 24, 2013 (7 pages).
Extended European Patent Office Search Report for Application No. 12003567.0 dated Oct. 22, 2012 (8 pages).
Foye, Foye's Principles of Medicinal Chemistry, 5th Edition (2002) Lippencott, Williams, Wilkins, p. 59-63.
Gingras et al., "In Synthesis and evaluation of 4-(1-aminoalkyl)-N-(4-pyridyl)-cyclohexanecarboxamides as Rho-kinase inhibitors and neurite outgrowth promoters," Bioorganic & Medicinal Chemistry Letters, 2004, vol. 14, pp. 4931-4934.
Golub, T.R. et al., "Molecular classification of cancer: class discovery and class prediction by gene expression monitoring," Science (1999) 286:531-537.
Hackam, A.S. et al., "The Wnt Signaling Pathway in Retinal Degenerations", IUBMB Life (2005) 57(6):381-388.
Hazeldine, S.T. et al., "II. Synthesis and biological evaluation of some bioisosteres and cogeners of the anti tumour agent, 2{4[7-chloro-2-quinoxalinyl)oxy]phenoxy}propionic acid (XK469)," J. Med. Chem. (2002) 45:3130-3137.
He et al., "Further structure-activity relationship studies of piperidine-based monoamine transporter inhibitors: effects of piperidine ring stereochemistry on potency. Identification of norepinephrine transporter selective ligands and broad-spectrum transporter inhibitors". J. Med. Chem. 48 (25): 7970-9 (2005).
Helal, C.J. et al., "Discovery and SAR of 2-aminothiazole inhibitors of cyclin-dependent kinase 5/p25 as a potential treatment for Alzheimer's disease," Bioorg. Med. Chem. (2004) 14(22):5521-5525.
Helzner, "Bright New Ideas in Glaucoma Treatment" (2013) Retreived from the Internet: URL:http://mydigimag.rrd.com.
Hu, E. et al., "Rho kinase as potential therapeutic target for cardiovascular diseases: opportunities and challenges," Exp. Opin. Ther. Targets (2005) 9:715-736.
Inouye, Y. et al., "The Absolute Configurations of TRANS-1,2 Cyclopropanedicarboxylic Acid and Trans-2-Phenylcyclopropanecarboxylic Acid", Int'l. J. Org. Chem. (1964) 20(5)1695-1699.
International Preliminary Examination Report for Application No. PCT/US2006/026947 dated Jan. 24, 2008 (10 pages).
International Preliminary Report on Patentability for Application No. PCT/US08/50374 dated Jul. 14, 2009 (12 pages).
International Search Report and Written Opinion for Application No. PCT/US2006/026976 dated Feb. 15, 2007 (14 pages).
International Search Report and Written Opinion for Application No. PCT/US2007/078343 dated Apr. 15, 2008 (12 pages).
International Search Report and Written Opinion for Application No. PCT/US2009/031117 dated Sep. 24, 2009 (13 pages).
International Search Report and Written Opinion for Application No. PCT/US2009/051569 dated May 20, 2010 (11 pages).
International Search Report and Written Opinion for Application No. PCT/US2010/022246 dated Nov. 10, 2010 (7 pages).
International Search Report and Written Opinion for Application No. PCT/US2010/33316 dated Jul. 14, 2010 (10 pages).
International Search Report and Written Opinion for Application No. PCT/US2010/33317 dated Aug. 17, 2010 (10 pages).
International Search Report and Written Opinion for Application No. PCT/US2014/029335, dated Jul. 2, 2014 (11 pages).
International Search Report and Written Opinion for Application No. PCT/US2015/61177 dated Feb. 2, 2016 (16 pages).
International Search Report for Application No. PCT/US08/50374 dated Oct. 28, 2008 (7 pages).
International Search Report for Application No. PCT/US2006/026947 dated Nov. 17, 2006 ( 4 pages).
International Search Report PCT/US2007/078343 dated Apr. 15, 2008.
Invitation to Pay Additional Fees and Partial International Search Report for International Application No. PCT/US2009/051569 dated Oct. 15, 2009 (4 pages).
Ito, N. et al., "A medium-term rat liver bioassay for rapid in vivo detection of carcinogenic potential of chemicals," Cancer Science, Jan. 2003, vol. 94, No. 1, pp. 3-8.
Jacobs, M. et al., "The structure of dimeric ROCK I reveals the mechanism for ligand selectivity," J. Bio. Chem., 2006, pp. 260-268, published on Jan. 6, 2006.
Bosanac et al., Substituted 2H-isoquinolin-1-ones as potent Rho-kinase inhibitors: Part 3, aryl substituted pyrrolidines. Bioorganic & Medicinal Chemistry Letters, 20:3746-3749 (2010).
Ginn et al., Substituted 2H-isoquinolin-1-ones as potent Rho-kinase inhibitors: Part 2, optimization for blood pressure reduction in spontaneously hypertensive rats. Bioorganic & Medicinal Chemistry Letters, 20:5153-5156 (2010).
United States Patent Office Action for U.S. Appl. No. 14/138,592 dated Dec. 9, 2014 (14 pages).
United States Patent Office Action for U.S. Appl. No. 14/138,592 dated Jul. 28, 2014 (17 pages).
United States Patent Office Action for U.S. Appl. No. 14/213,940 dated Oct. 29, 2015 (33 pages).
United States Patent Office Action for U.S. Appl. No. 14/213,961 dated Oct. 30, 2015 (37 pages).
United States Patent Office Action for U.S. Appl. No. 14/273,895 dated Aug. 20, 2014 (8 pages).
United States Patent Office Action for U.S. Appl. No. 14/273,895 dated Dec. 24, 2014 (7 pages).
United States Patent Office Action for U.S. Appl. No. 14/461,597 dated Jan. 30, 2015 (19 pages).
United States Patent Office Action for U.S. Appl. No. 14/583,439 dated Jun. 23, 2015 (6 pages).
United States Patent Office Action for U.S. Appl. No. 14/583,439 dated Oct. 30, 2015 (7 pages).
United States Patent Office Action for U.S. Appl. No. 14/641,962 dated Sep. 22, 2015 (16 pages).
United States Patent Office Action for U.S. Appl. No. 14/754,787 dated Oct. 30, 2015 (20 pages).
United States Patent Office Action for U.S. Appl. No. 14/790,376 dated Jan. 22, 2016 (14 pages).
United States Patent Office Action for U.S. Appl. No. 15/076,216 dated Sep. 1, 2016 (6 pages).
United States Patent Office Advisory Action for U.S. Appl. No. 11/856,740 dated Feb. 10, 2011 (3 pages).
United States Patent Office Final Rejection for U.S. Appl. No. 12/704,822 dated Jan. 16, 2013 (16 pages).
United States Patent Office Final Rejection for U.S. Appl. No. 13/230,105 dated Jul. 9, 2012 (11 pages).
United States Patent Office Final Rejection for U.S. Appl. No. 13/318,457 dated Nov. 27, 2013 (13 pages).
United States Patent Office Final Rejection for U.S. Appl. No. 13/442,263 dated Dec. 6, 2013 (8 pages).
United States Patent Office Notice of Allowability for U.S. Appl. No. 13/017,708 dated Dec. 12, 2012 (5 pages).

(56) References Cited

OTHER PUBLICATIONS

United States Patent Office Notice of Allowance for U.S. Appl. No. 11/621,887 dated Feb. 27, 2013 (8 pages).
United States Patent Office Notice of Allowance for U.S. Appl. No. 11/856,740 dated Apr. 1, 2014 (8 pages).
United States Patent Office Notice of Allowance for U.S. Appl. No. 12/009,326 dated Feb. 25, 2013 (8 pages).
United States Patent Office Notice of Allowance for U.S. Appl. No. 12/009,326 dated Jan. 6, 2012 (5 pages).
United States Patent Office Notice of Allowance for U.S. Appl. No. 12/180,259 dated Dec. 19, 2011 (6 pages).
United States Patent Office Notice of Allowance for U.S. Appl. No. 12/180,259 dated Feb. 25, 2013 (8 pages).
United States Patent Office Notice of Allowance for U.S. Appl. No. 12/694,965 dated Nov. 19, 2012 (4 pages).
United States Patent Office Notice of Allowance for U.S. Appl. No. 12/694,965 dated Nov. 2, 2012 (8 pages).
United States Patent Office Notice of Allowance for U.S. Appl. No. 12/704,822 dated Sep. 9, 2014 (11 pages).
United States Patent Office Notice of Allowance for U.S. Appl. No. 13/017,708 dated Oct. 23, 2012 (7 pages).
United States Patent Office Notice of Allowance for U.S. Appl. No. 13/017,708 dated Sep. 17, 2012 (8 pages).
United States Patent Office Notice of Allowance for U.S. Appl. No. 13/230,105 dated Mar. 19, 2013 (5 pages).
United States Patent Office Notice of Allowance for U.S. Appl. No. 13/442,263 dated Apr. 15, 2014 (8 pages).
United States Patent Office Notice of Allowance for U.S. Appl. No. 13/442,263 dated Dec. 19, 2012 (13 pages).
United States Patent Office Notice of Allowance for U.S. Appl. No. 13/442,263 dated Feb. 25, 2013 (8 pages).
United States Patent Office Notice of Allowance for U.S. Appl. No. 13/442,263 dated Jun. 12, 2013 (8 pages).
United States Patent Office Notice of Allowance for U.S. Appl. No. 13/723,811 dated Aug. 19, 2014 (11 pages).
United States Patent Office Notice of Allowance for U.S. Appl. No. 13/768,594 dated Oct. 29, 2013 (7 pages).
United States Patent Office Notice of Allowance for U.S. Appl. No. 14/213,961 dated Jun. 20, 2016 (8 pages).
United States Patent Office Notice of Allowance for U.S. Appl. No. 14/273,895 dated Apr. 1, 2015 (8 pages).
United States Patent Office Notice of Allowance for U.S. Appl. No. 14/583,439 dated Feb. 12, 2016 (8 pages).
United States Patent Office Notice of Allowance for U.S. Appl. No. 14/790,376 dated Aug. 2, 2016 and Aug. 19, 2016 (10 pages).
Van Muijl Wijk-Koezen et al., "A novel class of adenosine A3 receptor-ligands. 2. Structure affinity profile of a series of isoquinoline and quinazoline compounds," J. Med. Chem. ( 1998) 41:3994-4000.
Wallach and Philippot, "New Type of Lipid Vesicle: Novasome®", Liposome Technology, vol. 1, pp. 141-156 (1993).
Webster, F.X. et al., "Following the Course of Resolution of Carboxylic Acids by 13C NMR Spectrometry of Amine Salts" J. Org. Chem. (1982) 47(26):5225-5226.
West, A.R., "Solid state chemistry and its applications," Wiley, New York (1988) pp. 358 and 365.
Westaway, S.M. et al., "N-tetrahydroquinolinyl, N-quinolinyl and N-isoquinolinyl biaryl carboxamides as antagonists of TRPV1," Biorg. Med. Chem. Lett. (2006) 16:4533-4536.
Westra, J. et al., "p38 Mitogen-Activated Protein Kinase (MAPK) in Rheumatoid Arthritis", Mini-Reviews in Medicinal Chemistry (2006) 6(8):867-874.
Yamashita et al., "The therapeutic effects of Rho-Rock inhibitors on CNS disorder," Therapeutics and Clinical Risk Management, 2008, vol. 4, pp. 605-615.

\* cited by examiner

RHO KINASE INHIBITORS

RELATED APPLICATIONS

This application is a continuation of U.S. patent application Ser. No. 15/142,448 filed Apr. 29, 2016, which is a continuation of U.S. patent application Ser. No. 14/754,787 filed Jun. 30, 2015, which is a continuation of U.S. patent application Ser. No. 14/461,597, filed Aug. 18, 2014, which is a divisional of U.S. patent application Ser. No. 11/856,740, filed Sep. 18, 2007, now U.S. Pat. No. 8,809,326 issued Aug. 19, 2014, which claims priority to U.S. Provisional Patent Application No. 60/864,484, filed Nov. 6, 2006, and U.S. Provisional Patent Application No. 60/826,284, filed Sep. 20, 2006, each of which is incorporated herein by reference in its entirety.

FIELD OF THE INVENTION

This invention relates to substituted 2H-isoquinolin-1-one and 3H-quinazolin-4-one derivatives which are useful as inhibitors of Rho kinase and are thus useful for treating a variety of diseases and disorders that are mediated or sustained through the activity of Rho kinase, including cardiovascular diseases, cancer, neurological diseases, renal diseases, bronchial asthma, erectile dysfunction, and glaucoma. This invention also relates to pharmaceutical compositions comprising these compounds, methods of using these compounds in the treatment of various diseases and disorders, processes for preparing these compounds and intermediates useful in these processes.

BACKGROUND

Rho-Kinase (ROCK) is a member of the serine-threonine protein kinase family. ROCK exists in two isoforms, ROCK1 and ROCK2 (T. Ishizaki et al., EMBO J., 1996, 15, 1885-1893). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as acting organization, cell adhesion, cell migration, and cytokinesis (K. Riento and A. J. Ridley, Nat Rev Mol Cell Biol, 2003, 4, 446-56). It is also directly involved in regulating smooth muscle contraction (A. P. Somlyo, Nature, 1997, 389, 908-911). Upon activation of its receptor, RhoA is activated and in turn it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho/ROCK signaling pathway plays an important role in signal transduction initiated by several vasoactive factors, for example angiotensin II, urotension II, endothelin-1, serotonin, norepinephrine and platelet-derived growth factor (PDGF). Many of these factors are implicated in the pathogenesis of cardiovascular disease.

Additional studies in the literature, some using known ROCK inhibitors fasudil (T. Asano et al., J. Pharmacol. Exp. Ther., 1987, 24, 1033-1040) or Y-27632 (M. Uehata et al., Nature, 1997, 389, 990-994) further illustrate the link between ROCK and cardiovascular disease. For example, ROCK expression and activity have been shown to be elevated in spontaneously hypertensive rats, suggesting a link to the development of hypertension in these animals. The ROCK inhibitor Y-27632 (M. Uehata et al., Nature, ibid) was shown to significantly decrease blood pressure in three rat models of hypertension, including the spontaneously hypertensive rat, renal hypertensive rat and deoxycortisone acetate salt hypertensive rat models while having only a minor effect on blood pressure in control rats, reinforcing the link between ROCK and hypertension.

Other studies suggest a link between ROCK and atherosclerosis. For example, gene transfer of a dominant negative form of ROCK suppressed neointimal formation following balloon injury in porcine femoral arteries. In a similar model, ROCK inhibitor Y-27632 also inhibited neointimal formation in rats. In a porcine model of IL-1 beta-induced coronary stenosis, long term treatment by ROCK inhibitor fasudil was shown to progressively reduce coronary stenosis as well as promote a regression of coronary constrictive remodeling.

Additional investigations suggest that a ROCK inhibitor would be useful in treating other cardiovascular diseases. For example, in a rat stroke model, fasudil was shown to reduce both the infarct size and neurologic deficit. The ROCK inhibitor Y-27632 was shown to improve ventricular hypertrophy and function in a model of congestive heart failure in Dahl salt-sensitive rats.

Other animal or clinical studies have implicated ROCK in additional discuses including coronary vasospasm, cerebral vasospasm, ischemia/reperfusion injury, pulmonary hypertension, angina, renal disease and erectile dysfunction.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper reactivity, including asthma and glaucoma. Furthermore, Rho-kinase has been indicated as a drug target for the treatment of various other diseases, including airway inflammation and hyperresponsiveness, cancer, as well as neurological disorders, such as spinal-cord injury, Alzheimer disease, multiple sclerosis, stroke and neuropathic pain.

There remains an unmet medical need for new drugs to treat cardiovascular disease. A study published in 2003 estimated that almost 29% of the adult U.S. population had hypertension in 1999-2000 (I. Hajjar et al., JAMA, 2003, 290, 199-206). Furthermore, 69% of the hypertensive individuals studied during this period did not have their hypertension controlled at the time their blood pressure was measured. This figure was worse in hypertensive patients with diabetes, where 75% of those patients studied did not have their blood pressure controlled to the target level. Another more recent study showed similar results, with less than one-third of hypertensive patients studied having blood pressure controlled to the target level (V. Andros, Am. J. Manag. Care, 2005, 11, S215-S219). Therefore, despite the number of medications available to treat hypertension, including diuretics, beta blockers, angiotensin converting enzyme inhibitors, angiotensin blockers and calcium channel blockers, hypertension remains poorly controlled or resistant to current medication for many patients. If not adequately treated, hypertension can lead to other cardiovascular diseases and organ failure including coronary artery disease, stroke, myocardial infarction, cardiac failure, renal failure and peripheral artery disease.

Although there are many reports of ROCK inhibitors under investigation (see, for example, E. Hu and D. Lee, Expert Opin. Ther. Targets, 2005, 9, 715-736), so far fasudil is the only marketed ROCK inhibitor. An i.v. formulation of fasudil was approved in Japan for treatment of cerebral vasospasm. There remains a need for new therapeutics, including ROCK inhibitors, for the treatment of cardiovascular diseases, cancer, neurological diseases, renal diseases, bronchial asthma, erectile dysfunction, and glaucoma.

BRIEF SUMMARY OF THE INVENTION

In a general aspect, the present invention is directed to the compounds of the following formula (I):

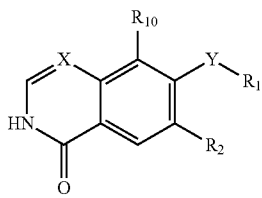

wherein $R_1$, $R_2$, X and Y are as defined herein, as well as the tautomers thereof, and salts thereof. It has been found that the compounds of formula (I) have valuable pharmacological properties, particularly an inhibiting activity on Rho kinase.

In another aspect, the present invention is directed to a method of inhibiting Rho kinase activity in an individual comprising administering to the individual a compound described above.

In another aspect, the present invention is directed to a method of treating a disease or disorder associated with the activation of Rho kinase comprising administering to an individual a compound described above.

In another aspect, the present invention is directed to a method of treating a cardiovascular or disease or condition comprising administering to an individual a compound described above. Examples of such diseases that may be treated include, for example, hypertension, atherosclerosis, stroke, heart failure, restenosis, myocardial infarction, organ failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma and glaucoma, comprising administering to an individual a compound described above.

In another aspect, the present invention is directed to a method of treating diseases involving Rho-kinase under pathophysiological conditions, including airway inflammation and hyperresponsiveness, cancer, and various neurological diseases, comprising administering to an individual in need of such treatment a compound of the present invention as described above.

In yet additional aspects, the present invention is directed to pharmaceutical compositions comprising the above-mentioned compounds, processes for preparing the above-mentioned compounds and intermediates used in these processes.

DETAILED DESCRIPTION OF THE INVENTION

In an embodiment, there is provided compounds of the formula (I)

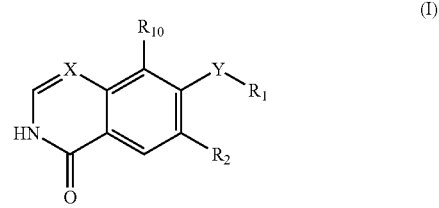

wherein:
$R_1$ is chosen from
$C_{1-6}$alkyl, $C_{3-8}$cycloalkyl, $C_{3-8}$cycloalkyl$C_{1-6}$alkyl, halo$C_{1-6}$alkyl, amino$C_{1-6}$alkyl, hydroxy$C_{1-6}$alkyl, aryl, aryl$C_{1-6}$alkyl, heteroaryl, heteroaryl$C_{1-6}$alkyl, heterocyclyl, —$C_{1-3}$alkylOaryl, —C(H)$_{0-1}$($C_{1-6}$alkyl)$_{1-2}$aryl, —CH(OH)aryl, —C(OH)(CH$_3$)aryl, —CH[OC(O)$C_{1-6}$alkyl]aryl, —CH$_2$OCH$_2$aryl, —CH$_2$OC(O)$C_{1-6}$alkyl, —(CH$_2$)$_{1-3}$S(O)$_{0-2}$aryl, —(CH$_2$)$_{1-2}$S(O)$_{0-2}$$C_{1-6}$alkyl, —(CH$_2$)$_{1-3}$CO$_2$$C_{1-6}$alkyl, —(CH2)$_{1-3}$NH$C_{1-6}$alkyl, —(CH$_2$)$_{1-3}$NH$C_{1-6}$alkyl$C_{3-8}$cycloalkyl, —(CH$_2$)$_{1-2}$CN and —CH(R$_3$)N(R$_4$)(R$_5$)
wherein:
$R_3$ is chosen from
H, aryl, $C_{1-6}$alkyl, —(CH$_2$)$_{1-3}$aryl and —(CH$_2$)$_{1-3}$heteroaryl;
$R_4$ is chosen from
H, $C_{1-6}$alkyl, $C_{3-12}$cycloalkyl, $C_{3-7}$cycloalkyl$C_{1-6}$alkyl, aryl, aryl(CH$_2$)$_{1-3}$, heteroaryl(CH$_2$)$_{1-3}$, $C_{1-3}$alkylO(CH$_2$)$_{1-3}$, tetrahydropyran-4-ylmethyl and $C_{1-3}$alkyl)$_2$N(CH$_2$)$_{2-4}$—; and $R_5$ is chosen from
H and $C_{1-6}$alkyl;
or $R_4$ and $R_5$ together with the nitrogen atom they are connected to may form a heterocyclyl group;
wherein each aryl, arylalkyl, heteroaryl, heteroarylalkyl, cycloalkylalkyl, cycloalkyl and heterocyclyl group is optionally substituted with 1-3 groups selected from
halogen, $C_{1-6}$alkoxy, $C_{3-8}$cycloalkyl, $C_{1-6}$alkyl, —CN, —NO$_2$, —OH, oxo, —CF$_3$, —OCF$_3$, —$C_{0-3}$, alkylCO$_2$H, $C_{1-6}$alkylCO$_2$-, $C_{1-6}$alkylsulfonyl$C_{0-3}$alkyl-, —SO$_2$$C_{1-6}$alkylNR$_6$R$_7$, —$C_{0-3}$alkylSO$_2$NR$_6$R$_7$, —$C_{0-3}$C(O)NR$_6$R$_7$, aryl, heteroaryl, heteroaryl$C_{1-3}$alkyl, heterocyclyl, heterocyclylSO$_2$-, aryl$C_{1-3}$alkyl, aryloxy, arylthio and $C_{0-3}$NR$_6$R$_7$;
wherein each aryl and heteroaryl group is optionally substituted with 1-3 groups selected from
halogen, $C_{1-6}$alkoxy, $C_{1-6}$alkyl, —CN, —NO$_2$, —OH, —CF$_3$, —OCF$_3$, —C(O)NR$_8$R$_9$, —SO$_2$NR$_8$R$_9$, —SO$_2$Me and amino optionally substituted by one or two $C_{1-6}$alkyl groups or a C(O)$C_{1-6}$alkyl group;
$R_2$ is chosen from H, halogen, $C_{1-6}$alkoxy, —CN, —CF$_3$ and $C_{1-6}$alkyl;
$R_6$ and $R_7$ are independently selected from H, $C_{1-6}$alkyl, —C(O)$C_{1-6}$alkyl and —$C_{1-6}$alkylNH$_2$; or
$R_6$ and $R_7$, together with the nitrogen they are connected to may form a piperazine, piperidine or pyrrolidine ring;
$R_8$ and $R_9$ are independently selected from H and methyl;
$R_{10}$ is selected from H, Cl and F;
X is chosen from C and N; and
Y is chosen from —NHC(O)—, —NHC(O)NH— and —NHC(O)O—;

or a tautomer thereof or a salt thereof, preferably a pharmaceutically acceptable salt thereof. Preferably if $R_1$ is a $C_{1-6}$alkyl, and Y is —NHC(O)—, then $R_i$ is not a methyl group.

In an embodiment, there is provided compounds of the formula (I)

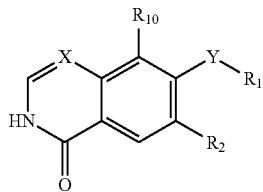

wherein:
$R_1$ is chosen from
$C_{3-8}$cycloalkyl, $C_{3-8}$cycloalkyl$C_{1-6}$alkyl, halo$C_{1-6}$alkyl, amino$C_{1-6}$alkyl, hydroxy$C_{1-6}$alkyl, aryl, aryl$C_{1-6}$alkyl, heteroaryl, heteroaryl$C_{1-6}$alkyl, heterocyclyl, —$C_{1-3}$alkylOaryl, —C(H)$_{0-1}$*($C_{1-6}$alkyl)$_{1-2}$aryl, —CH(OH)aryl, —C(OH)(CH$_3$)aryl, —CH[OC(O)$C_{1-6}$alkyl]aryl, —CH$_2$OCH$_2$aryl, —CH$_2$OC(O)$C_{1-6}$alkyl, —(CH$_2$)$_{1-3}$S(O)$_{0-2}$aryl, —(CH$_2$)$_{1-2}$S(O)$_{0-2}$$C_{1-6}$alkyl, —(CH$_2$)$_{1-3}$CO$_2$$C_{1-6}$alkyl, —(CH$_2$)$_{1-3}$NHC$_{1-6}$alkyl, —(CH$_2$)$_{1-3}$NHC$_{1-6}$alkyl$C_{3-8}$cycloalkyl, —(CH$_2$)$_{1-2}$CN and —CH($R_3$)N($R_4$)($R_5$);
wherein:
$R_3$ is chosen from
H, aryl, $C_{1-6}$alkyl, —(CH$_2$)$_{1-3}$aryl and —(CH$_2$)$_{1-3}$heteroaryl;
$R_4$ is chosen from
H, $C_{1-6}$alkyl, $C_{3-12}$cycloalkyl, $C_{3-7}$cycloalkyl$C_{1-6}$alkyl, aryl, aryl(CH$_2$)$_{1-3}$, heteroaryl(CH$_2$)$_{1-3}$, $C_{1-3}$alkylO(CH$_2$)$_{1-3}$, tetrahydropyran-4-ylmethyl and ($C_{1-3}$alkyl)$_2$N(CH$_2$)$_{2-4}$—; and $R_5$ is chosen from
H and $C_{1-6}$alkyl;
or $R_4$ and $R_5$ together with the nitrogen atom they are connected to may form a heterocyclyl group;
wherein each aryl, arylalkyl, heteroaryl, heteroarylalkyl, cycloalkylalkyl, cycloalkyl and heterocyclyl group is optionally substituted with 1-3 groups selected from
halogen, $C_{1-6}$alkoxy, $C_{3-8}$cycloalkyl, $C_{1-6}$alkyl, —CN, —NO$_2$, —OH, oxo, —CF$_3$, —OCF$_3$, —$C_{1-3}$alkylCO$_2$H, $C_{1-6}$alkylCO$_2$-, $C_{1-6}$alkylsulfonyl$_{0-3}$alkyl-, —SO$_2$C$_{1-6}$alkylNR$_6$R$_7$, —C$_{0-3}$alkylSO$_2$NR$_6$R$_7$, —C$_{0-3}$C(O)NR$_6$R$_7$, aryl, heteroaryl, heteroaryl$C_{1-3}$alkyl, heterocyclyl, heterocyclylSO$_2$-, arylC$_{1-3}$alkyl, aryloxy, arylthio and $C_{0-3}$NR$_6$R$_7$;
wherein each aryl and heteroaryl group is optionally substituted with 1-3 groups selected from
halogen, $C_{1-6}$alkoxy, $C_{1-6}$alkyl, —CN, —NO$_2$, —OH, —CF$_3$, —OCF$_3$, —C(O)NR$_8$R$_9$, —SO$_2$NR$_8$R.sub.$_9$— SO$_2$Me and amino optionally substituted by one or two $C_{1-6}$alkyl groups or a C(O)$C_{1-6}$alkyl group;
$R_2$ is chosen from H, halogen, $C_{1-6}$alkoxy, —CN, —CF$_3$ and $C_{1-6}$alkyl;
$R_6$ and $R_7$ are independently selected from H, $C_{1-6}$alkyl, —C(O)$C_{1-6}$alkyl and —$C_{1-6}$alkylNH$_2$; or
$R_6$ and $R_7$, together with the nitrogen they are connected to may form a piperazine, piperidine or pyrrolidine ring;
$R_8$ and $R_9$ are independently selected from H and methyl;
$R_{10}$ is selected from H, Cl and F;
X is chosen from C and N; and
Y is chosen from —NHC(O)—, —NHC(O)NH— and —NHC(O)O—;

or a tautomer thereof or a salt thereof, preferably a pharmaceutically acceptable salt.

In another embodiment, there are provided compounds of the formula (I) as described above and wherein:
$R_1$ is chosen from
$C_{3-8}$cycloalkyl, $C_{3-8}$cycloalkyl$C_{1-6}$alkyl, phenyl, benzyl, phenylethyl, thienyl, pyridyl, isoxazolyl, pyrazolyl, thienylmethyl, piperidinyl, piperazinyl, pyrrolidinyl, tetrahydrofuranyl, tetrahydropyranyl, —CH$_2$Ophenyl, —CH($C_{1-3}$alkyl)phenyl, —CH(OH)phenyl, —C(OH)(CH$_3$)phenyl, —CH[OC(O)CH$_3$]phenyl, —CH$_2$OCH$_2$phenyl, —CH$_2$OC(O)$C_{1-6}$alkyl, —(CH$_2$)$_{1-3}$S(O)$_{0-2}$phenyl, —(CH$_2$)$_{1-2}$S(O)$_{0-2}$$C_{1-6}$alkyl, —(CH$_2$)$_{1-3}$CO$_2$$C_{1-6}$alkyl, —(CH$_2$)$_{1-3}$NHC$_{1-6}$alkyl, —(CH$_2$)$_{1-3}$NHC$_{1-6}$alkyl$C_{3-8}$cycloalkyl, —(CH$_2$)$_{1-3}$CN and —CH($R_3$)N($R_4$)($R_5$);
wherein:
$R_3$ is chosen from
H, phenyl, $C_{1-6}$alkyl, benzyl phenylethyl and pyridylmethyl;
$R_4$ is chosen from
H, $C_{1-6}$alkyl, $C_{3-12}$cycloalkyl, $C_{3-7}$cycloalkyl$C_{1-6}$alkyl, phenyl, benzyl, thienylethyl, $C_{1-3}$ alkylO(CH$_2$)$_{1-3}$, tetrahydropyran-4-ylmethyl and ($C_{1-3}$)$_2$N(CH$_2$)$_{2-4}$—; and $R_5$ chosen from
H and $C_{1-6}$alkyl;
or $R_4$ and $R_5$ together with the nitrogen atom they are connected to may form a piperidine, piperazine or thiomorpholine group;
wherein each cycloalkyl, cycloalkylalkyl, phenyl, benzyl, phenylethey, thienyl, pyridyl, isoxazolyl, pyrazolyl, thienylmethyl, piperidine, piperazinyl, pyrrolidinyl, tetrahydrofuranyl, tetrahydropyranyl, and thiomorpholinyl group is optionally substituted with 1-3 groups selected from
halogen, $C_{1-6}$alkoxy, $C_{1-6}$alkyl, —CN, —NO$_2$, —OH, —CF$_3$, —OCF$_3$, $C_{1-6}$alkylCO$_2$-, $C_{1-6}$alkylsulfonyl, phenyl, pyrimidyl, pyridyl, morpholinyl, benzyl, phenyloxy and phenylthio and amino optionally substituted by one or two $C_{1-6}$alkyl groups or a C(O)$C_{1-6}$alkyl group; wherein each phenyl, benzyl, pyrimidinyl and pyridyl group is optionally substituted with 1-3 groups selected from
halogen, $C_{1-6}$alkoxy, $C_{1-6}$alkyl, —CN, —NO$_2$, —OH, —CF$_3$, —OCF$_3$, —C(O)NR$_8$R$_9$, —SO$_2$NR$_8$R$_9$, —SO$_2$Me and amino optionally substituted by one or two $C_{1-6}$alkyl groups or a C(O)$C_{1-6}$alkyl group;
$R_2$ is chosen from H, Br, Cl, —CN, —CF$_3$ and methyl;
$R_8$ and $R_9$ are independently selected from H and methyl;
$R_{10}$ is selected from H, Cl and F;
X is chosen from C and N; and
Y is chosen from —NHC(O)—, —NHC(O)NH— and —NHC(O)O—;
or a tautomer thereof or a salt thereof, preferably a pharmaceutically acceptable salt thereof.

In a further embodiment, there are provided compounds of the formula (I) as described above and wherein:
$R_1$ is chosen from
cyclopentyl, cyclohexyl, phenyl, benzyl, phenylethyl, thienylmethyl, piperidinyl, pyrrolodinyl, —CH$_2$Sphenyl and —CH($R_3$)N($R_4$)($R_5$)
wherein:
$R_3$ is chosen from
H, phenyl, $C_{1-6}$alkyl, benzyl and phenylethyl;
$R_4$ is chosen from
H, $C_{1-6}$alkyl, $C_{3-12}$cycloalkyl, $C_{3-7}$cycloalkylmethyl, benzyl, thienylethyl, and tetrahydropyran-4-ylmethyl;
and $R_5$ is chosen from
H and methyl;
or $R_4$ and $R_5$ together with the nitrogen atom they are connected to may form a piperidine group;

wherein each cyclopentyl, cyclohexyl, phenyl, benzyl, phenylethyl, thienylmethyl, piperidinyl and pyrrolidinyl group is optionally substituted with 1-3 groups selected from halogen, $C_{1-6}$alkoxy, $C_{1-6}$alkyl, —CN, —NO$_2$, —OH—CF$_3$, —OCF$_3$, phenyl and amino optionally substituted by one or two $C_{1-6}$alkyl groups or a C(O)C$_{1-6}$alkyl group; wherein each phenyl group is optionally substituted with 1-3 groups selected from halogen, $C_{1-6}$alkoxy, $C_{1-6}$alkyl, —CN, —NO$_2$, —OH, —CF$_3$, —OCF$_3$, and amino optionally substituted by one or two $C_{1-6}$alkyl groups or a C(O)C$_{1-6}$alkyl group;

$R_2$ is chosen from H, Br and Cl;
$R_{10}$ is H;
X is chosen from C and N; and
Y is —NHC(O)—
or a tautomer thereof or a salt thereof, preferably a pharmaceutically acceptable salt thereof.

In still a further embodiment of the invention, there are provided compounds of the formula (I) selected from the group below or a tautomer thereof or a salt thereof, preferably a pharmaceutically acceptable salt thereof:

| Structure | Name |
|---|---|
| 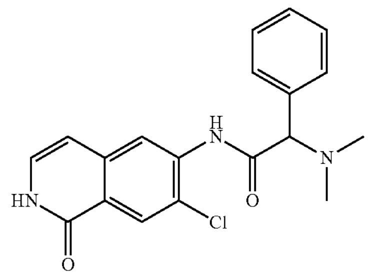 [SMILES: CN(C)C(C(=O)Nc1cc2cc[nH]c(=O)c2cc1Cl)c1ccccc1] | N-(7-Chloro-1-oxo-1,2-dihydro-isoquinolin-6-yl)-2-dimethylamino-2-phenyl-acetamide |
| 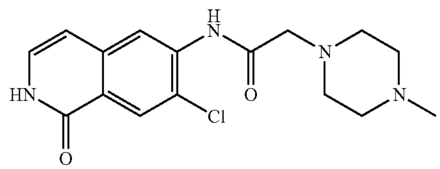 [SMILES: CN1CCN(CC(=O)Nc2cc3cc[nH]c(=O)c3cc2Cl)CC1] | N-(7-Chloro-1-oxo-1,2-dihydro-isoquinolin-6-yl)-2-(4-methyl-piperazin-1-yl)-acetamide |
| 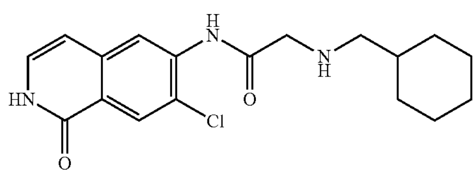 [SMILES: O=C(CNCC1CCCCC1)Nc1cc2cc[nH]c(=O)c2cc1Cl] | N-(7-Chloro-1-oxo-1,2-dihydro-isoquinolin-6-yl)-2-(cyclohexylmethyl-amino)-acetamide |
| 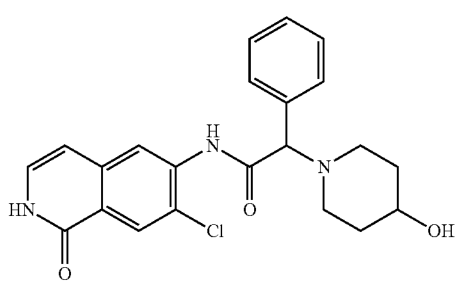 [SMILES: O=C(Nc1cc2cc[nH]c(=O)c2cc1Cl)C(c1ccccc1)N1CCC(O)CC1] | N-(7-Chloro-1-oxo-1,2-dihydro-isoquinolin-6-yl)-2-(4-hydroxy-piperidin-1-yl)-2-phenyl-acetamide |
| 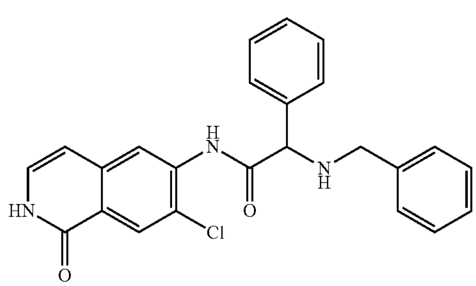 [SMILES: O=C(Nc1cc2cc[nH]c(=O)c2cc1Cl)C(NCc1ccccc1)c1ccccc1] | 2-Benzylamino-N-(7-chloro-1-oxo-1,2-dihydro-isoquinolin-6-yl)-2-phenyl-acetamide |

-continued

| Structure | Name |
|---|---|
| 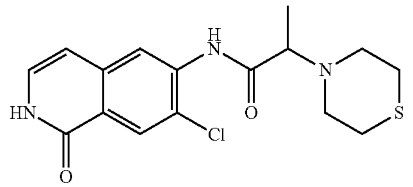 [SMILES: CC(C(=O)Nc1cc2cc[nH]c(=O)c2cc1Cl)N1CCSCC1] | N-(7-Chloro-1-oxo-1,2-dihydro-isoquinolin-6-yl)-2-thiomorpholin-4-yl-propionamide |
| 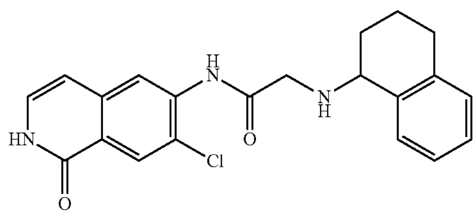 [SMILES: O=C(CNC1CCCc2ccccc21)Nc1cc2cc[nH]c(=O)c2cc1Cl] | N-(7-Chloro-1-oxo-1,2-dihydro-isoquinolin-6-yl)-2-(1,2,3,4-tetrahydro-naphthalen-1-ylamino)-acetamide |
| 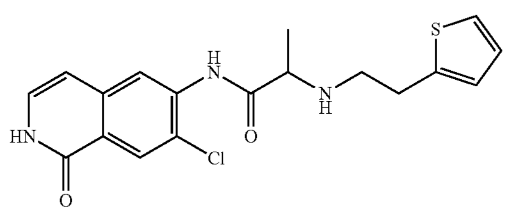 [SMILES: CC(NCCc1cccs1)C(=O)Nc1cc2cc[nH]c(=O)c2cc1Cl] | N-(7-Chloro-1-oxo-1,2-dihydro-isoquinolin-6-yl)-2-(2-thiophen-2-yl-ethylamino)-propionamide |
| 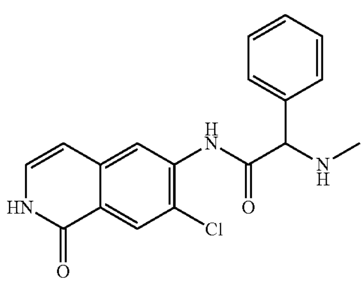 [SMILES: CNC(C(=O)Nc1cc2cc[nH]c(=O)c2cc1Cl)c1ccccc1] | N-(7-Chloro-1-oxo-1,2-dihydro-isoquinolin-6-yl)-2-methylamino-2-phenyl-acetamide |
| 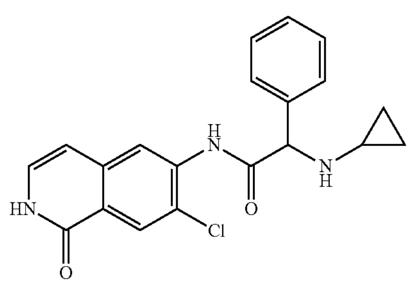 [SMILES: O=C(Nc1cc2cc[nH]c(=O)c2cc1Cl)C(NC1CC1)c1ccccc1] | N-(7-Chloro-1-oxo-1,2-dihydro-isoquinolin-6-yl)-2-cyclopropylamino-2-phenyl-acetamide |
| 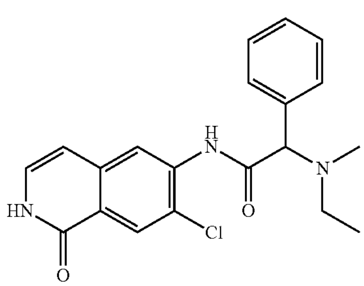 [SMILES: CCN(C)C(C(=O)Nc1cc2cc[nH]c(=O)c2cc1Cl)c1ccccc1] | N-(7-Chloro-1-oxo-1,2-dihydro-isoquinolin-6-yl)-2-(ethyl-methyl-amino)-2-phenyl-acetamide |

-continued

| Structure | Name |
|---|---|
| 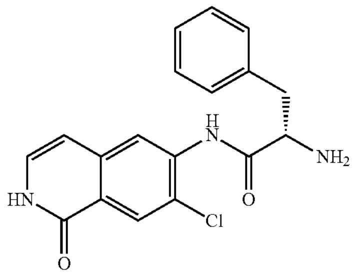 [SMILES: N[C@@H](Cc1ccccc1)C(=O)Nc1cc2cc[nH]c(=O)c2cc1Cl] | (S)-2-Amino-N-(7-chloro-1-oxo-1,2-dihydro-isoquinolin-6-yl)-3-phenyl-propionamide |
| 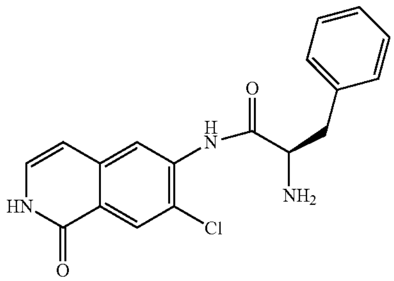 [SMILES: N[C@H](Cc1ccccc1)C(=O)Nc1cc2cc[nH]c(=O)c2cc1Cl] | (R)-2-Amino-N-(7-chloro-1-oxo-1,2-dihydro-isoquinolin-6-yl)-3-phenyl-propionamide |
| 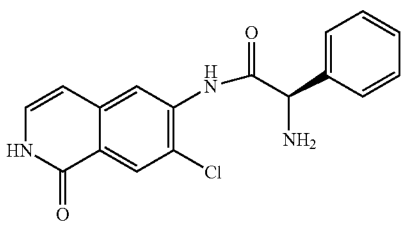 [SMILES: N[C@@H](C(=O)Nc1cc2cc[nH]c(=O)c2cc1Cl)c1ccccc1] | (R)-2-Amino-N-(7-chloro-1-oxo-1,2-dihydro-isoquinolin-6-yl)-2-phenyl-acetamide |
| 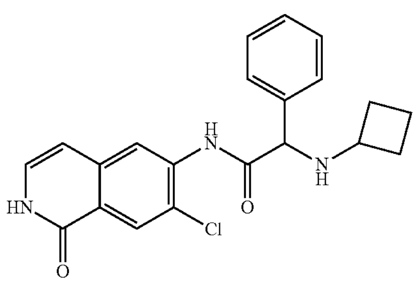 [SMILES: O=C(Nc1cc2cc[nH]c(=O)c2cc1Cl)C(NC1CCC1)c1ccccc1] | N-(7-Chloro-1-oxo-1,2-dihydro-isoquinolin-6-yl)-2-cyclobutylamino-2-phenyl-acetamide |
| 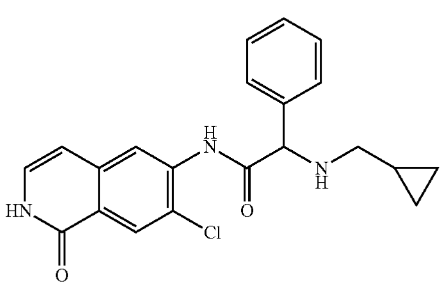 [SMILES: O=C(Nc1cc2cc[nH]c(=O)c2cc1Cl)C(NCC1CC1)c1ccccc1] | N-(7-Chloro-1-oxo-1,2-dihydro-isoquinolin-6-yl)-2-(cyclopropylmethyl-amino)-2-phenyl-acetamide |

-continued

| Structure | Name |
|---|---|
| 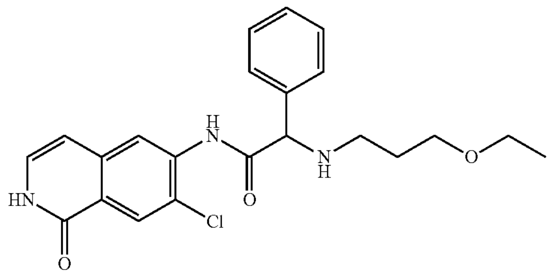 [SMILES: CCOCCCNC(C(=O)Nc1cc2cc[nH]c(=O)c2cc1Cl)c1ccccc1] | N-(7-Chloro-1-oxo-1,2-dihydro-isoquinolin-6-yl)-2-(3-ethoxy-propylamino)-2-phenyl-acetamide |
| 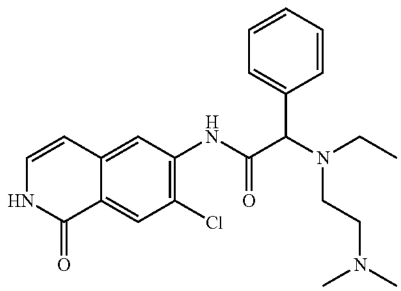 [SMILES: CCN(CCN(C)C)C(C(=O)Nc1cc2cc[nH]c(=O)c2cc1Cl)c1ccccc1] | N-(7-Chloro-1-oxo-1,2-dihydro-isoquinolin-6-yl)-2-[(2-dimethylamino-ethyl)-ethyl-amino]-2-phenyl-acetamide |
| 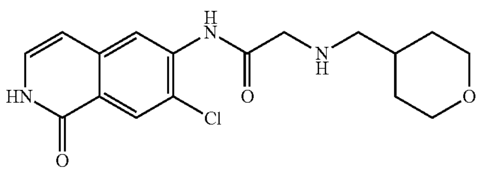 [SMILES: O=C(CNCC1CCOCC1)Nc1cc2cc[nH]c(=O)c2cc1Cl] | N-(7-Chloro-1-oxo-1,2-dihydro-isoquinolin-6-yl)-2-[(tetrahydro-pyran-4-ylmethyl)-amino]-acetamide |
| 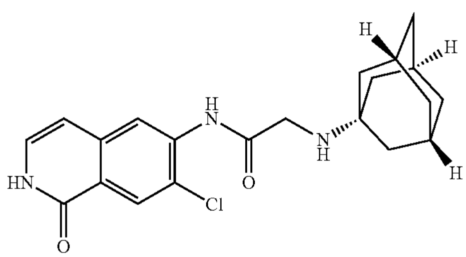 [SMILES: O=C(CN[C@]12C[C@H]3C[C@H](C[C@H](C3)C1)C2)Nc1cc2cc[nH]c(=O)c2cc1Cl] | 2-(Adamantan-1-ylamino)-N-(7-chloro-1-oxo-1,2-dihydro-isoquinolin-6-yl)-acetamide |
| 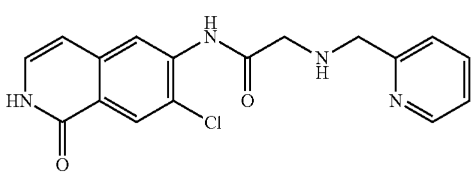 [SMILES: O=C(CNCc1ccccn1)Nc1cc2cc[nH]c(=O)c2cc1Cl] | N-(7-Chloro-1-oxo-1,2-dihydro-isoquinolin-6-yl)-2-[(pyridin-2-ylmethyl)-amino]-acetamide |
| 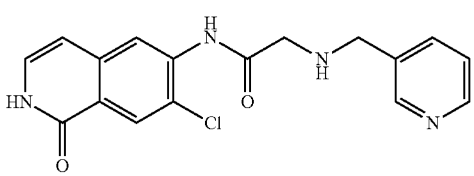 [SMILES: O=C(CNCc1cccnc1)Nc1cc2cc[nH]c(=O)c2cc1Cl] | N-(7-Chloro-1-oxo-1,2-dihydro-isoquinolin-6-yl)-2-[(pyridin-3-ylmethyl)-amino]-acetamide |
| 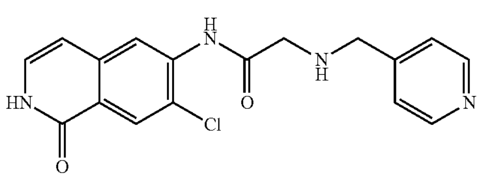 [SMILES: O=C(CNCc1ccncc1)Nc1cc2cc[nH]c(=O)c2cc1Cl] | N-(7-Chloro-1-oxo-1,2-dihydro-isoquinolin-6-yl)-2-[(pyridin-4-ylmethyl)-amino]-acetamide |

| Structure | Name |
|---|---|
| 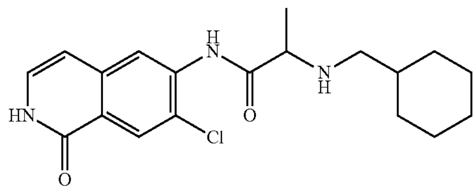 [SMILES: CC(NCC1CCCCC1)C(=O)Nc1cc2cc[nH]c(=O)c2cc1Cl] | N-(7-Chloro-1-oxo-1,2-dihydro-isoquinolin-6-yl)-2-(cyclohexylmethyl-amino)-propionamide |
| 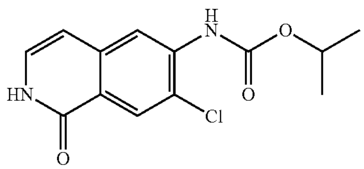 [SMILES: CC(C)OC(=O)Nc1cc2cc[nH]c(=O)c2cc1Cl] | (7-Chloro-1-oxo-1,2-dihydro-isoquinolin-6-yl)-carbamic acid isopropyl ester |
| 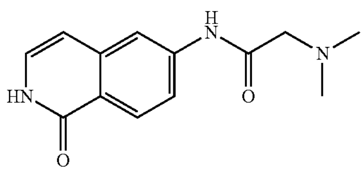 [SMILES: CN(C)CC(=O)Nc1ccc2c(=O)[nH]ccc2c1] | 2-Dimethylamino-N-(1-oxo-1,2-dihydro-isoquinolin-6-yl)-acetamide |
| 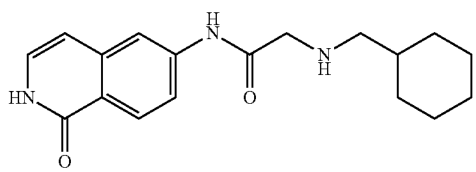 [SMILES: O=C(CNCC1CCCCC1)Nc1ccc2c(=O)[nH]ccc2c1] | 2-(Cyclohexylmethyl-amino)-N-(1-oxo-1,2-dihydro-isoquinolin-6-yl)-acetamide |
| 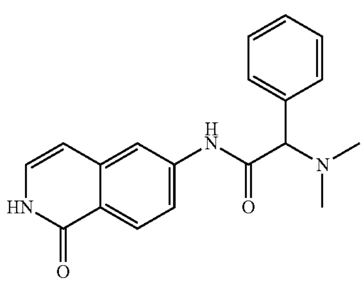 [SMILES: CN(C)C(C(=O)Nc1ccc2c(=O)[nH]ccc2c1)c1ccccc1] | 2-Dimethylamino-N-(1-oxo-1,2-dihydro-isoquinolin-6-yl)-2-phenyl-acetamide |
| 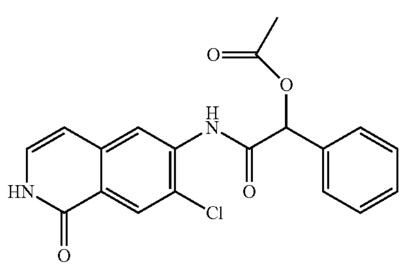 [SMILES: CC(=O)OC(C(=O)Nc1cc2cc[nH]c(=O)c2cc1Cl)c1ccccc1] | Acetic acid (7-chloro-1-oxo-1,2-dihydro-isoquinolin-6-ylcarbamoyl)-phenyl-methyl ester |
| 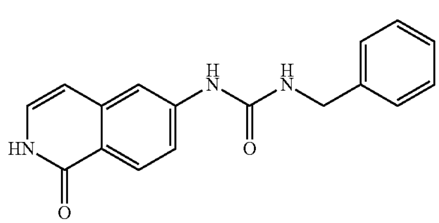 [SMILES: O=C(NCc1ccccc1)Nc1ccc2c(=O)[nH]ccc2c1] | 1-Benzyl-3-(1-oxo-1,2-dihydro-isoquinolin-6-yl)-urea |

| Structure | Name |
|---|---|
| 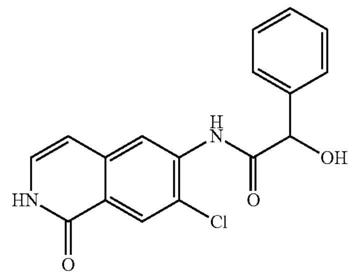 [SMILES: O=C(Nc1cc2cc[nH]c(=O)c2cc1Cl)C(O)c1ccccc1] | N-(7-Chloro-1-oxo-1,2-dihydro-isoquinolin-6-yl)-2-hydroxy-2-phenyl-acetamide |
| 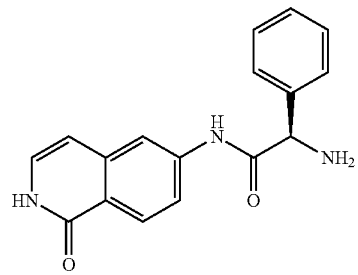 [SMILES: N[C@@H](C(=O)Nc1ccc2c(=O)[nH]ccc2c1)c1ccccc1] | (R)-2-Amino-N-(1-oxo-1,2-dihydro-isoquinolin-6-yl)-2-phenyl-acetamide |
| 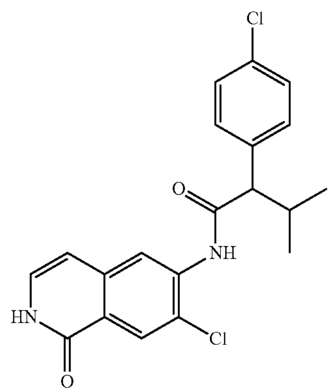 [SMILES: CC(C)C(C(=O)Nc1cc2cc[nH]c(=O)c2cc1Cl)c1ccc(Cl)cc1] | N-(7-Chloro-1-oxo-1,2-dihydro-isoquinolin-6-yl)-2-(4-chloro-phenyl)-3-methyl-butyramide |
| 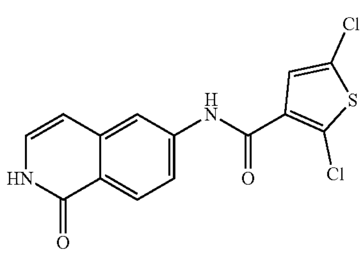 [SMILES: O=C(Nc1ccc2c(=O)[nH]ccc2c1)c1cc(Cl)sc1Cl] | 2,5-Dichloro-thiophene-3-carboxylic acid (1-oxo-1,2-dihydro-isoquinolin-6-yl)-amide |
| 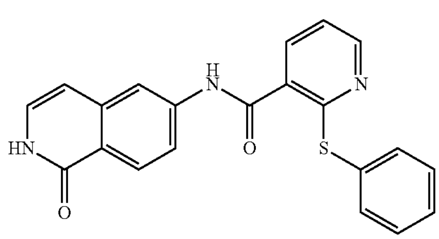 [SMILES: O=C(Nc1ccc2c(=O)[nH]ccc2c1)c1cccnc1Sc1ccccc1] | N-(1-Oxo-1,2-dihydro-isoquinolin-6-yl)-2-phenylsulfanyl-nicotinamide |
| 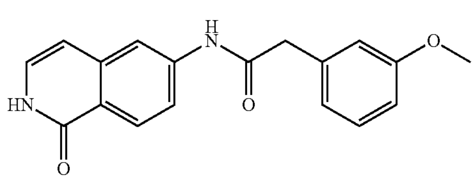 [SMILES: COc1cccc(CC(=O)Nc2ccc3c(=O)[nH]ccc3c2)c1] | 2-(3-Methoxy-phenyl)-N-(1-oxo-1,2-dihydro-isoquinolin-6-yl)-acetamide |

-continued

| Structure | Name |
|---|---|
| 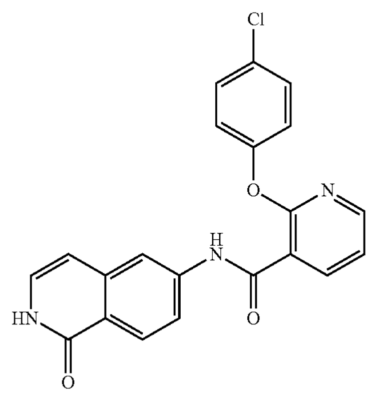 [SMILES: O=C(Nc1ccc2c(=O)[nH]ccc2c1)c1cccnc1Oc1ccc(Cl)cc1] | 2-(4-Chloro-phenoxy)-N-(1-oxo-1,2-dihydro-isoquinolin-6-yl)-nicotinamide |
| 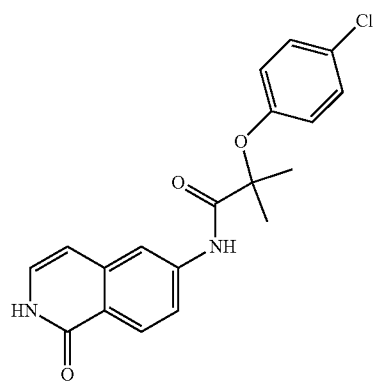 [SMILES: CC(C)(Oc1ccc(Cl)cc1)C(=O)Nc1ccc2c(=O)[nH]ccc2c1] | 2-(4-Chloro-phenoxy)-2-methyl-N-(1-oxo-1,2-dihydro-isoquinolin-6-yl)-propionamide |
| 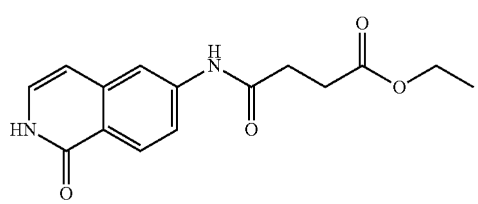 [SMILES: CCOC(=O)CCC(=O)Nc1ccc2c(=O)[nH]ccc2c1] | N-(1-Oxo-1,2-dihydro-isoquinolin-6-yl)-succinamic acid ethyl ester |
| 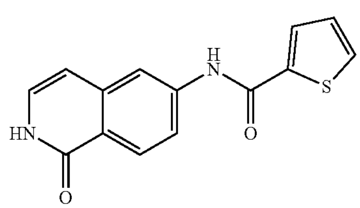 [SMILES: O=C(Nc1ccc2c(=O)[nH]ccc2c1)c1cccs1] | Thiophene-2-carboxylic acid (1-oxo-1,2-dihydro-isoquinolin-6-yl)-amide |
| 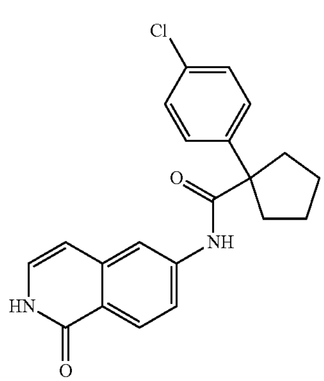 [SMILES: O=C(Nc1ccc2c(=O)[nH]ccc2c1)C1(c2ccc(Cl)cc2)CCCC1] | 1-(4-Chloro-phenyl)-cyclopentanecarboxylic acid (1-oxo-1,2-dihydro-isoquinolin-6-yl)-amide |

-continued

| Structure | Name |
|---|---|
| 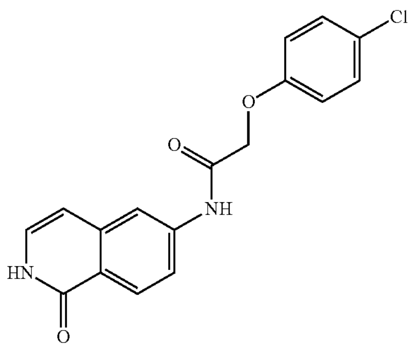 [SMILES: O=C(COc1ccc(Cl)cc1)Nc1ccc2c(=O)[nH]ccc2c1] | 2-(4-Chloro-phenoxy)-N-(1-oxo-1,2-dihydro-isoquinolin-6-yl)-acetamide |
| 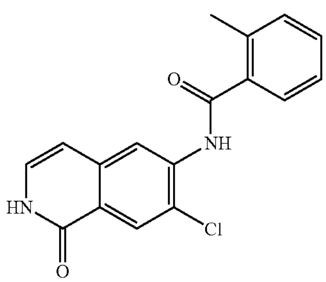 [SMILES: Cc1ccccc1C(=O)Nc1cc2cc[nH]c(=O)c2cc1Cl] | N-(7-Chloro-1-oxo-1,2-dihydro-isoquinolin-6-yl)-2-methyl-benzamide |
| 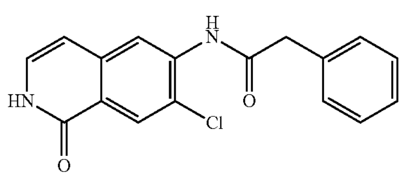 [SMILES: O=C(Cc1ccccc1)Nc1cc2cc[nH]c(=O)c2cc1Cl] | N-(7-Chloro-1-oxo-1,2-dihydro-isoquinolin-6-yl)-2-phenyl-acetamide |
| 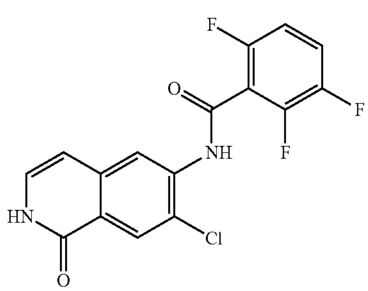 [SMILES: O=C(Nc1cc2cc[nH]c(=O)c2cc1Cl)c1c(F)ccc(F)c1F] | N-(7-Chloro-1-oxo-1,2-dihydro-isoquinolin-6-yl)-2,3,6-trifluoro-benzamide |
| 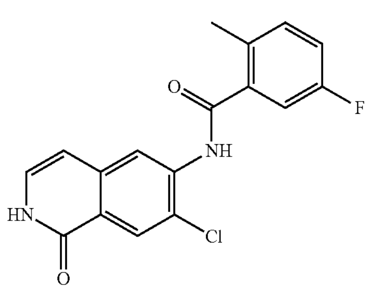 [SMILES: Cc1ccc(F)cc1C(=O)Nc1cc2cc[nH]c(=O)c2cc1Cl] | N-(7-Chloro-1-oxo-1,2-dihydro-isoquinolin-6-yl)-5-fluoro-2-methyl-benzamide |

| Structure | Name |
|---|---|
| 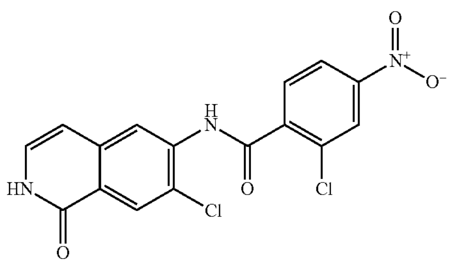 [SMILES: O=C(Nc1cc2cc[nH]c(=O)c2cc1Cl)c1ccc([N+](=O)[O-])cc1Cl] | 2-Chloro-N-(7-chloro-1-oxo-1,2-dihydro-isoquinolin-6-yl)-4-nitro-benzamide |
| 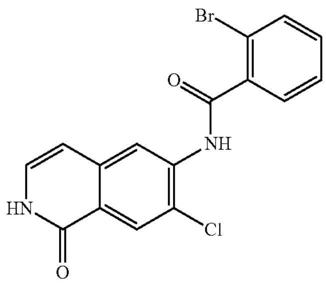 [SMILES: O=C(Nc1cc2cc[nH]c(=O)c2cc1Cl)c1ccccc1Br] | 2-Bromo-N-(7-chloro-1-oxo-1,2-dihydro-isoquinolin-6-yl)-benzamide |
| 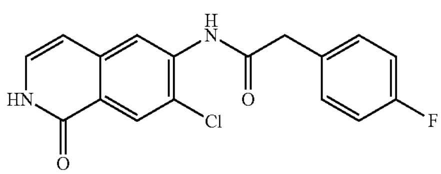 [SMILES: O=C(Cc1ccc(F)cc1)Nc1cc2cc[nH]c(=O)c2cc1Cl] | N-(7-Chloro-1-oxo-1,2-dihydro-isoquinolin-6-yl)-2-(4-fluoro-phenyl)-acetamide |
| 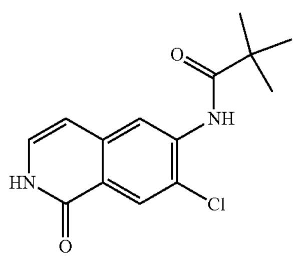 [SMILES: CC(C)(C)C(=O)Nc1cc2cc[nH]c(=O)c2cc1Cl] | N-(7-Chloro-1-oxo-1,2-dihydro-isoquinolin-6-yl)-2,2-dimethyl-propionamide |
| 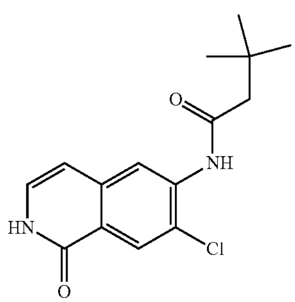 [SMILES: CC(C)(C)CC(=O)Nc1cc2cc[nH]c(=O)c2cc1Cl] | N-(7-Chloro-1-oxo-1,2-dihydro-isoquinolin-6-yl)-3,3-dimethyl-butyramide |
| 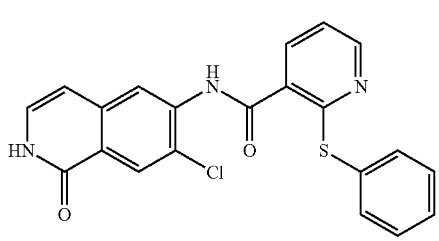 [SMILES: O=C(Nc1cc2cc[nH]c(=O)c2cc1Cl)c1cccnc1Sc1ccccc1] | N-(7-Chloro-1-oxo-1,2-dihydro-isoquinolin-6-yl)-2-phenylsulfanyl-nicotinamide |

| Structure | Name |
|---|---|
| 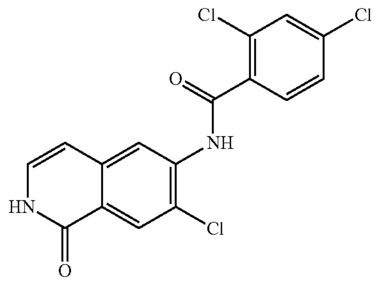 [SMILES: O=C(Nc1cc2cc[nH]c(=O)c2cc1Cl)c1ccc(Cl)cc1Cl] | 2,4-Dichloro-N-(7-chloro-1-oxo-1,2-dihydro-isoquinolin-6-yl)-benzamide |
| 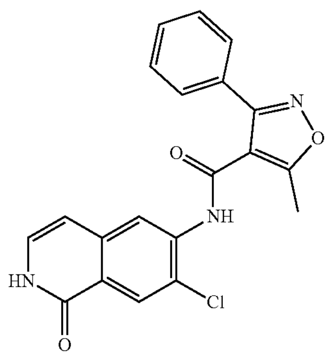 [SMILES: Cc1onc(-c2ccccc2)c1C(=O)Nc1cc2cc[nH]c(=O)c2cc1Cl] | 5-Methyl-3-phenyl-isoxazole-4-carboxylic acid (7-chloro-1-oxo-1,2-dihydro-isoquinolin-6-yl)-amide |
| 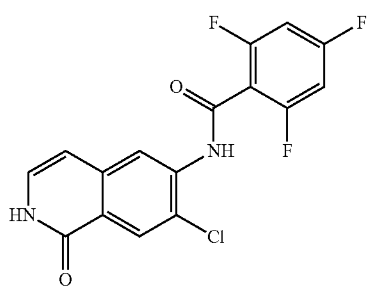 [SMILES: O=C(Nc1cc2cc[nH]c(=O)c2cc1Cl)c1c(F)cc(F)cc1F] | N-(7-Chloro-1-oxo-1,2-dihydro-isoquinolin-6-yl)-2,4,6-trifluoro-benzamide |
| 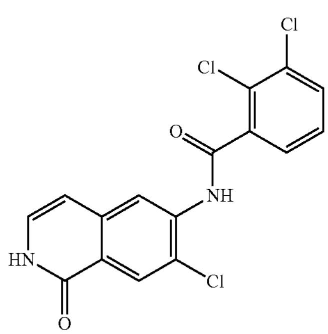 [SMILES: O=C(Nc1cc2cc[nH]c(=O)c2cc1Cl)c1cccc(Cl)c1Cl] | 2,3-Dichloro-N-(7-chloro-1-oxo-1,2-dihydro-isoquinolin-6-yl)-benzamide |
| 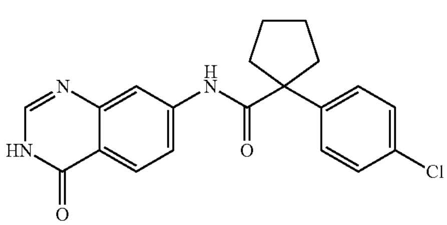 [SMILES: O=C(Nc1ccc2c(=O)[nH]cnc2c1)C1(c2ccc(Cl)cc2)CCCC1] | 1-(4-Chloro-phenyl)-cyclopentanecarboxylic acid (4-oxo-3,4-dihydro-quinazolin-7-yl)-amide |

| Structure | Name |
|---|---|
| 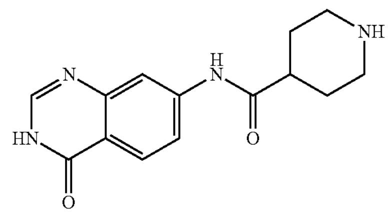 [SMILES: O=C(Nc1ccc2c(=O)[nH]cnc2c1)C1CCNCC1] | Piperidine-4-carboxylic acid (4-oxo-3,4-dihydro-quinazolin-7-yl)-amide |
| 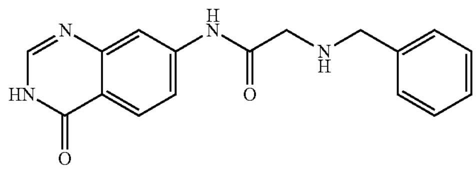 [SMILES: O=C(CNCc1ccccc1)Nc1ccc2c(=O)[nH]cnc2c1] | 2-Benzylamino-N-(4-oxo-3,4-dihydro-quinazolin-7-yl)-acetamide |
| 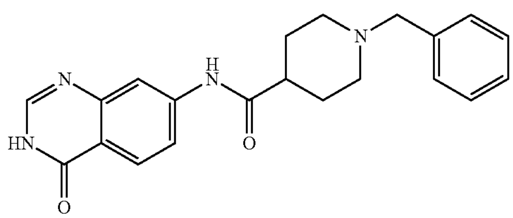 [SMILES: O=C(Nc1ccc2c(=O)[nH]cnc2c1)C1CCN(Cc2ccccc2)CC1] | 1-Benzyl-piperidine-4-carboxylic acid (4-oxo-3,4-dihydro-quinazolin-7-yl)-amide |
| 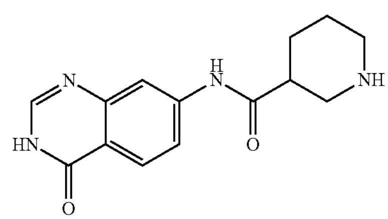 [SMILES: O=C(Nc1ccc2c(=O)[nH]cnc2c1)C1CCCNC1] | Piperidine-3-carboxylic acid (4-oxo-3,4-dihydro-quinazolin-7-yl)-amide |
| 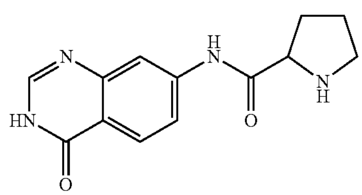 [SMILES: O=C(Nc1ccc2c(=O)[nH]cnc2c1)C1CCCN1] | Pyrrolidine-2-carboxylic acid (4-oxo-3,4-dihydro-quinazolin-7-yl)-amide |
| 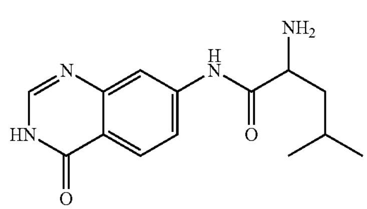 [SMILES: CC(C)CC(N)C(=O)Nc1ccc2c(=O)[nH]cnc2c1] | 2-Amino-4-methyl-pentanoic acid (4-oxo-3,4-dihydro-quinazolin-7-yl)-amide |
| 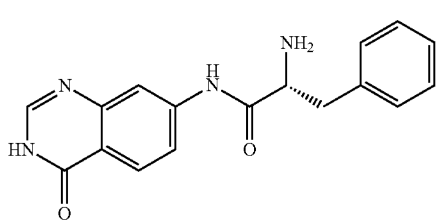 [SMILES: N[C@H](Cc1ccccc1)C(=O)Nc1ccc2c(=O)[nH]cnc2c1] | (R)-2-Amino-N-(4-oxo-3,4-dihydro-quinazolin-7-yl)-3-phenyl-propionamide |

| Structure | Name |
|---|---|
| 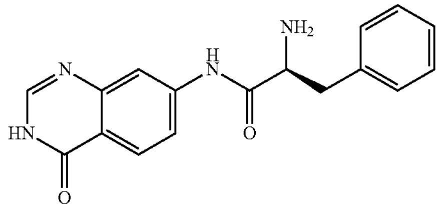 [SMILES: N[C@@H](Cc1ccccc1)C(=O)Nc1ccc2c(=O)[nH]cnc2c1] | (S)-2-Amino-N-(4-oxo-3,4-dihydro-quinazolin-7-yl)-3-phenyl-propionamide |
| 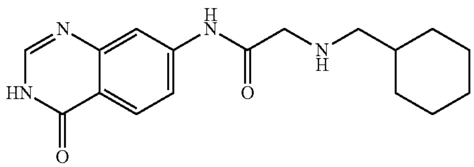 [SMILES: O=C(CNCC1CCCCC1)Nc1ccc2c(=O)[nH]cnc2c1] | 2-(Cyclohexylmethyl-amino)-N-(4-oxo-3,4-dihydro-isoquinolin-7-yl)-acetamide |
| 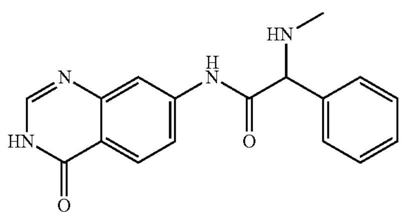 [SMILES: CNC(C(=O)Nc1ccc2c(=O)[nH]cnc2c1)c1ccccc1] | 2-Methylamino-N-(4-oxo-3,4-dihydro-quinazolin-7-yl)-2-phenyl-acetamide |
| 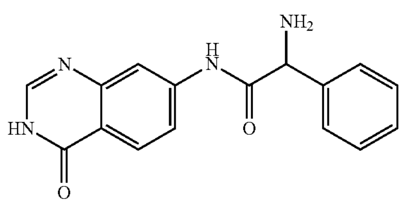 [SMILES: NC(C(=O)Nc1ccc2c(=O)[nH]cnc2c1)c1ccccc1] | 2-Amino-N-(4-oxo-3,4-dihydro-quinazolin-7-yl)-2-phenyl-acetamide |
| 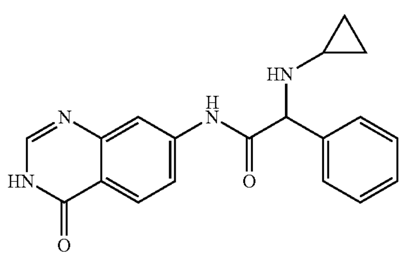 [SMILES: O=C(Nc1ccc2c(=O)[nH]cnc2c1)C(NC1CC1)c1ccccc1] | 2-Cyclopropylamino-N-(4-oxo-3,4-dihydro-quinazolin-7-yl)-2-phenyl-acetamide |
| 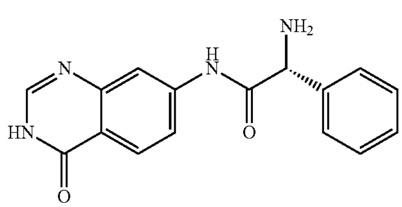 [SMILES: N[C@@H](C(=O)Nc1ccc2c(=O)[nH]cnc2c1)c1ccccc1] | (R)-2-Amino-N-(4-oxo-3,4-dihydro-quinazolin-7-yl)-2-phenyl-acetamide |
| 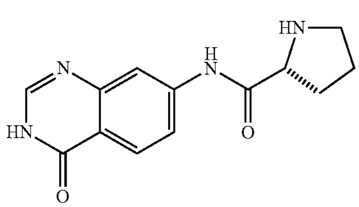 [SMILES: O=C(Nc1ccc2c(=O)[nH]cnc2c1)[C@H]1CCCN1] | (R)-Pyrrolidine-2-carboxylic acid (4-oxo-3,4-dihydro-quinazolin-7-yl)-amide |

-continued

| Structure | Name |
|---|---|
| 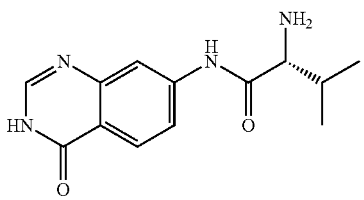 [SMILES: CC(C)[C@@H](N)C(=O)Nc1ccc2c(=O)[nH]cnc2c1] | (R)-2-Amino-3-methyl-N-(4-oxo-3,4-dihydro-quinazolin-7-yl)-butyramide |
| 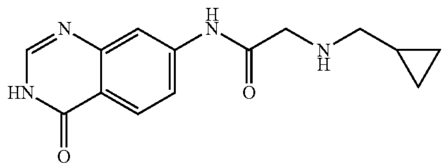 [SMILES: O=C(CNCC1CC1)Nc1ccc2c(=O)[nH]cnc2c1] | 2-(Cyclopropylmethyl-amino)-N-(4-oxo-3,4-dihydro-quinazolin-7-yl)-acetamide |
| 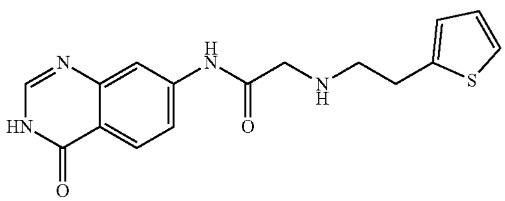 [SMILES: O=C(CNCCc1cccs1)Nc1ccc2c(=O)[nH]cnc2c1] | N-(4-Oxo-3,4-dihydro-quinazolin-7-yl)-2-(2-thiophen-2-yl-ethylamino)-acetamide |
| 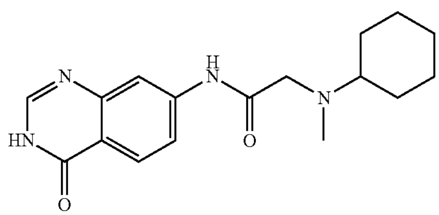 [SMILES: CN(CC(=O)Nc1ccc2c(=O)[nH]cnc2c1)C1CCCCC1] | 2-(Cyclohexyl-methyl-amino)-N-(4-oxo-3,4-dihydro-quinazolin-7-yl)-acetamide |
| 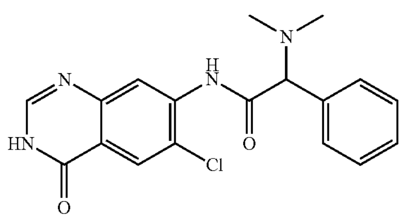 [SMILES: CN(C)C(C(=O)Nc1cc2nc[nH]c(=O)c2cc1Cl)c1ccccc1] | N-(6-Chloro-4-oxo-3,4-dihydro-quinazolin-7-yl)-2-dimethylamino-2-phenyl-acetamide |
| 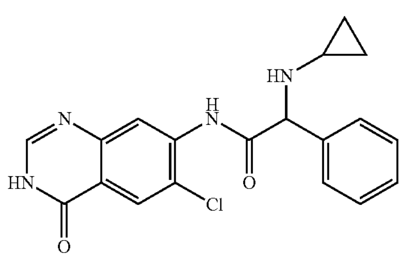 [SMILES: O=C(Nc1cc2nc[nH]c(=O)c2cc1Cl)C(NC1CC1)c1ccccc1] | N-(6-Chloro-4-oxo-3,4-dihydro-quinazolin-7-yl)-2-cyclopropylamino-2-phenyl-acetamide |
| 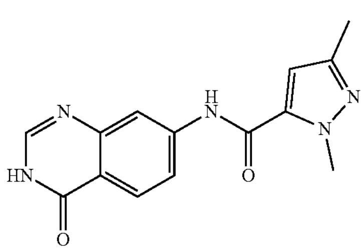 [SMILES: Cc1cc(C(=O)Nc2ccc3c(=O)[nH]cnc3c2)n(C)n1] | 2,5-Dimethyl-2H-pyrazole-3-carboxylic acid (4-oxo-3,4-dihydro-quinazolin-7-yl)-amide |

| Structure | Name |
|---|---|
| 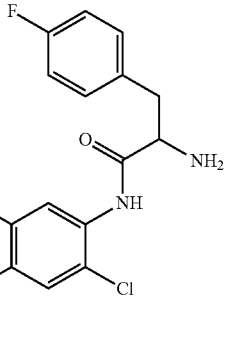 | 2-Amino-N-(7-chloro-1-oxo-1,2-dihydro-isoquinolin-6-yl)-3-(4-fluoro-phenyl)-propionamide |
| 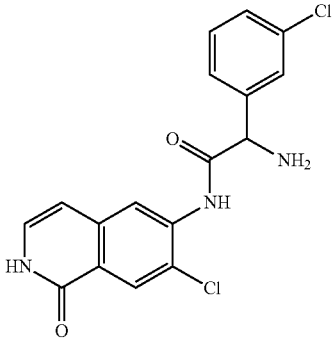 [SMILES: NC(C(=O)Nc1cc2cc[nH]c(=O)c2cc1Cl)c1cccc(Cl)c1] | 2-Amino-N-(7-chloro-1-oxo-1,2-dihydro-isoquinolin-6-yl)-2-(3-chloro-phenyl)-acetamide |
| 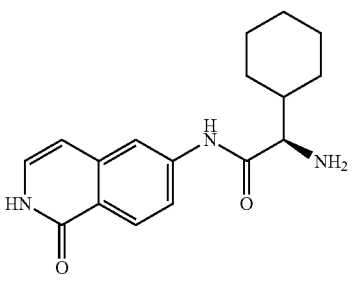 [SMILES: N[C@@H](C(=O)Nc1ccc2c(=O)[nH]ccc2c1)C1CCCCC1] | (R)-2-Amino-2-cyclohexyl-N-(1-oxo-1,2-dihydro-isoquinolin-6-yl)-acetamide |
| 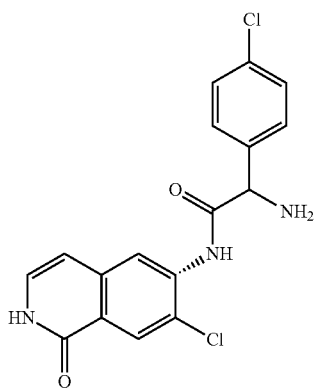 | (R)-2-Amino-2-(4-chloro-phenyl)-N-(1-oxo-1,2-dihydro-isoquinolin-6-yl)-acetamide |

| Structure | Name |
|---|---|
| 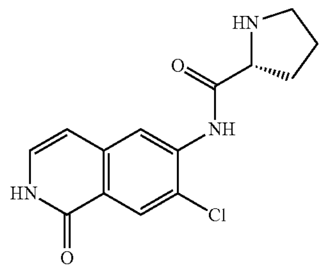 [SMILES: O=C(Nc1cc2cc[nH]c(=O)c2cc1Cl)[C@H]1CCCN1] | R)-Pyrrolidine-2-carboxylic acid (7-chloro-1-oxo-1,2-dihydro-isoquinolin-6-yl)-amide |
| 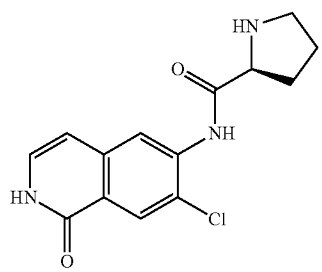 [SMILES: O=C(Nc1cc2cc[nH]c(=O)c2cc1Cl)[C@@H]1CCCN1] | (S)-Pyrrolidine-2-carboxylic acid (7-chloro-1-oxo-1,2-dihydro-isoquinolin-6-yl)-amide |
| 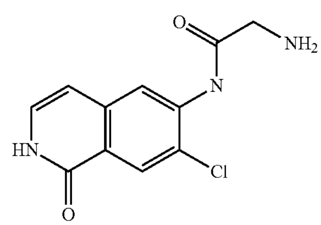 [SMILES: NCC(=O)Nc1cc2cc[nH]c(=O)c2cc1Cl] | 2-Amino-N-(7-chloro-1-oxo-1,2-dihydro-isoquinolin-6-yl)-acetamide |
| 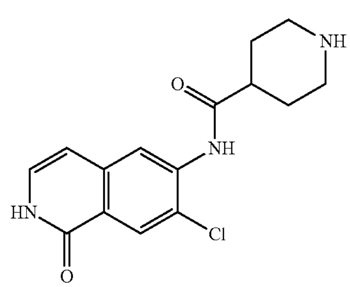 [SMILES: O=C(Nc1cc2cc[nH]c(=O)c2cc1Cl)C1CCNCC1] | Piperidine-4-carboxylic acid (7-chloro-1-oxo-1,2-dihydro-isoquinolin-6-yl)-amide |
| 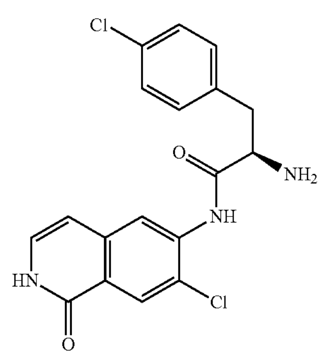 [SMILES: N[C@H](Cc1ccc(Cl)cc1)C(=O)Nc1cc2cc[nH]c(=O)c2cc1Cl] | (R)-2-Amino-N-(7-chloro-1-oxo-1,2-dihydro-isoquinolin-6-yl)-3-(4-chloro-phenyl)-propionamide |

| Structure | Name |
|---|---|
| 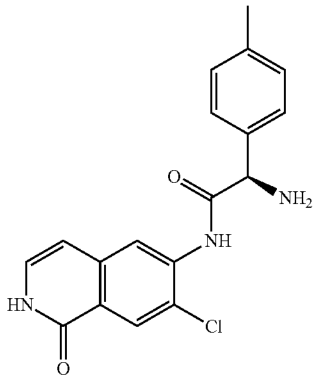 [SMILES: Cc1ccc([C@@H](N)C(=O)Nc2cc3cc[nH]c(=O)c3cc2Cl)cc1] | (R)-2-Amino-N-(7-chloro-1-oxo-1,2-dihydro-isoquinolin-6-yl)-2-p-tolyl-acetamide |
| 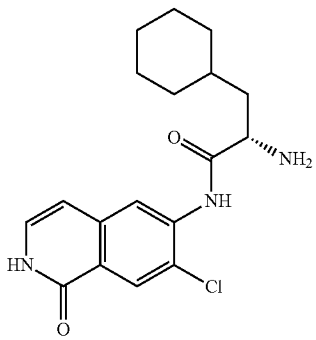 [SMILES: N[C@@H](CC1CCCCC1)C(=O)Nc1cc2cc[nH]c(=O)c2cc1Cl] | (S)-2-Amino-N-(7-chloro-1-oxo-1,2-dihydro-isoquinolin-6-yl)-3-cyclohexyl-propionamide |
| | (R)-2-Amino-N-(7-chloro-1-oxo-1,2-dihydro-isoquinolin-6-yl)-3-cyclohexyl-propionamide |
| 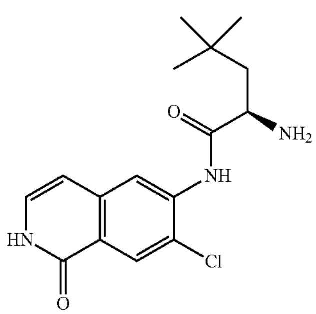 [SMILES: CC(C)(C)C[C@@H](N)C(=O)Nc1cc2cc[nH]c(=O)c2cc1Cl] | (R)-2-Amino-4,4-dimethyl-pentanoic acid (7-chloro-1-oxo-1,2-dihydro-isoquinolin-6-yl)-amide |

| Structure | Name |
|---|---|
| 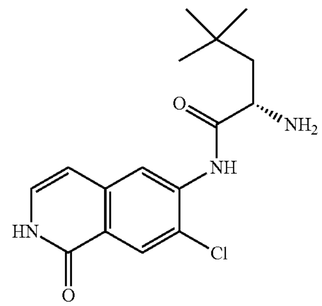 [SMILES: CC(C)(C)C[C@H](N)C(=O)Nc1cc2cc[nH]c(=O)c2cc1Cl] | (S)-2-Amino-4,4-dimethyl-pentanoic acid (7-chloro-1-oxo-1,2-dihydro-isoquinolin-6-yl)-amide |
| 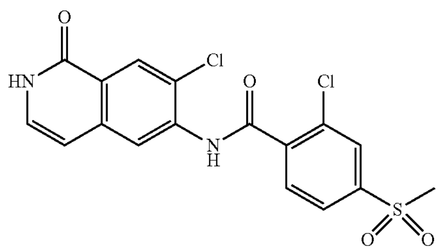 [SMILES: CS(=O)(=O)c1ccc(C(=O)Nc2cc3cc[nH]c(=O)c3cc2Cl)c(Cl)c1] | 2-Chloro-N-(7-chloro-1-oxo-1,2-dihydro-isoquinolin-6-yl)-4-methanesulfonyl-benzamide |
| 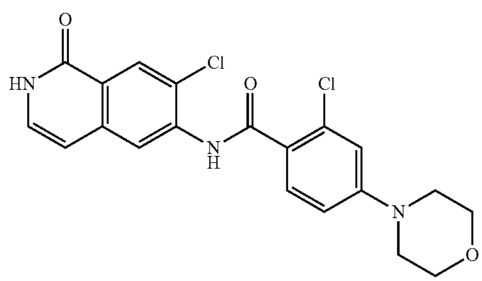 [SMILES: O=C(Nc1cc2cc[nH]c(=O)c2cc1Cl)c1ccc(N2CCOCC2)cc1Cl] | 2-Chloro-N-(7-chloro-1-oxo-1,2-dihydro-isoquinolin-6-yl)-4-morpholin-4-yl-benzamide |
| 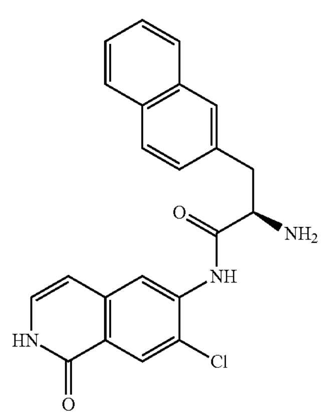 [SMILES: N[C@H](Cc1ccc2ccccc2c1)C(=O)Nc1cc2cc[nH]c(=O)c2cc1Cl] | (R)-2-Amino-N-(7-chloro-1-oxo-1,2-dihydro-isoquinolin-6-yl)-3-naphthalen-2-yl-propionamide |

| Structure | Name |
|---|---|
| 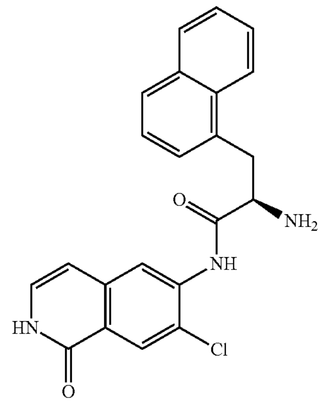 [SMILES: N[C@H](Cc1cccc2ccccc12)C(=O)Nc1cc2cc[nH]c(=O)c2cc1Cl] | (R)-2-Amino-N-(7-chloro-1-oxo-1,2-dihydro-isoquinolin-6-yl)-3-naphthalen-1-yl-propionamide |
| 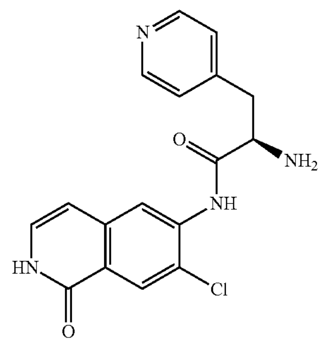 [SMILES: N[C@H](Cc1ccncc1)C(=O)Nc1cc2cc[nH]c(=O)c2cc1Cl] | (R)-2-Amino-N-(7-chloro-1-oxo-1,2-dihydro-isoquinolin-6-yl)-3-pyridin-4-yl-propionamide |
| 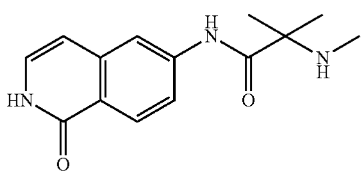 [SMILES: CNC(C)(C)C(=O)Nc1ccc2c(=O)[nH]ccc2c1] | 2-Methyl-2-methylamino-N-(1-oxo-1,2-dihydro-isoquinolin-6-yl)-propionamide |
| 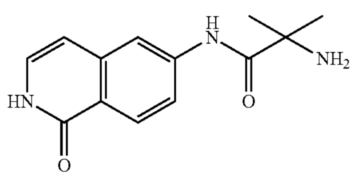 [SMILES: CC(C)(N)C(=O)Nc1ccc2c(=O)[nH]ccc2c1] | 2-Amino-2-methyl-N-(1-oxo-1,2-dihydro-isoquinolin-6-yl)-propionamide |
| 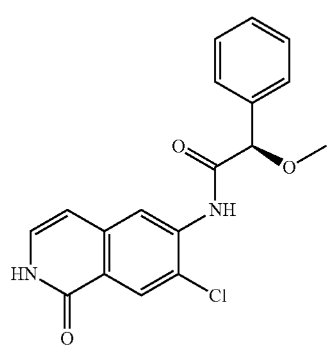 [SMILES: CO[C@@H](C(=O)Nc1cc2cc[nH]c(=O)c2cc1Cl)c1ccccc1] | (R)-N-(7-Chloro-1-oxo-1,2-dihydro-isoquinolin-6-yl)-2-methoxy-2-phenoxy-acetamide |

-continued

| Structure | Name |
|---|---|
| 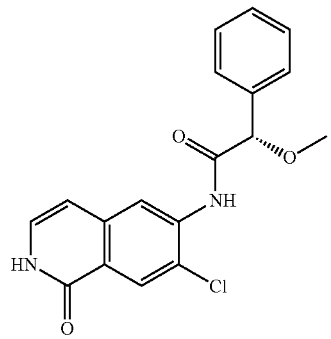 [SMILES: CO[C@H](C(=O)Nc1cc2cc[nH]c(=O)c2cc1Cl)c1ccccc1] | (S)-N-(7-Chloro-1-oxo-1,2-dihydro-isoquinolin-6-yl)-2-methoxy-2-phenyl-acetamide |
| 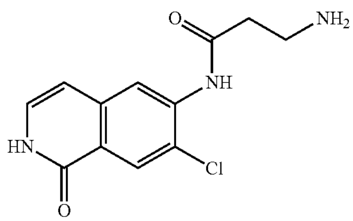 [SMILES: NCCC(=O)Nc1cc2cc[nH]c(=O)c2cc1Cl] | 3-Amino-N-(7-chloro-1-oxo-1,2-dihydro-isoquinolin-6-yl)-propionamide |
| 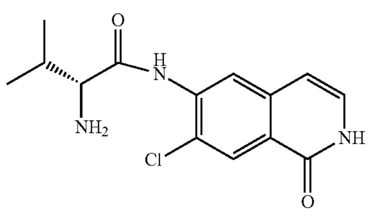 [SMILES: CC(C)[C@@H](N)C(=O)Nc1cc2cc[nH]c(=O)c2cc1Cl] | (R)-2-Amino-N-(7-chloro-1-oxo-1,2-dihydro-isoquinolin-6-yl)-3-methyl-butyramide |
| 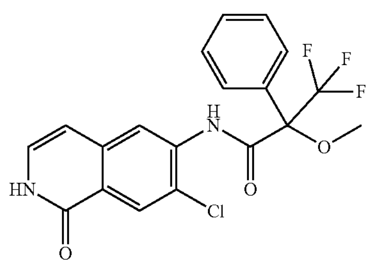 [SMILES: COC(C(=O)Nc1cc2cc[nH]c(=O)c2cc1Cl)(c1ccccc1)C(F)(F)F] | N-(7-Chloro-1-oxo-1,2-dihydro-isoquinolin-6-yl)-3,3,3-trifluoro-2-methoxy-2-phenyl-propionamide |
| 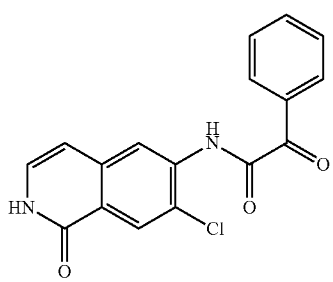 [SMILES: O=C(Nc1cc2cc[nH]c(=O)c2cc1Cl)C(=O)c1ccccc1] | N-(7-Chloro-1-oxo-1,2-dihydro-isoquinolin-6-yl)-2-oxo-2-phenyl-acetamide |
| 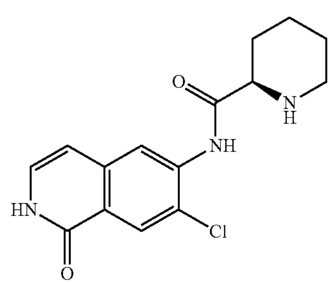 [SMILES: O=C(Nc1cc2cc[nH]c(=O)c2cc1Cl)[C@H]1CCCCN1] | (R)-Piperidine-2-carboxylic acid (7-chloro-1-oxo-1,2-dihydro-isoquinolin-6-yl)-amide |

-continued
| Structure | Name |
|---|---|
| 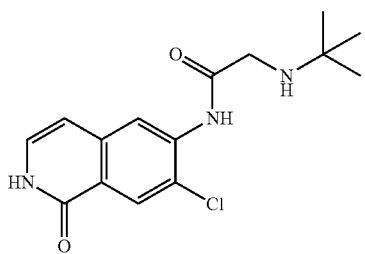 [SMILES: CC(C)(C)NCC(=O)Nc1cc2cc[nH]c(=O)c2cc1Cl] | 2-tert-Butylamino-N-(7-chloro-1-oxo-1,2-dihydro-isoquinolin-6-yl)-acetamide |
| 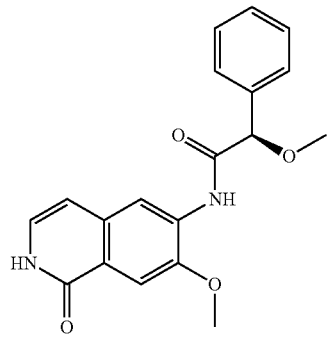 [SMILES: COc1cc2c(=O)[nH]ccc2cc1NC(=O)[C@H](OC)c1ccccc1] | (R)-2-Methoxy-N-(7-methoxy-1-oxo-1,2-dihydro-isoquinolin-6-yl)-2-phenyl-acetamide |
| 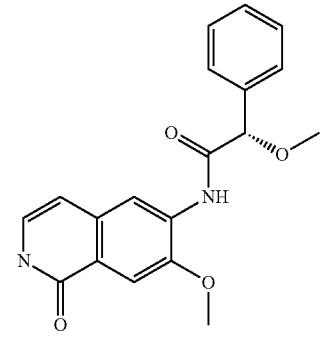 [SMILES: COc1cc2c(=O)[nH]ccc2cc1NC(=O)[C@@H](OC)c1ccccc1] | (S)-2-Methoxy-N-(7-methoxy-1-oxo-1,2-dihydro-isoquinolin-6-yl)-2-phenyl-acetamide |
| 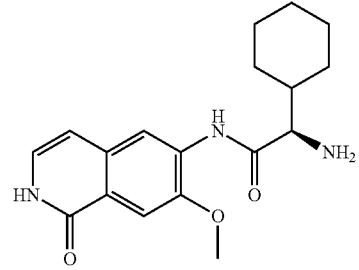 [SMILES: COc1cc2c(=O)[nH]ccc2cc1NC(=O)[C@H](N)C1CCCCC1] | (R)-2-Amino-2-cyclohexyl-N-(7-methoxy-1-oxo-1,2-dihydro-isoquinolin-6-yl)-acetamide |
| 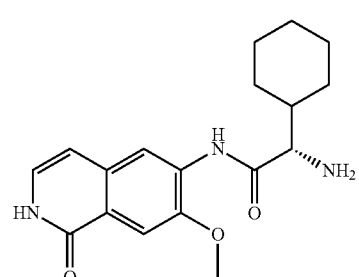 | (S)-2-Amino-2-cyclohexyl-N-(7-methoxy-1-oxo-1,2-dihydro-isoquinolin-6-yl)-acetamide |

| Structure | Name |
|---|---|
| 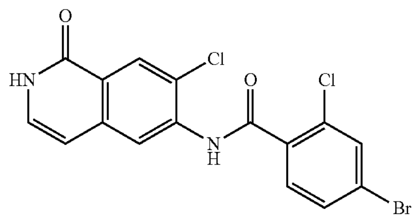 [SMILES: O=C(Nc1cc2cc[nH]c(=O)c2cc1Cl)c1ccc(Br)cc1Cl] | 4-Bromo-2-chloro-N-(7-chloro-1-oxo-1,2-dihydro-isoquinolin-6-yl)-benzamide |
| 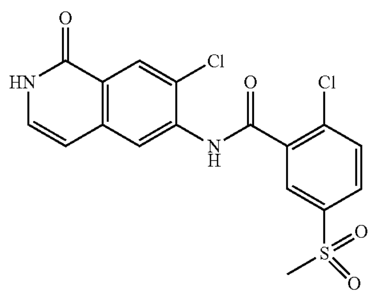 [SMILES: CS(=O)(=O)c1ccc(Cl)c(C(=O)Nc2cc3cc[nH]c(=O)c3cc2Cl)c1] | 2-Chloro-N-(7-chloro-1-oxo-1,2-dihydro-isoquinolin-6-yl)-6-methanesulfonyl-benzamide |
| 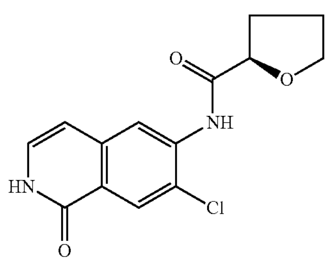 [SMILES: O=C(Nc1cc2cc[nH]c(=O)c2cc1Cl)[C@H]1CCCO1] | (R)-Tetrahydro-furan-2-carboxylic acid (7-chloro-1-oxo-1,2-dihydro-isoquinolin-6-yl)-amide |
| 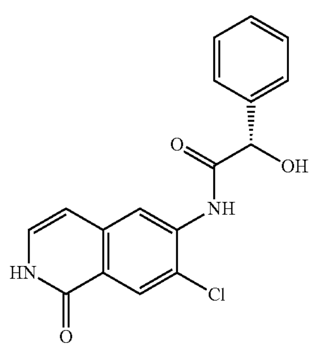 [SMILES: O=C(Nc1cc2cc[nH]c(=O)c2cc1Cl)[C@@H](O)c1ccccc1] | (S)-N-(7-Chloro-1-oxo-1,2-dihydro-isoquinolin-6-yl)-2-hydroxy-2-phenyl-acetamide |
| 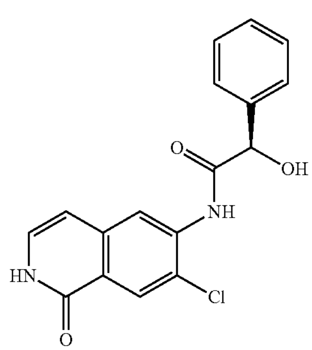 [SMILES: O=C(Nc1cc2cc[nH]c(=O)c2cc1Cl)[C@H](O)c1ccccc1] | (R)-N-(7-Chloro-1-oxo-1,2-dihydro-isoquinolin-6-yl)-2-hydroxy-2-phenyl-acetamide |

-continued

| Structure | Name |
|---|---|
| 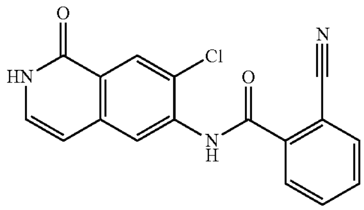 [SMILES: N#Cc1ccccc1C(=O)Nc1cc2cc[nH]c(=O)c2cc1Cl] | N-(7-Chloro-1-oxo-1,2-dihydro-isoquinolin-6-yl)-2-cyano-benzamide |
| 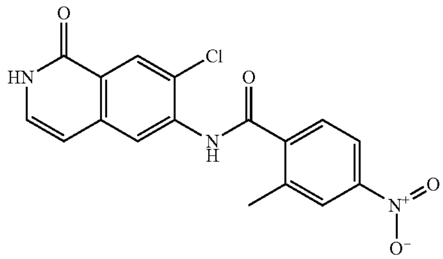 [SMILES: Cc1cc([N+](=O)[O-])ccc1C(=O)Nc1cc2cc[nH]c(=O)c2cc1Cl] | N-(7-Chloro-1-oxo-1,2-dihydro-isoquinolin-6-yl)-2-methyl-4-nitro-benzamide |
| 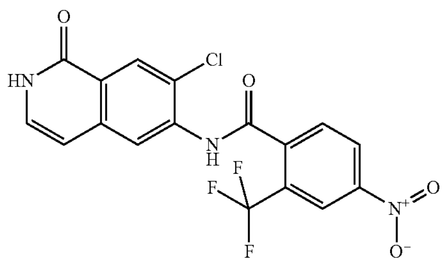 [SMILES: O=C(Nc1cc2cc[nH]c(=O)c2cc1Cl)c1ccc([N+](=O)[O-])cc1C(F)(F)F] | N-(7-Chloro-1-oxo-1,2-dihydro-isoquinolin-6-yl)-4-nitro-2-trifluoromethyl-benzamide |
| 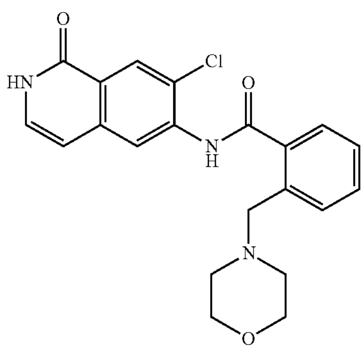 [SMILES: O=C(Nc1cc2cc[nH]c(=O)c2cc1Cl)c1ccccc1CN1CCOCC1] | N-(7-Chloro-1-oxo-1,2-dihydro-isoquinolin-6-yl)-2-morpholin-4-ylmethyl-benzamide |
| 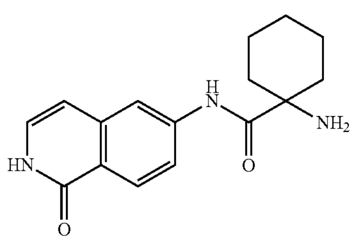 [SMILES: NC1(C(=O)Nc2ccc3c(=O)[nH]ccc3c2)CCCCC1] | 1-Amino-cyclohexanecarboxylic acid (1-oxo-1,2-dihydro-isoquinolin-6-yl)-amide |
| 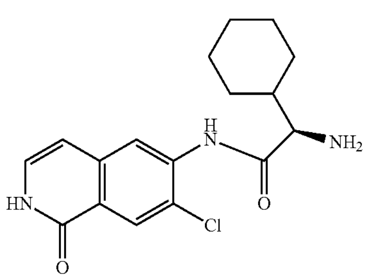 [SMILES: N[C@@H](C(=O)Nc1cc2cc[nH]c(=O)c2cc1Cl)C1CCCCC1] | (R)-2-Amino-N-(7-chloro-1-oxo-1,2-dihydro-isoquinolin-6-yl)-2-cyclohexyl-acetamide |

-continued

| Structure | Name |
|---|---|
| 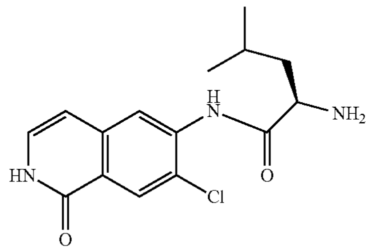 [SMILES: CC(C)C[C@@H](N)C(=O)Nc1cc2cc[nH]c(=O)c2cc1Cl] | (R)-2-Amino-4-methyl-pentanoic acid (7-chloro-1-oxo-1,2-dihydro-isoquinolin-6-yl)-amide |
| 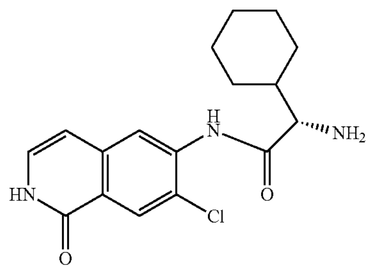 [SMILES: N[C@H](C(=O)Nc1cc2cc[nH]c(=O)c2cc1Cl)C1CCCCC1] | (S)-2-Amino-N-(7-chloro-1-oxo-1,2-dihydro-isoquinolin-6-yl)-2-cyclohexyl-acetamide |
| 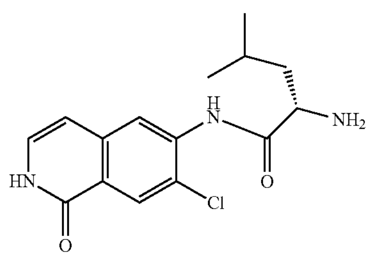 [SMILES: CC(C)C[C@H](N)C(=O)Nc1cc2cc[nH]c(=O)c2cc1Cl] | (S)-2-Amino-4-methyl-pentanoic acid (7-chloro-1-oxo-1,2-dihydro-isoquinolin-6-yl)-amide |
| 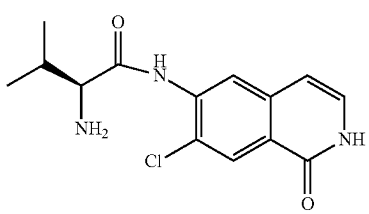 [SMILES: CC(C)[C@H](N)C(=O)Nc1cc2cc[nH]c(=O)c2cc1Cl] | (S)-2-Amino-N-(7-chloro-1-oxo-1,2-dihydro-isoquinolin-6-yl)-3-methyl-butyramide |
| 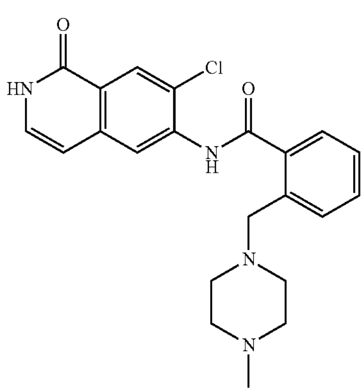 [SMILES: CN1CCN(Cc2ccccc2C(=O)Nc2cc3cc[nH]c(=O)c3cc2Cl)CC1] | N-(7-Chloro-1-oxo-1,2-dihydro-isoquinolin-6-yl)-2-(4-methyl-piperazin-1-ylmethyl)-benzamide |

| Structure | Name |
|---|---|
| 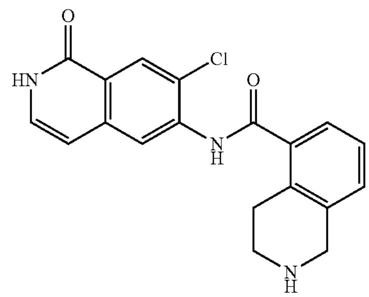 [SMILES: O=C(Nc1cc2cc[nH]c(=O)c2cc1Cl)c1cccc2c1CCNC2] | 1,2,3,4-Tetrahydro-isoquinoline-5-carboxylic acid (7-chloro-1-oxo-1,2-dihydro-isoquinolin-6-yl)-amide |
| 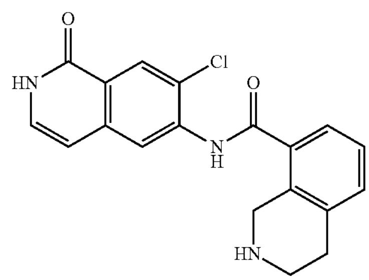 [SMILES: O=C(Nc1cc2cc[nH]c(=O)c2cc1Cl)c1cccc2c1CNCC2] | 1,2,3,4-Tetrahydro-isoquinoline-8-carboxylic acid (7-chloro-1-oxo-1,2-dihydro-isoquinolin-6-yl)-amide |
| 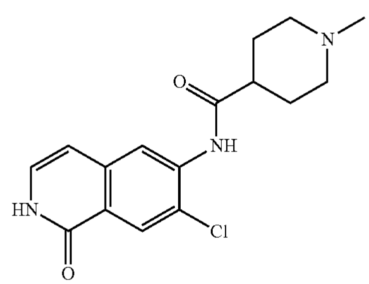 [SMILES: CN1CCC(C(=O)Nc2cc3cc[nH]c(=O)c3cc2Cl)CC1] | 1-Methyl-piperidine-4-carboxylic acid (7-chloro-1-oxo-1,2-dihydro-isoquinolin-6-yl)-amide |
| 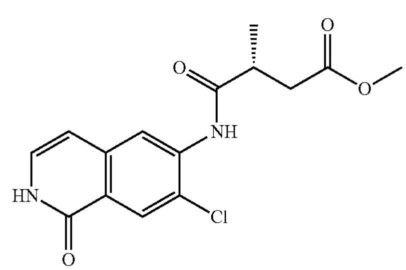 [SMILES: COC(=O)C[C@@H](C)C(=O)Nc1cc2cc[nH]c(=O)c2cc1Cl] | (R)-N-(7-Chloro-1-oxo-1,2-dihydro-isoquinolin-6-yl)-3-methyl-succinamic acid methyl ester |
| 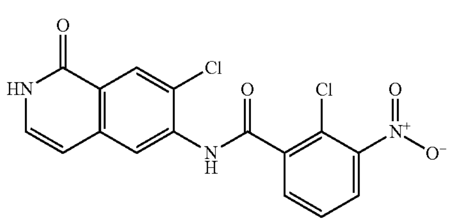 [SMILES: O=C(Nc1cc2cc[nH]c(=O)c2cc1Cl)c1cccc([N+](=O)[O-])c1Cl] | 2-Chloro-N-(7-chloro-1-oxo-1,2-dihydro-isoquinolin-6-yl)-3-nitro-benzamide |

| Structure | Name |
|---|---|
| 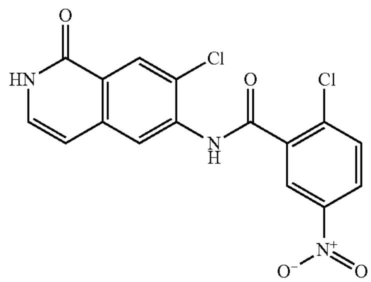 [SMILES: O=C(Nc1cc2cc[nH]c(=O)c2cc1Cl)c1cc([N+](=O)[O-])ccc1Cl] | 2-Chloro-N-(7-chloro-1-oxo-1,2-dihydro-isoquinolin-6-yl)-5-nitro-benzamide |
| 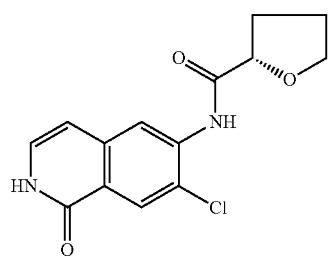 [SMILES: O=C(Nc1cc2cc[nH]c(=O)c2cc1Cl)[C@@H]1CCCO1] | (S)-Tetrahydro-furan-2-carboxylic acid (7-chloro-1-oxo-1,2-dihydro-isoquinolin-6-yl)-amide |
| 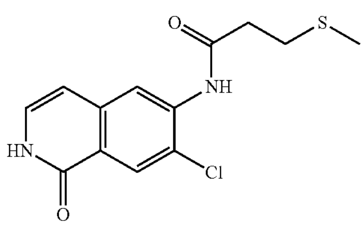 [SMILES: CSCCC(=O)Nc1cc2cc[nH]c(=O)c2cc1Cl] | N-(7-Chloro-1-oxo-1,2-dihydro-isoquinolin-6-yl)-3-methylsulfanyl-propionamide |
| 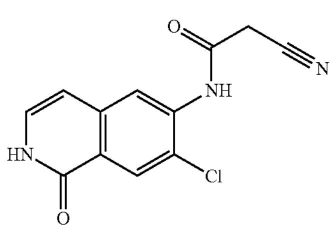 [SMILES: N#CCC(=O)Nc1cc2cc[nH]c(=O)c2cc1Cl] | N-(7-Chloro-1-oxo-1,2-dihydro-isoquinolin-6-yl)-2-cyano-acetamide |
| 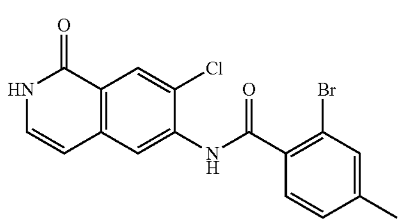 [SMILES: Cc1ccc(C(=O)Nc2cc3cc[nH]c(=O)c3cc2Cl)c(Br)c1] | 2-Bromo-N-(7-chloro-1-oxo-1,2-dihydro-isoquinolin-6-yl)-4-methyl-benzamide |
| 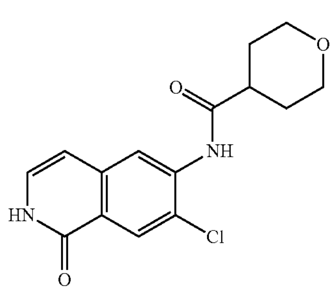 [SMILES: O=C(Nc1cc2cc[nH]c(=O)c2cc1Cl)C1CCOCC1] | Tetrahydro-pyran-4-carboxylic acid (7-chloro-1-oxo-1,2-dihydro-isoquinolin-6-yl)-amide |

-continued

| Structure | Name |
|---|---|
| 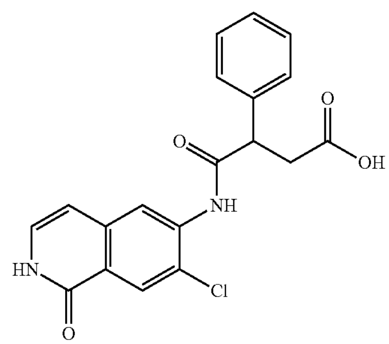 [SMILES: O=C(O)CC(C(=O)Nc1cc2cc[nH]c(=O)c2cc1Cl)c1ccccc1] | N-(7-Chloro-1-oxo-1,2-dihydro-isoquinolin-6-yl)-3-phenyl-succinamic acid |
| 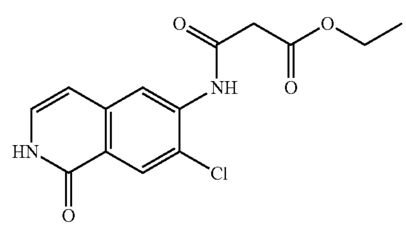 [SMILES: CCOC(=O)CC(=O)Nc1cc2cc[nH]c(=O)c2cc1Cl] | N-(7-Chloro-1-oxo-1,2-dihydro-isoquinolin-6-yl)-malonamic acid ethyl ester |
| 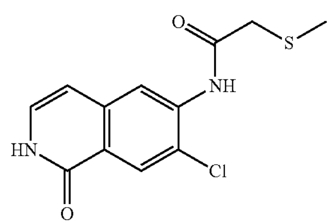 [SMILES: CSCC(=O)Nc1cc2cc[nH]c(=O)c2cc1Cl] | N-(7-Chloro-1-oxo-1,2-dihydro-isoquinolin-6-yl)-2-methylsulfanyl-acetamide |
| 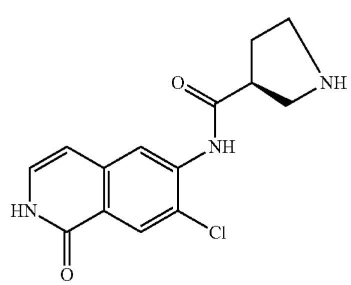 [SMILES: O=C(Nc1cc2cc[nH]c(=O)c2cc1Cl)[C@H]1CCNC1] | (S)-Pyrrolidine-3-carboxylic acid (7-chloro-1-oxo-1,2-dihydro-isoquinolin-6-yl)-amide |
| 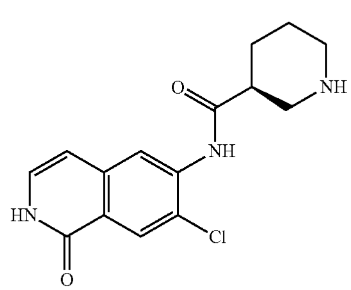 [SMILES: O=C(Nc1cc2cc[nH]c(=O)c2cc1Cl)[C@H]1CCCNC1] | (S)-Piperidine-3-carboxylic acid (7-chloro-1-oxo-1,2-dihydro-isoquinolin-6-yl)-amide |

-continued

| Structure | Name |
|---|---|
| 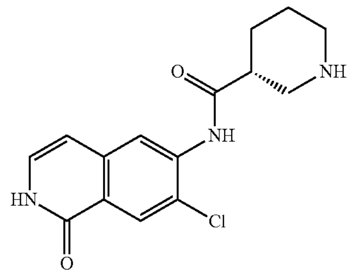 [SMILES: O=C(Nc1cc2cc[nH]c(=O)c2cc1Cl)[C@@H]1CCCNC1] | (R)-Piperidine-3-carboxylic acid (7-chloro-1-oxo-1,2-dihydro-isoquinolin-6-yl)-amide |
| 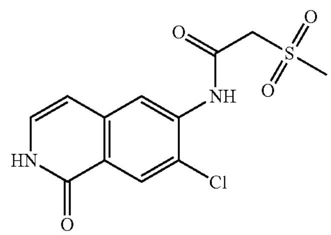 [SMILES: CS(=O)(=O)CC(=O)Nc1cc2cc[nH]c(=O)c2cc1Cl] | N-(7-Chloro-1-oxo-1,2-dihydro-isoquinolin-6-yl)-2-methanesulfonyl-acetamide |
| 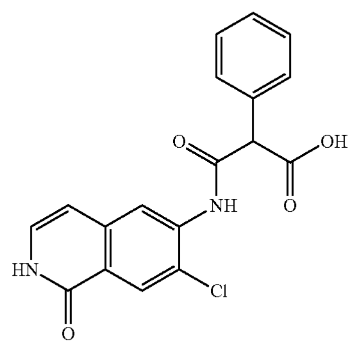 [SMILES: O=C(O)C(C(=O)Nc1cc2cc[nH]c(=O)c2cc1Cl)c1ccccc1] | N-(7-Chloro-1-oxo-1,2-dihydro-isoquinolin-6-yl)-2-phenyl-malonamic acid |
| 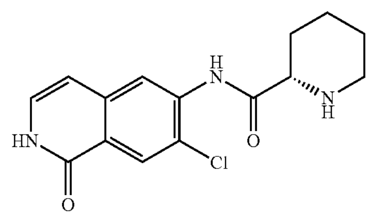 [SMILES: O=C(Nc1cc2cc[nH]c(=O)c2cc1Cl)[C@@H]1CCCCN1] | (S)-Piperidine-2-carboxylic acid (7-chloro-1-oxo-1,2-dihydro-isoquinolin-6-yl)-amide |
| 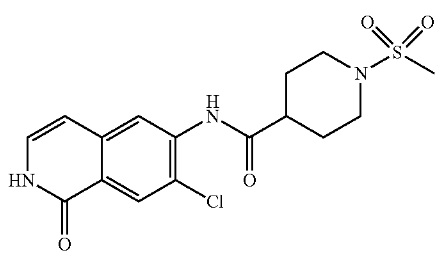 [SMILES: CS(=O)(=O)N1CCC(C(=O)Nc2cc3cc[nH]c(=O)c3cc2Cl)CC1] | 1-Methanesulfonyl-4-methyl-piperidine-4-carboxylic acid (7-chloro-1-oxo-1,2-dihydro-isoquinolin-6-yl)-amide |
| 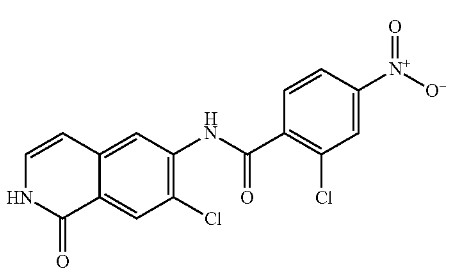 [SMILES: O=C(Nc1cc2cc[nH]c(=O)c2cc1Cl)c1ccc([N+](=O)[O-])cc1Cl] | 2-Chloro-N-(7-chloro-1-oxo-1,2-dihydro-isoquinolin-6-yl)-4-nitro-benzamide |

-continued

| Structure | Name |
|---|---|
| 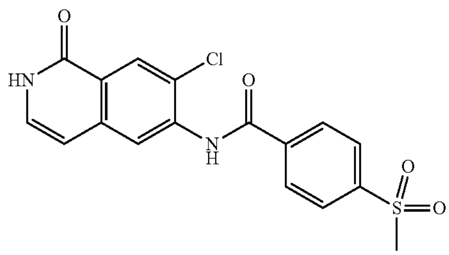 [SMILES: CS(=O)(=O)c1ccc(C(=O)Nc2cc3cc[nH]c(=O)c3cc2Cl)cc1] | N-(7-Chloro-1-oxo-1,2-dihydro-isoquinolin-6-yl)-4-methanesulfonyl-benzamide |
| 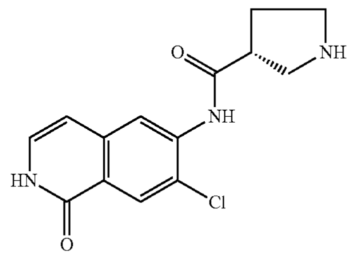 [SMILES: O=C(Nc1cc2cc[nH]c(=O)c2cc1Cl)[C@@H]1CCNC1] | (R)-Pyrrolidine-3-carboxylic acid (7-chloro-1-oxo-1,2-dihydro-isoquinolin-6-yl)-amide |
| | 4-Amino-cyclohexanecarboxylic acid (7-chloro-1-oxo-1,2-dihydro-isoquinolin-6-yl)-amide |
| | 4-Amino-cyclohexanecarboxylic acid (7-chloro-1-oxo-1,2-dihydro-isoquinolin-6-yl)-amide |
| 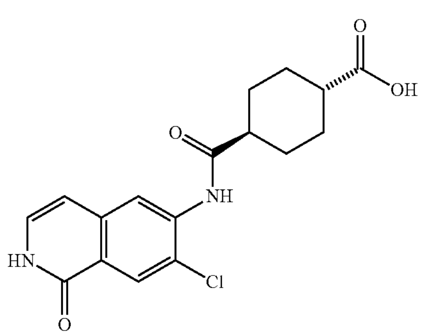 [SMILES: O=c1[nH]ccc2cc(NC(=O)[C@H]3CC[C@H](C(=O)O)CC3)c(Cl)cc12] | 4-(7-Chloro-1-oxo-1,2-dihydro-isoquinolin-6-ylcarbamoyl)-cyclohexanecarboxylic acid |

| Structure | Name |
|---|---|
| 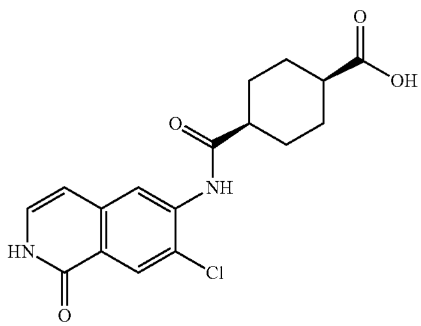 [SMILES: O=c1[nH]ccc2cc(NC(=O)[C@H]3CC[C@@H](C(=O)O)CC3)c(Cl)cc12] | 4-(7-Chloro-1-oxo-1,2-dihydro-isoquinolin-6-ylcarbamoyl)-cyclohexanecarboxylic acid |
| 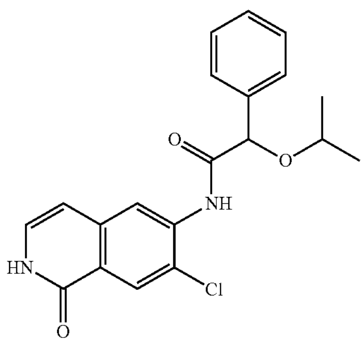 [SMILES: CC(C)OC(C(=O)Nc1cc2cc[nH]c(=O)c2cc1Cl)c1ccccc1] | (R)-N-(7-Chloro-1-oxo-1,2-dihydro-isoquinolin-6-yl)-2-isopropoxy-2-phenyl-acetamide |
| 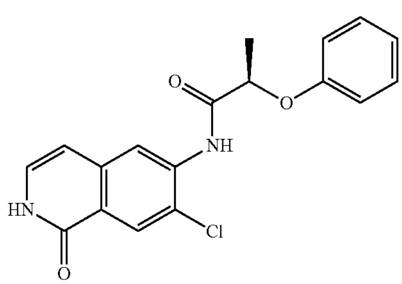 [SMILES: C[C@@H](Oc1ccccc1)C(=O)Nc1cc2cc[nH]c(=O)c2cc1Cl] | (R)-N-(7-Chloro-1-oxo-1,2-dihydro-isoquinolin-6-yl)-2-phenoxy-propionamide |
| 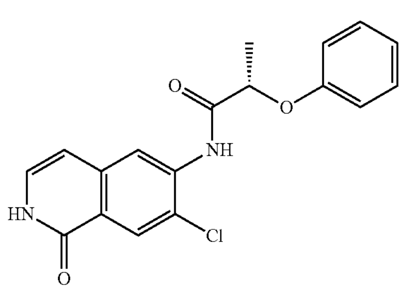 [SMILES: C[C@H](Oc1ccccc1)C(=O)Nc1cc2cc[nH]c(=O)c2cc1Cl] | (S)-N-(7-Chloro-1-oxo-1,2-dihydro-isoquinolin-6-yl)-2-phenoxy-propionamide |
| 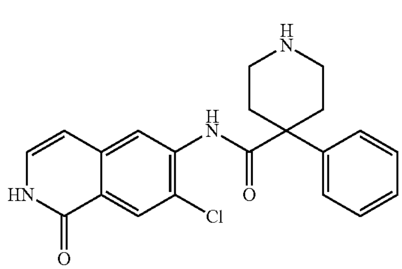 [SMILES: O=C(Nc1cc2cc[nH]c(=O)c2cc1Cl)C1(c2ccccc2)CCNCC1] | 4-Phenyl-piperidine-4-carboxylic acid (7-chloro-1-oxo-1,2-dihydro-isoquinolin-6-yl)-amide |

| Structure | Name |
|---|---|
| 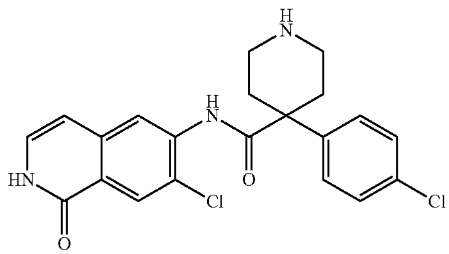 [SMILES: O=C(Nc1cc2cc[nH]c(=O)c2cc1Cl)C1(c2ccc(Cl)cc2)CCNCC1] | 4-(4-Chloro-phenyl)-piperidine-4-carboxylic acid (7-chloro-1-oxo-1,2-dihydro-isoquinolin-6-yl)-amide |
| 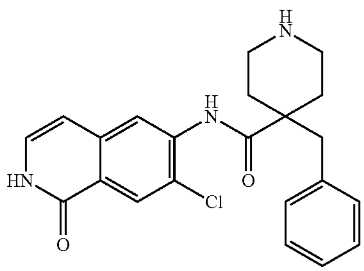 [SMILES: O=C(Nc1cc2cc[nH]c(=O)c2cc1Cl)C1(Cc2ccccc2)CCNCC1] | 4-Benzyl-piperidine-4-carboxylic acid (7-chloro-1-oxo-1,2-dihydro-isoquinolin-6-yl)-amide |
| 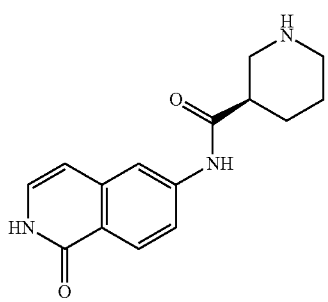 [SMILES: O=C(Nc1ccc2c(=O)[nH]ccc2c1)[C@@H]1CCCNC1] | (R)-Piperidine-3-carboxylic acid (1-oxo-1,2-dihydro-isoquinolin-6-yl)-amide |
| 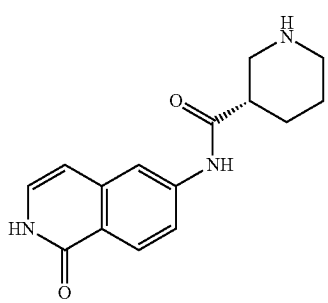 [SMILES: O=C(Nc1ccc2c(=O)[nH]ccc2c1)[C@H]1CCCNC1] | (S)-Piperidine-3-carboxylic acid (1-oxo-1,2-dihydro-isoquinolin-6-yl)-amide |
| 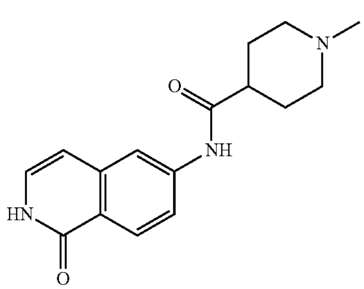 [SMILES: CN1CCC(C(=O)Nc2ccc3c(=O)[nH]ccc3c2)CC1] | 1-Methyl-piperidine-4-carboxylic acid (1-oxo-1,2-dihydro-isoquinolin-6-yl)-amide |

-continued

| Structure | Name |
|---|---|
| 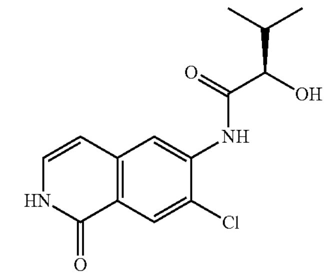 [SMILES: CC(C)[C@@H](O)C(=O)Nc1cc2cc[nH]c(=O)c2cc1Cl] | (R)-N-(7-Chloro-1-oxo-1,2-dihydro-isoquinolin-6-yl)-2-hydroxy-3-methyl-butyramide |
| 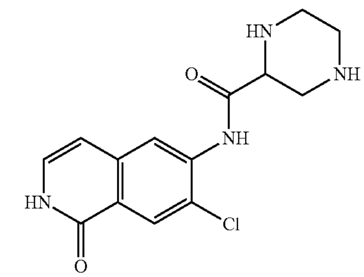 [SMILES: O=C(Nc1cc2cc[nH]c(=O)c2cc1Cl)C1CNCCN1] | Piperazine-2-carboxylic acid (7-chloro-1-oxo-1,2-dihydro-isoquinolin-6-yl)-amide |
| 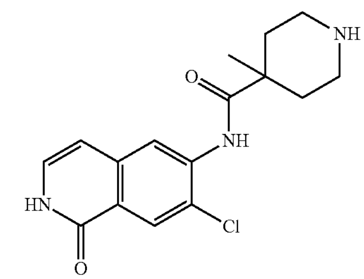 [SMILES: CC1(C(=O)Nc2cc3cc[nH]c(=O)c3cc2Cl)CCNCC1] | 4-Methyl-piperidine-4-carboxylic acid (7-chloro-1-oxo-1,2-dihydro-isoquinolin-6-yl)-amide |
| 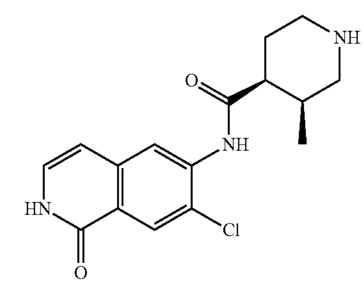 [SMILES: C[C@@H]1CNCC[C@@H]1C(=O)Nc1cc2cc[nH]c(=O)c2cc1Cl] | (3S,4S)-3-Methyl-piperidine-4-carboxylic acid (7-chloro-1-oxo-1,2-dihydro-isoquinolin-6-yl)-amide |
| 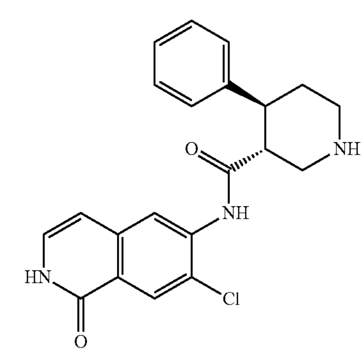 [SMILES: O=C(Nc1cc2cc[nH]c(=O)c2cc1Cl)[C@H]1CNCC[C@@H]1c1ccccc1] | (trans)-4-Phenyl-piperidine-3-carboxylic acid (7-chloro-1-oxo-1,2-dihydro-isoquinolin-6-yl)-amide |

| Structure | Name |
|---|---|
| 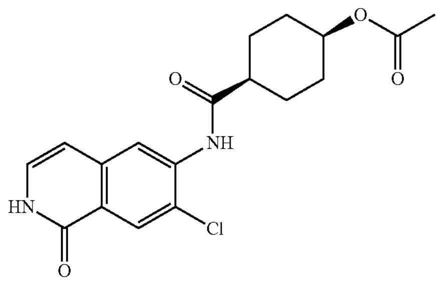 [SMILES: CC(=O)O[C@H]1CC[C@@H](C(=O)Nc2cc3cc[nH]c(=O)c3cc2Cl)CC1] | Acetic acid 4-(7-chloro-1-oxo-1,2-dihydro-isoquinolin-6-ylcarbamoyl)-cyclohexyl ester |
| 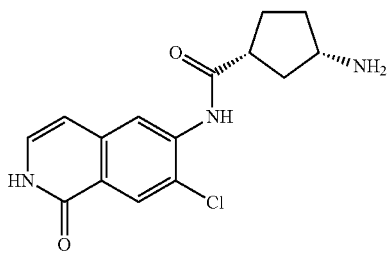 [SMILES: N[C@H]1CC[C@@H](C(=O)Nc2cc3cc[nH]c(=O)c3cc2Cl)C1] | (1R,3S)-3-Amino-cyclopentanecarboxylic acid (7-chloro-1-oxo-1,2-dihydro-isoquinolin-6-yl)-amide |
| 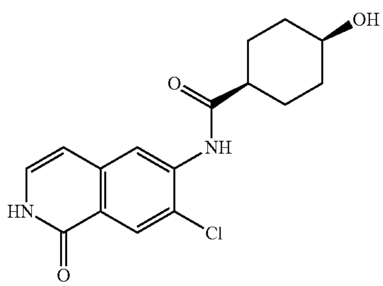 [SMILES: O=c1[nH]ccc2cc(NC(=O)[C@H]3CC[C@@H](O)CC3)c(Cl)cc12] | 4-Hydroxy-cyclohexanecarboxylic acid (7-chloro-1-oxo-1,2-dihydro-isoquinolin-6-yl)-amide |
| 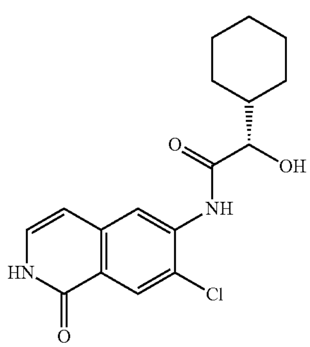 [SMILES: O=C(Nc1cc2cc[nH]c(=O)c2cc1Cl)[C@@H](O)C1CCCCC1] | (S)-N-(7-Chloro-1-oxo-1,2-dihydro-isoquinolin-6-yl)-2-cyclohexyl-2-hydroxy-acetamide |
| 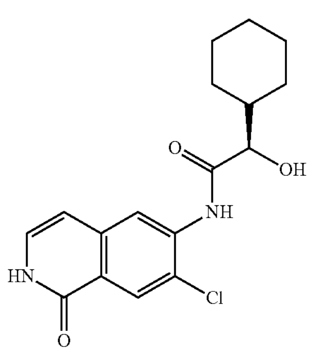 [SMILES: O=C(Nc1cc2cc[nH]c(=O)c2cc1Cl)[C@H](O)C1CCCCC1] | (R)-N-(7-Chloro-1-oxo-1,2-dihydro-isoquinolin-6-yl)-2-cyclohexyl-2-hydroxy-acetamide |

-continued

| Structure | Name |
|---|---|
| 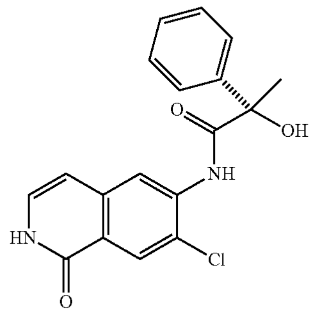 [SMILES: C[C@@](O)(C(=O)Nc1cc2cc[nH]c(=O)c2cc1Cl)c1ccccc1] | (S)-N-(7-Chloro-1-oxo-1,2-dihydro-isoquinolin-6-yl)-2-hydroxy-2-phenyl-propionamide |
| 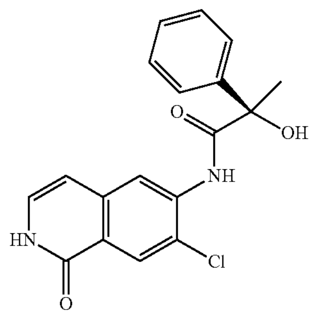 [SMILES: C[C@](O)(C(=O)Nc1cc2cc[nH]c(=O)c2cc1Cl)c1ccccc1] | (R)-N-(7-Chloro-1-oxo-1,2-dihydro-isoquinolin-6-yl)-2-hydroxy-2-phenyl-propionamide |
| 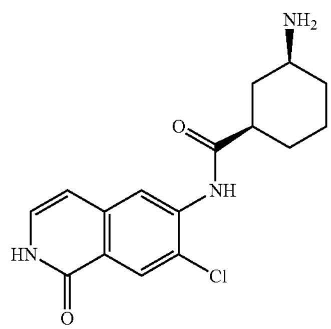 [SMILES: N[C@H]1CCC[C@@H](C(=O)Nc2cc3cc[nH]c(=O)c3cc2Cl)C1] | (1R,3S)-Amino-cyclohexanecarboxylic acid (7-chloro-1-oxo-1,2-dihydro-isoquinolin-6-yl)-amide |
| 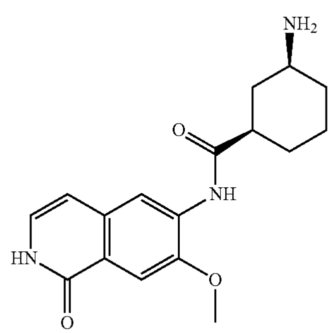 [SMILES: COc1cc2c(=O)[nH]ccc2cc1NC(=O)[C@@H]1CCC[C@H](N)C1] | (1R,3S)-3-Amino-cyclohexanecarboxylic acid (7-methoxy-1-oxo-1,2-dihydro-isoquinolin-6-yl)-amide |
| 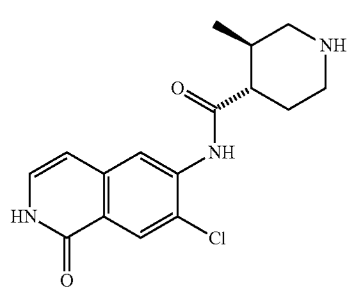 | (3R,4S)-3-Methyl-piperidine-4-carboxylic acid (7-chloro-1-oxo-1,2-dihydro-isoquinolin-6-yl)-amide |

| Structure | Name |
|---|---|
| 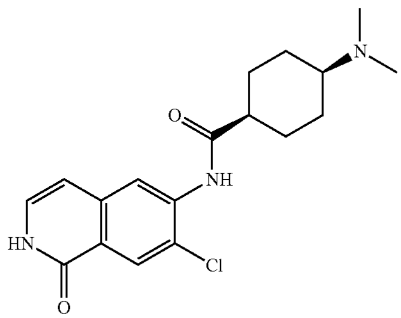 [SMILES: CN(C)[C@H]1CC[C@@H](C(=O)Nc2cc3cc[nH]c(=O)c3cc2Cl)CC1] | 4-Dimethylamino-cyclohexanecarboxylic acid (7-chloro-1-oxo-1,2-dihydro-isoquinolin-6-yl)-amide |
| | 3-Amino-cyclobutanecarboxylic acid (7-chloro-1-oxo-1,2-dihydro-isoquinolin-6-yl)-amide |
| | 3-Amino-cyclobutanecarboxylic acid (7-chloro-1-oxo-1,2-dihydro-isoquinolin-6-yl)-amide |
| | 4-Amino-1-(4-chloro-phenyl)-cyclohexanecarboxylic acid (7-chloro-1-oxo-1,2-dihydro-isoquinolin-6-yl)-amide |
| | 4-Amino-1-(4-chloro-phenyl)-cyclohexanecarboxylic acid (7-chloro-1-oxo-1,2-dihydro-isoquinolin-6-yl)-amide |

| Structure | Name |
| --- | --- |
| 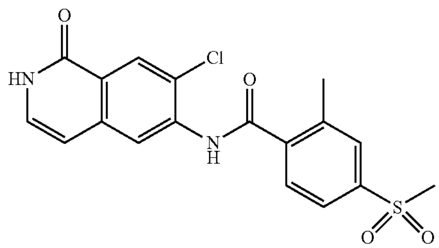 [SMILES: Cc1cc(S(C)(=O)=O)ccc1C(=O)Nc1cc2cc[nH]c(=O)c2cc1Cl] | N-(7-Chloro-1-oxo-1,2-dihydro-isoquinolin-6-yl)-4-methanesulfonyl-2-methyl-benzamide |
| 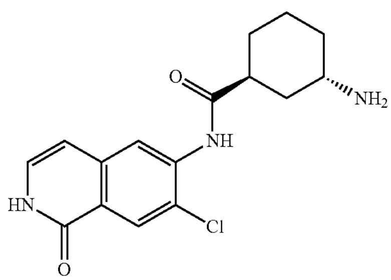 [SMILES: N[C@H]1CCC[C@H](C(=O)Nc2cc3cc[nH]c(=O)c3cc2Cl)C1] | (1S,3S)-3-Amino-cyclohexanecarboxylic acid (7-chloro-1-oxo-1,2-dihydro-isoquinolin-6-yl)-amide |
| 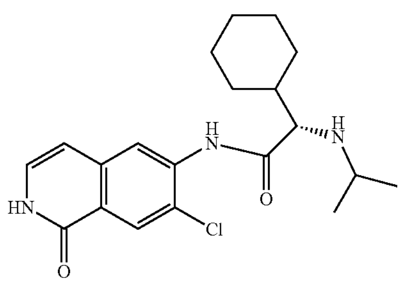 [SMILES: CC(C)N[C@H](C(=O)Nc1cc2cc[nH]c(=O)c2cc1Cl)C1CCCCC1] | (S)-N-(7-Chloro-1-oxo-1,2-dihydro-isoquinolin-6-yl)-2-cyclohexyl-2-isopropylamino-acetamide |
| 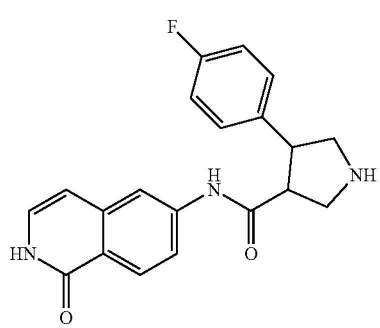 [SMILES: O=C(Nc1ccc2c(=O)[nH]ccc2c1)C1CNCC1c1ccc(F)cc1] | 4-(4-Fluoro-phenyl)-pyrrolidine-3-carboxylic acid (1-oxo-1,2-dihydro-isoquinolin-6-yl)-amide |
| 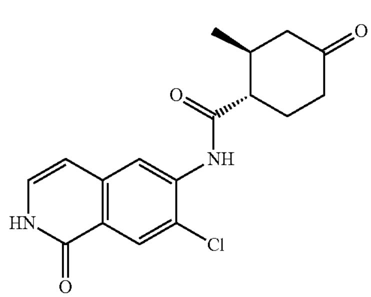 [SMILES: C[C@H]1CC(=O)CC[C@@H]1C(=O)Nc1cc2cc[nH]c(=O)c2cc1Cl] | (1S,2S)-2-Methyl-4-oxo-cyclohexanecarboxylic acid (7-chloro-1-oxo-1,2-dihydro-isoquinolin-6-yl)-amide |

-continued

| Structure | Name |
|---|---|
| 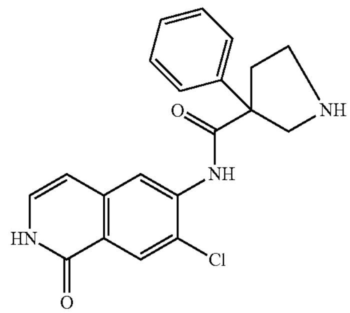 [SMILES: O=C(Nc1cc2cc[nH]c(=O)c2cc1Cl)C1(c2ccccc2)CCNC1] | 3-Phenyl-pyrrolidine-3-carboxylic acid (7-chloro-1-oxo-1,2-dihydro-isoquinolin-6-yl)-amide |
| 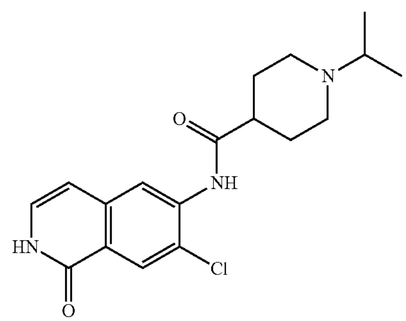 [SMILES: CC(C)N1CCC(C(=O)Nc2cc3cc[nH]c(=O)c3cc2Cl)CC1] | 1-Isopropyl-piperidine-4-carboxylic acid (7-chloro-1-oxo-1,2-dihydro-isoquinolin-6-yl)-amide |
| 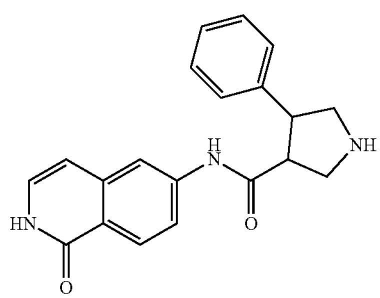 [SMILES: O=C(Nc1ccc2c(=O)[nH]ccc2c1)C1CNCC1c1ccccc1] | 4-Phenyl-pyrrolidine-3-carboxylic acid (1-oxo-1,2-dihydro-isoquinolin-6-yl)-amide |
| 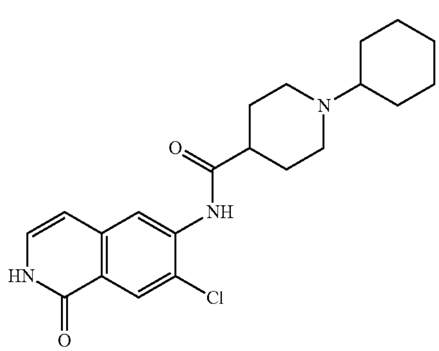 [SMILES: O=C(Nc1cc2cc[nH]c(=O)c2cc1Cl)C1CCN(C2CCCCC2)CC1] | 1-Cyclohexyl-piperidine-4-carboxylic acid (7-chloro-1-oxo-1,2-dihydro-isoquinolin-6-yl)-amide |

| Structure | Name |
| --- | --- |
| 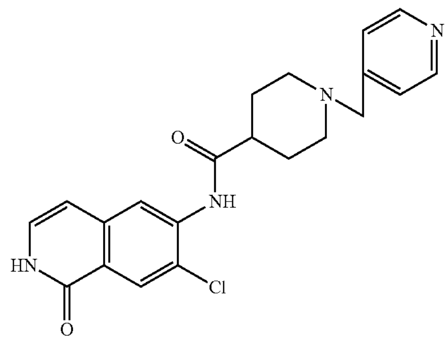 [SMILES: O=C(Nc1cc2cc[nH]c(=O)c2cc1Cl)C1CCN(Cc2ccncc2)CC1] | 1-Pyridin-4-ylmethyl-piperidine-4-carboxylic acid (7-chloro-1-oxo-1,2-dihydro-isoquinolin-6-yl)-amide |
| 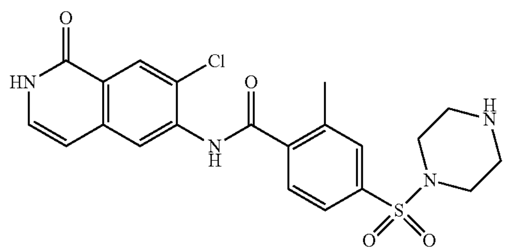 [SMILES: Cc1cc(S(=O)(=O)N2CCNCC2)ccc1C(=O)Nc1cc2cc[nH]c(=O)c2cc1Cl] | N-(7-Chloro-1-oxo-1,2-dihydro-isoquinolin-6-yl)-2-methyl-4-(piperazine-1-sulfonyl)-benzamide |
| 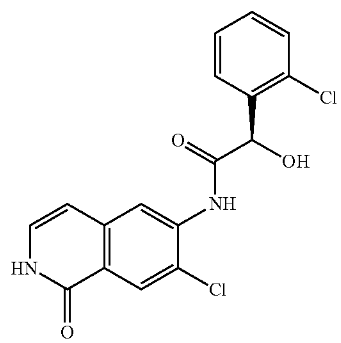 [SMILES: O=C(Nc1cc2cc[nH]c(=O)c2cc1Cl)[C@H](O)c1ccccc1Cl] | (R)-N-(7-Chloro-1-oxo-1,2-dihydro-isoquinolin-6-yl)-2-(2-chloro-phenyl)-2-hydroxy-acetamide |
| 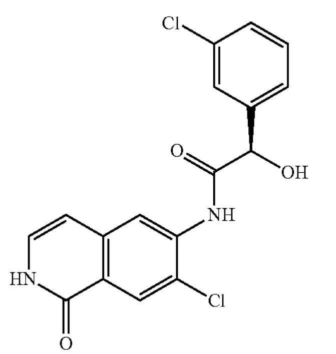 [SMILES: O=C(Nc1cc2cc[nH]c(=O)c2cc1Cl)[C@H](O)c1cccc(Cl)c1] | (R)-N-(7-Chloro-1-oxo-1,2-dihydro-isoquinolin-6-yl)-2-(3-chloro-phenyl)-2-hydroxy-acetamide |
| 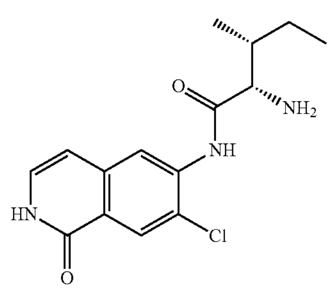 [SMILES: CC[C@@H](C)[C@H](N)C(=O)Nc1cc2cc[nH]c(=O)c2cc1Cl] | (2S,3R)-2-Amino-3-methyl-pentanoic acid (7-chloro-1-oxo-1,2-dihydro-isoquinolin-6-yl)-amide |

-continued

| Structure | Name |
|---|---|
| 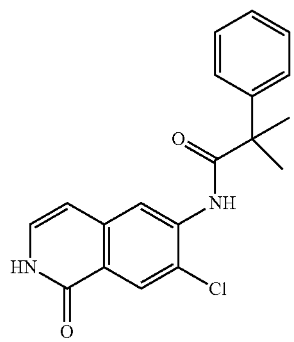 [SMILES: CC(C)(C(=O)Nc1cc2cc[nH]c(=O)c2cc1Cl)c1ccccc1] | N-(7-Chloro-1-oxo-1,2-dihydro-isoquinolin-6-yl)-2-phenyl-isobutyramide |
| 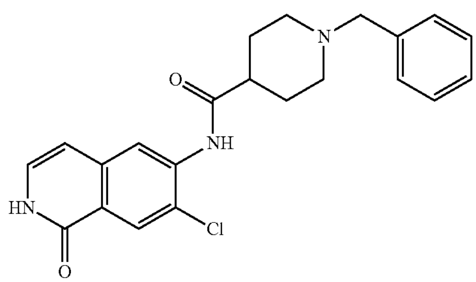 [SMILES: O=C(Nc1cc2cc[nH]c(=O)c2cc1Cl)C1CCN(Cc2ccccc2)CC1] | 1-Benzyl-piperidine-4-carboxylic acid (7-chloro-1-oxo-1,2-dihydro-isoquinolin-6-yl)-amide |
| 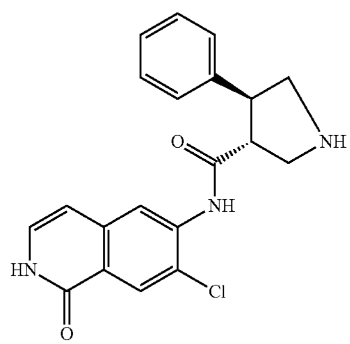 [SMILES: O=C(Nc1cc2cc[nH]c(=O)c2cc1Cl)[C@H]1CNC[C@@H]1c1ccccc1] | (trans)-4-Phenyl-pyrrolidine-3-carboxylic acid (7-chloro-1-oxo-1,2-dihydro-isoquinolin-6-yl)-amide |
| 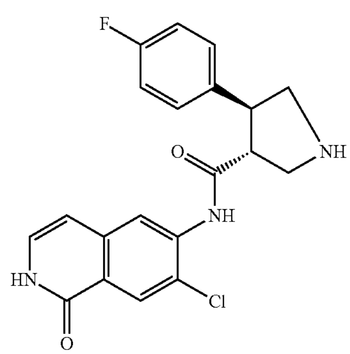 [SMILES: O=C(Nc1cc2cc[nH]c(=O)c2cc1Cl)[C@H]1CNC[C@@H]1c1ccc(F)cc1] | (trans)-4-(4-Fluoro-phenyl)-pyrrolidine-3-carboxylic acid (7-chloro-1-oxo-1,2-dihydro-isoquinolin-6-yl)-amide |
| 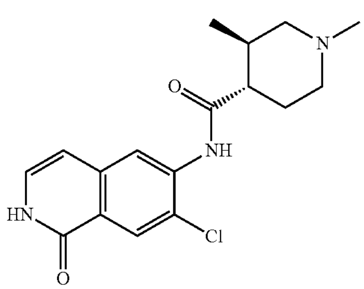 [SMILES: C[C@H]1CN(C)CC[C@@H]1C(=O)Nc1cc2cc[nH]c(=O)c2cc1Cl] | (3R,4S)-1,3-Dimethyl-piperidine-4-carboxylic acid (7-chloro-1-oxo-1,2-dihydro-isoquinolin-6-yl)-amide |

| Structure | Name |
|---|---|
| 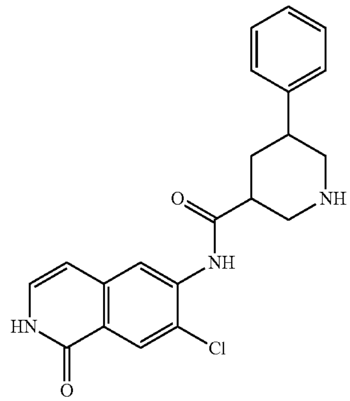 [SMILES: O=C(Nc1cc2cc[nH]c(=O)c2cc1Cl)C1CNCC(c2ccccc2)C1] | 5-Phenyl-piperidine-3-carboxylic acid (7-chloro-1-oxo-1,2-dihydro-isoquinolin-6-yl)-amide |
| 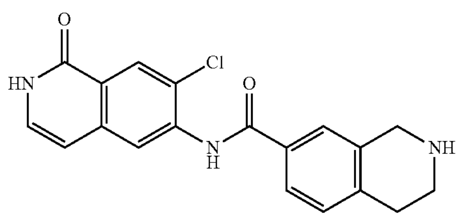 [SMILES: O=C(Nc1cc2cc[nH]c(=O)c2cc1Cl)c1ccc2c(c1)CNCC2] | 1,2,3,4-Tetrahydro-isoquinolin-7-carboxylic acid (7-chloro-1-oxo-1,2-dihydro-isoquinolin-6-yl)-amide |
| 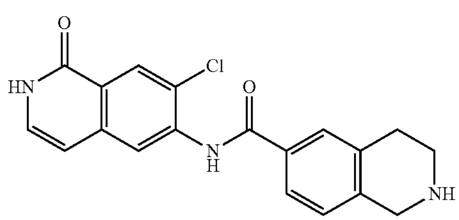 [SMILES: O=C(Nc1cc2cc[nH]c(=O)c2cc1Cl)c1ccc2c(c1)CCNC2] | 1,2,3,4-Tetrahydro-isoquinolin-6-carboxylic acid (7-chloro-1-oxo-1,2-dihydro-isoquinolin-6-yl)-amide |
| 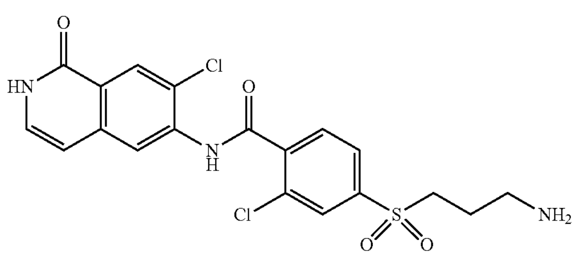 [SMILES: NCCCS(=O)(=O)c1ccc(C(=O)Nc2cc3cc[nH]c(=O)c3cc2Cl)c(Cl)c1] | 4-(3-Amino-propane-1-sulfonyl)-2-chloro-N-(7-dihydro-isoquinolin-6-yl)-benzamide |
| 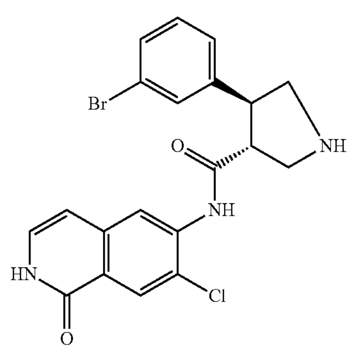 [SMILES: O=C(Nc1cc2cc[nH]c(=O)c2cc1Cl)[C@H]1CNC[C@@H]1c1cccc(Br)c1] | (trans)-4-(3-Bromo-phenyl)-pyrrolidine-3-carboxylic acid (7-chloro-1-oxo-1,2-dihydro-isoquinolin-6-yl)-amide |

| Structure | Name |
|---|---|
| 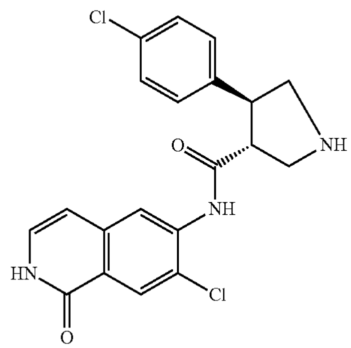 [SMILES: O=C(Nc1cc2cc[nH]c(=O)c2cc1Cl)[C@H]1CNC[C@@H]1c1ccc(Cl)cc1] | (trans)-4-(4-Chloro-phenyl)pyrrolidine-3-carboxylic acid (7-chloro-1-oxo-1,2-dihydro-isoquinolin-6-yl)-amide |
| 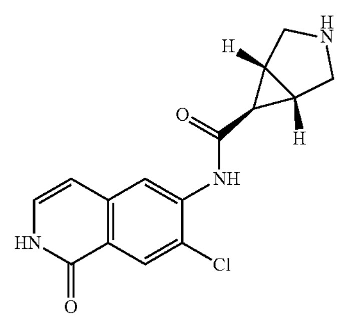 [SMILES: O=C(Nc1cc2cc[nH]c(=O)c2cc1Cl)[C@H]1[C@@H]2CNC[C@@H]21] | (1R,5S,6R)-3-Aza-bicyclo[3.1.10]hexane-6-carboxylic acid (7-chloro-1-oxo-1,2-dihydro-isoquinolin-6-yl)-amide |
| 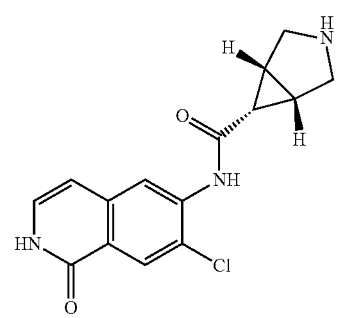 [SMILES: O=C(Nc1cc2cc[nH]c(=O)c2cc1Cl)[C@@H]1[C@@H]2CNC[C@@H]21] | (1R,5S,6S)-3-Aza-bicyclo[3.1.0]hexane-6-carboxylic acid (7-chloro-1-oxo-1,2-dihydro-isoquinolin-6-yl)-amide |
| 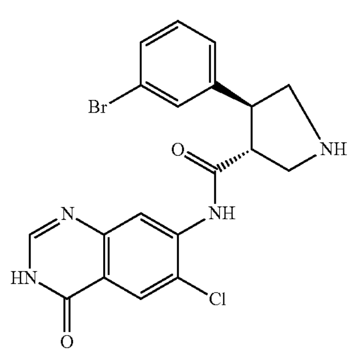 [SMILES: O=C(Nc1cc2nc[nH]c(=O)c2cc1Cl)[C@H]1CNC[C@@H]1c1cccc(Br)c1] | (trans)-4-(3-Bromo-phenyl)-pyrrolidine-3-carboxylic acid (6-chloro-4-oxo-3,4-dihydro-quinazolin-7-yl)-amide |

| Structure | Name |
|---|---|
| 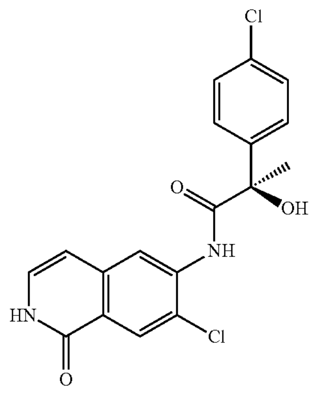 [SMILES: C[C@](O)(C(=O)Nc1cc2cc[nH]c(=O)c2cc1Cl)c1ccc(Cl)cc1] | (R)-N-(7-Chloro-1-oxo-1,2-dihydro-isoquinolin-6-yl)-2-(4-chloro-phenyl)-2-hydroxy-propionamide |
| 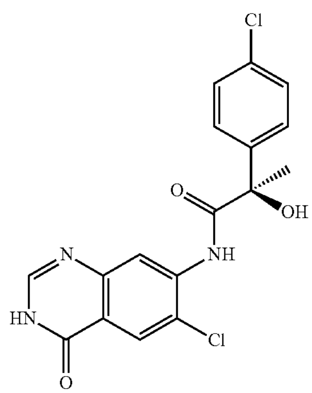 [SMILES: C[C@](O)(C(=O)Nc1cc2nc[nH]c(=O)c2cc1Cl)c1ccc(Cl)cc1] | (R)-N-(6-Chloro-4-oxo-3,4-dihydro-quinazolin-7-yl)-2-(4-chloro-phenyl)-2-hydroxy-propionamide |
| 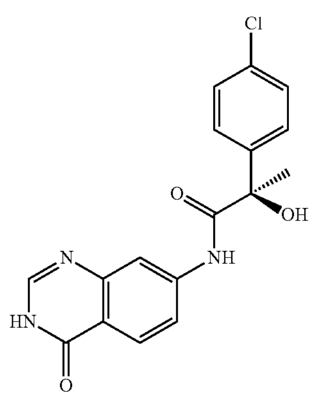 [SMILES: C[C@](O)(C(=O)Nc1ccc2c(=O)[nH]cnc2c1)c1ccc(Cl)cc1] | (R)-2-(4-Chloro-phenyl)-2-hydroxy-N-(4-oxo-3,4-dihydro-quinazolin-7-yl)-propionamide |
| 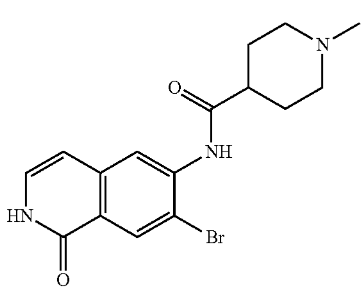 [SMILES: CN1CCC(C(=O)Nc2cc3cc[nH]c(=O)c3cc2Br)CC1] | 1-Methyl-piperidine-4-carboxylic acid (7-bromo-1-oxo-1,2-dihydro-isoquinolin-6-yl)-amide |

| Structure | Name |
|---|---|
| 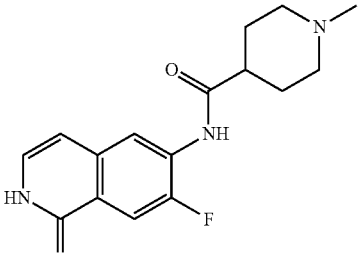 | 1-Methyl-piperidine-4-carboxylic acid (7-fluoro-1-oxo-1,2-dihydro-isoquinolin-6-yl)-amide |
| 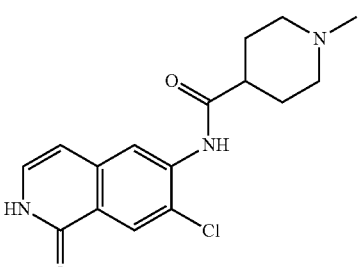 | 1-Methyl-piperidine-4-carboxylic acid (7-chloro-1-oxo-1,2-dihydro-isoquinolin-6-yl)-amide |
| 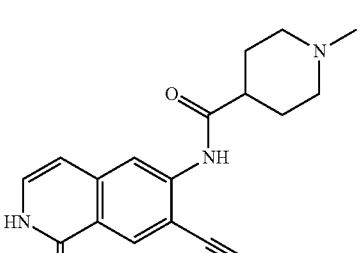 | 1-Methyl-piperidine-4-carboxylic acid (7-cyano-1-oxo-1,2-dihydro-isoquinolin-6-yl)-amide |
| 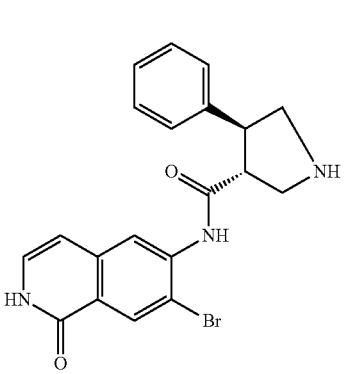 [SMILES: O=C(Nc1cc2cc[nH]c(=O)c2cc1Br)[C@H]1CNC[C@@H]1c1ccccc1] | (trans)-4-Phenyl-pyrrolidine-3-carboxylic acid (7-bromo-1-oxo-1,2-dihydro-isoquinolin-6-yl)-amide |
| 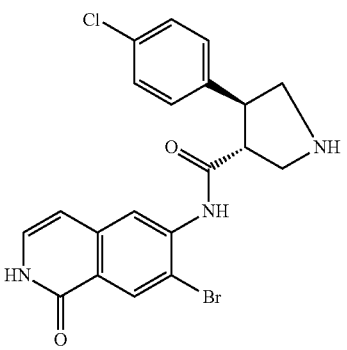 [SMILES: O=C(Nc1cc2cc[nH]c(=O)c2cc1Br)[C@H]1CNC[C@@H]1c1ccc(Cl)cc1] | (trans)-4-(4-Chloro-phenyl)-pyrrolidine-3-carboxylic acid (7-bromo-1-oxo-1,2-dihydro-isoquinolin-6-yl)-amide |

| Structure | Name |
|---|---|
| 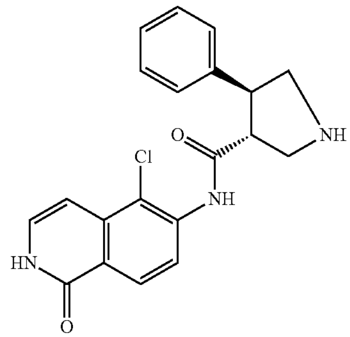 [SMILES: O=C(Nc1ccc2c(=O)[nH]ccc2c1Cl)[C@H]1CNC[C@@H]1c1ccccc1] | (trans)-4-Phenyl-pyrrolidine-3-carboxylic acid (5-chloro-1-oxo-1,2-dihydro-isoquinolin-6-yl)-amide |
| 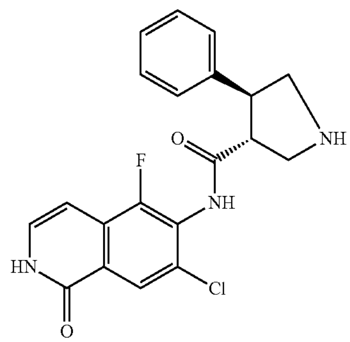 [SMILES: O=C(Nc1c(Cl)cc2c(=O)[nH]ccc2c1F)[C@H]1CNC[C@@H]1c1ccccc1] | (trans)-4-Phenyl-pyrrolidine-3-carboxylic acid (7-chloro-5-fluoro-1-oxo-1,2-dihydro-isoquinolin-6-yl)-amide |

In an additional embodiment of the invention, there are provided compounds of the formula (I) selected from the group below or a tautomer thereof or a salt thereof, preferably a pharmaceutically acceptable salt thereof:

N-(7-Chloro-1-oxo-1,2-dihydro-isoquinolin-6-yl)-2-dimethylamino-2-phenyl-acetamide;
N-(7-Chloro-1-oxo-1,2-dihydro-isoquinolin-6-yl)-2(4-methyl-piperazin-1yl)-acetamide;
N-(7-Chloro-1-oxo-1,2-dihydro-isoquinolin-6-yl)-2-(cyclohexylmethyl-amino-)-acetamide;
N-(7-Chloro-1-oxo-1,2-dihydro-isoquinolin-6-yl)-2(4-hydroxy-piperidin-1 yl)-2-phenyl-acetamide;
2-Benzylamino-N-(7-chloro-1-oxo-1,2-dihydro-isoquinolin-6-yl)-2-phenyl-acetamide;
N-(7-Chloro-1-oxo-1,2-dihydro-isoquinolin-6-yl)-2-thiomorpholin-4-yl-propionamide;
N-(7-Chloro-1-oxo-1,2-dihydro-isoquinolin-6-yl)-2-(1,2,3,4-tetrahydro-naphthalen-1-ylamino)-acetamide;
N-(7-Chloro-1-oxo-1,2-dihydro-isoquinolin-6-yl)-2-(2-thiophen-2-yl-ethylamino)-propionamide;
N-(7-Chloro-1-oxo-1,2-dihydro-isoquinolin-6-yl)-2-methylamino-2-phenyl-acetamide;
N-(7-Chloro-1-oxo-1,2-dihydro-isoquinolin-6-yl)-cyclopropylamino-2-phenyl-acetamide;
N-(7-Chloro-1-oxo-1,2-dihydro-isoquinolin-6-yl)-2-ethylmethyl-amino)-2-phenyl-acetamide;
(S)-2-Amino-N-(7-chloro-1-oxo-1,2-dihydro-isoquinolin-6-yl)-3-phenyl-propionamide;
(R)-2-Amino-N-(7-chloro-1-oxo-1,2-dihydro-isoquinolin-6-yl)-3-phenyl-propionamide;
(R)-2-Amino-N-(7-chloro-1-oxo-1,2-dihydro-isoquinolin-6-yl)-2-phenyl-acetamide;
N-(7-Chloro-1-oxo-1,2-dihydro-isoquinolin-6-yl)-2-cyclobutylamino-2-phenyl-acetamide;
N-(7-Chloro-1-oxo-1,2-dihydro-isoquinolin-6-yl)-2-cyclopropylmethyl-amino)-2-phenyl-acetamide;
N-(7-Chloro-1-oxo-1,2-dihydro-isoquinolin-6-yl)-2-(3-ethoxy-propylamino)-2-phenyl-acetamide;
N-(7-Chloro-1-oxo-1,2-dihydro-isoquinolin-6-yl)-2-[(2-dimethylamino-ethyl)-ethyl-amino]-2-phenyl-acetamide;
N-(7-Chloro-1-oxo-1,2-dihydro-isoquinolin-6-yl)-2-[(tetrahydro-pyran-4-yl-methyl)-amino]-acetamide;
2-(Adamantan-1-ylamino)-N-(7-chloro-1-oxo-1,2-dihydro-isoquinolin-6-yl)-acetamide;
N-(7-Chloro-1-oxo-1,2-dihydro-isoquinolin-6-yl)-2-[(pyridin-2-ylmethyl)-amino]-acetamide;
N-(7-Chloro-1-oxo-1,2-dihydro-isoquinolin-6-yl)-2-[(pyridin-3-ylmethyl)-amino]-acetamide;
N-(7-Chloro-1-oxo-1,2-dihydro-isoquinolin-6-yl)-2-[(pyridin-4-ylmethyl)-amino]-acetamide;
N-(7-Chloro-1-oxo-1,2-dihydro-isoquinolin-6-yl)-2-(cyclohexylmethyl-amino)-propionamide;
(7-Chloro-1-oxo-1,2-dihydro-isoquinolin-6-yl)-carbamic acid isopropyl ester;
2-Dimethylamino-N-(1-oxo-1,2-dihydro-isoquinolin-6-yl)-acetamide;
2-(Cyclohexylmethyl-amino)-N-(1-oxo-1,2-dihydro-isoquinolin-6-yl)-acetamide;
2-Dimethylamino-N-(1-oxo-1,2-dihydro-isoquinolin-6-yl)-phenyl-acetamide;
Acetic acid (7-chloro-1-oxo-1,2-dihydro-isoquinolin-6-yl-carbamoyl)-phenyl-methyl ester;
1-Benzyl-3-(1-oxo-1,2-dihydro-isoquinolin-6yl)-urea;
N-(7-chloro-1-oxo-1,2-dihydro-isoquinolin-6-yl)-2-hydroxy-2-phenyl-acetamide;
(R)-2-Amino-N-(1-oxo-1,2-dihydro-isoquinolin-6-yl)-2-phenyl-acetamide;
N-(7-Chloro-1-oxo-1,2-dihydro-isoquinolin-6-yl)-2-(4-chloro-phenyl)-3-methyl-butyramide;

2,5-Dichloro-thiophene-3-carboxylic acid (1-oxo-1,2-dihydro-isoquinolin-6-yl)-amide;
N-(1-Oxo-1,2-dihydro-isoquinolin-6-yl)-2-phenylsulfanyl-nicotinamide;
2-(3-Methoxy-phenyl)-N-(1-oxo-1,2-dihydro-isoquinolin-6-yl)-acetamide;
2-(4-Chloro-phenoxy)-N-(1-oxo-1,2-dihydro-isoquinolin-6-yl)-nicotinamide;
2-(4-Chloro-phenoxy)-2-methyl-N-(1-oxo-1,2-dihydro-isoquinolin-6-yl)-propionamide;
N-(1-Oxo-1,2-dihydro-isoquinolin-6-yl)-succinamic acid ethyl ester;
Thiophene-2-carboxylic acid (1-oxo-1,2-dihydro-isoquinolin-6-yl)-amide;
1-(4-Chloro-phenyl)-cyclopentanecarboxylic acid (1-oxo-1,2-dihydro-isoquinolin-6-yl)-amide;
2-(4-Chloro-phenoxy)-N-(1-oxo-1,2-dihydro-isoquinolin-6-yl)-acetamide;
N-(7-Chloro-1-oxo-1,2-dihydro-isoquinolin-6-yl)-2-methyl-benzamide;
N-(7-Chloro-1-oxo-1,2-dihydro-isoquinolin-6-yl)-2-phenyl-acetamide;
N-(7-Chloro-1-oxo-1,2-dihydro-isoquinolin-6-yl)-2,3,6-trifluoro-benzamide;
N-(7-Chloro-1-oxo-1,2-dihydro-isoquinolin-6-yl)-5-fluoro-2-methyl-benzamide;
2-Chloro-N-(7-chloro-1-oxo-1,2-dihydro-isoquinolin-6-yl)-4-nitro-benzamide;
2-Bromo-N-(7-chloro-1-oxo-1,2-dihydro-isoquinolin-6-yl)-benzamide;
N-(7-Chloro-1-oxo-1,2-dihydro-isoquinolin-6-yl)-2-(4-fluoro-phenyl)-acetamide;
N-(7-Chloro-1-oxo-1,2-dihydro-isoquinolin-6-yl)-2,2-dimethyl-propionamide;
N-(7-Chloro-1-oxo-1,2-dihydro-isoquinolin-6-yl)-3,3-dimethyl-butyramide;
N-(7-Chloro-1-oxo-1,2-dihydro-isoquinolin-6-yl)-2-phenylsulfanyl-nicotinamide;
2,4-Dichloro-N-(7-chloro-1-oxo-1,2-dihydro-isoquinolin-6-yl)-benzamide;
5-Methyl-3-phenyl-isoxazole-4-carboxylic acid (7-chloro-1-oxo-1,2-dihydro-isoquinolin-6-yl)-amide;
N-(7-Chloro-1-oxo-1,2-dihydro-isoquinolin-yl)-2,4,6-trifluoro-benzamide;
2,3-Dichloro-N-(7-chloro-1-oxo-1,2-dihydro-isoquinolin-6-yl)-benzamide;
2-Amino-N-(7-chloro-1-oxo-1,2-dihydro-isoquinolin-6-yl)-3-(4-fluoro-phenyl)-propionamide;
2-Amino-N-(7-chloro-1-oxo-1,2-dihydro-isoquinolin-6-yl)-2-(3-chloro-phenyl)-acetamide;
(R)-2-Amino-2-cyclohexyl-N-(1-oxo-1,2-dihydro-isoquinolin-6-yl)-acetamide;
(R)-2-Amino-2-(4-chloro-phenyl)-N-(1-oxo-1,2-dihydro-isoquinolin-6-yl)-acetamide;
(R)-Pyrrolidine-2-carboxylic acid (7-chloro-1-oxo-1,2-dihydro-isoquinolin-6-yl)-amide;
(S)-Pyrrolidine-2-carboxylic acid (7-chloro-1-oxo-1,2-dihydro-isoquinolin-6-yl)-amide;
2-Amino-N-(7-chloro-1-oxo-1,2-dihydro-isoquinolin-6-yl)-acetamide;
Piperidine-4-carboxylic acid (7-chloro-1-oxo-1,2-dihydro-isoquinolin-6-yl)-amide;
(R)-2-Amino-N-(7-chloro-1-oxo-1,2-dihydro-isoquinolin-6-yl)-3-(4-chloro-phenyl)-propionamide;
(R)-2-Amino-N-(7-chloro-1-oxo-1,2-dihydro-isoquinolin-6-yl)-2-p-tolyl-acetamide;
(S)-2-Amino-N-(7-chloro-1-oxo-1,2-dihydro-isoquinolin-6-yl)-3-cyclohexyl-propionamide;
(R)-2-Amino-N-(7-chloro-1-oxo-1,2-dihydro-isoquinolin-6-yl)-3-cyclohexyl-propionamide;
(R)-2-Amino-4,4-dimethyl-pentanoic acid (7-chloro-1-oxo-1,2-dihydro-isoquinolin-6-yl)-amide;
(S)-2-Amino-4,4-dimethyl-pentanoic acid (7-chloro-1-oxo-1,2-dihydro-isoquinolin-6-yl)-amide;
2-Chloro-N-(7-chloro-1-oxo-1,2-dihydro-isoquinolin-6-yl)-4-methanesulfonyl-benzamide;
2-Chloro-N-(7-chloro-1-oxo-1,2-dihydro-isoquinolin-6-yl)-4-morpholin-4-yl-benzamide;
(R)-2-Amino-N-(7chloro-1-oxo-1,2-dihydro-isoquinolin-6-yl)-3-naphthalen-2-yl-propionamide;
(R)-2-Amino-N-(7-chloro-1-oxo-1,2-dihydro-isoquinolin-6-yl)-3-naphthalen-1-yl-propionamide;
(R)-2-Amino-N-(7-chloro-1-oxo-1,2-dihydro-isoquinolin-6-yl)-3-pyridin-4yl-propionamide;
2-Methyl-2-methylamino-N-(1-oxo-1,2-dihydro-isoquinolin-6-yl)-propionamide;
2-Amino-2-methyl-N-(1-oxo-1,2-dihydro-isoquinolin-6-yl)-propionamide;
(R)—N-(7-Chloro-1-oxo-1,2-dihydro-isoquinolin-6-yl)-2-methoxy-2-phenyl-acetamide;
(S)—N-(7-Chloro-1-oxo-1,2-dihydro-isoquinolin-6-yl)-2-methoxy-2-phenyl-acetamide;
3-Amino-N-(7-chloro-1-oxo-1,2-dihydro-isoquinolin-6-yl)-propionamide;
(R)-2-Amino-N-(7-chloro-1-oxo-1,2-dihydro-isoquinolin-6-yl)-3-meth-yl-butyramide;
N-(7-Chloro-1-oxo-1,2-dihydro-isoquinolin-6-yl)-3,3,3-trifluoro-2-methoxy-2-phenyl-propionamide;
N-(7-Chloro-1-oxo-1,2-dihydro-isoquinolin-6-yl)-2-oxo-2-phenyl-acetamide;
(R)-Piperidine-2-carboxylic acid (7-chloro-1-oxo-1,2-dihydro-isoquinolin-6-yl)-amide;
2-tert-Butylamino-N-(7-chloro-1-oxo-1,2-dihydro-isoquinolin-6-yl)-acetamide;
(R)-2-Methoxy-N-(7-methoxy-1-oxo-1,2-dihydro-isoquinolin-6-yl)-2-phenyl-acetamide;
(S)-2-Methoxy-N-(7-methoxy-1-oxo-1,2-dihydro-isoquinolin-6-yl)-2-phenyl-acetamide;
(R)-2-Amino-2-cyclohexyl-N-(7-methoxy-1-oxo-1,2-dihydro-isoquinolin-6-yl)-acetamide;
(S)-2-Amino-2-cyclohexyl-N-(7-methoxy-1-oxo-1,2-dihydro-isoquinolin-6-yl)-acetamide;
4-Bromo-2-chloro-N-(7-chloro-1-oxo-1,2-dihydro-isoquinolin-6-yl)-benzamide;
2-Chloro-N-(7-chloro-1-oxo-1,2-dihydro-isoquinolin-6-yl)-5-methanesulfonyl-benzamide;
(R)-Tetrahydro-furan-2-carboxylic acid (7-chloro-1-oxo-1,2-dihydro-isoquinolin-6-yl)-amide;
(S)—N-(7-Chloro-1-oxo-1,2-dihydro-isoquinolin-6-yl)-2-hydroxy-2-phenyl-acetamide;
(R)—N-(7Chloro-1-oxo-1,2-dihydro-isoquinolin-6-yl)-2-hydroxy-2-phenyl-acetamide;
N-(7-Chloro-1-oxo-1,2-dihydro-isoquinolin-6-yl)-2-cyano-benzamide;
N-(7-Chloro-1-oxo-1,2-dihydro-isoquinolin-6-yl)-2-methyl-4-nitro-benzamide;
N-(7-Chloro-1-oxo-1,2-dihydro-isoquinolin-6-yl)-4-nitro-2-trifluoromethyl-benzamide;
N-(7-Chloro-1-oxo-1,2-dihydro-isoquinolin-6-yl)-2-morpholin-4-ylmethyl-benzamide;
1-Amino-cyclohexanecarboxylic acid (1-oxo-1,2-dihydro-isoquinolin-6-yl)-amide;

(R)-2-Amino-N-(7-chloro-1-oxo-1,2-dihydro-isoquinolin-6-yl)-2-cyclohexyl-acetamide;
(R)-2-Amino-4-methyl-pentanoic acid (7-chloro-1-oxo-1,2-dihydro-isoquinolin-6-yl)-amide;
(S)-2-Amino-N-(7-chloro-1-oxo-1,2-dihydro-isoquinolin-6-yl)-2-cyclohexyl-acetamide;
(S)-2-Amino-4-methyl-pentanoic acid (7-chloro-1-oxo-1,2-dihydro-isoquinolin-6-yl)-amide;
(S)-2-Amino-N-(7-chloro-1-oxo-1,2-dihydro-isoquinolin-6-yl)-3-methyl-butyramide;
N-(7-Chloro-1-oxo-1,2-dihydro-isoquinolin-6-yl)-2-(4-methyl-piperazin-1-ylmethyl)-benzamide;
1,2,3,4-Tetrahydro-isoquinoline-5-carboxylic acid (7-chloro-oxo-1,2-dihydro-isoquinolin-6-yl)-amide;
1,2,3,4-Tetrahydro-isoquinoline-8-carboxylic acid (7-chloro-1-oxo-1,2-dihydro-isoquinolin-6-yl)-amide;
1-Methyl-piperidine-4-carboxylic acid (7-chloro-1-oxo-1,2-dihydro-isoquinolin-6-yl)-amide;
(R)—N-(7-Chloro-1-oxo-1,2-dihydro-isoquinolin-6-yl)-methyl-succinamic acid methyl ester;
2-Chloro-N-(7-chloro-1-oxo-1,2-dihydro-isoquinolin-6-yl)-3-nitro-benzamide;
2-Chloro-N-(7-chloro-1-oxo-1,2-dihydro-isoquinolin-6-yl)-5-nitro-benzamide;
(S)-Tetrahydro-furan-2-carboxylic acid (7-chloro-1-oxo-1,2-dihydro-isoquinolin-6-yl)-amide;
N-(7-Chloro-1-oxo-1,2-dihydro-isoquinolin-6-yl)-3-methylsulfanyl-propionamide;
N-(7-Chloro-1-oxo-1,2-dihydro-isoquinolin-6-yl)-2-cyano-acetamide;
2-Bromo-N-(7-chloro-1-oxo-1,2-dihydro-isoquinolin-6-yl)-4-methyl-benzamide;
Tetrahydro-pyran-4-carboxylic acid (7-chloro-1-oxo-1,2-dihydro-isoquinolin-6-yl)-amide;
N-(7-Chloro-1-oxo-1,2-dihydro-isoquinolin-6-yl)-3-phenyl-succinamic acid;
N-(7-Chloro-1-oxo-1,2-dihydro-isoquinolin-6-yl)-malonamic acid ethyl ester;
N-(7-Chloro-1-oxo-1,2-dihydro-isoquinolin-6-yl)-2-methylsulfanyl-acetamide;
(S)-Pyrrolidine-3-carboxylic acid (7-chloro-1-oxo-1,2-dihydro-isoquinolin-6-yl)-amide;
(S)-Piperidine-3-carboxylic acid (7-chloro-1-oxo-1,2-dihydro-isoquinolin-6-yl)-amide;
(R)-Piperidine-3-carboxylic acid (7-chloro-1-oxo-1,2-dihydro-isoquinolin-6-yl)-amide;
N-(7-Chloro-1-oxo-1,2-dihydro-isoquinolin-6-yl)-2-methanesulfonyl-acetamide;
N-(7-Chloro-1-oxo-1,2-dihydro-isoquinolin-6-yl)-2-phenyl-malonamic acid;
(S)-Piperidine-2-carboxylic acid (7-chloro-1-oxo-1,2-dihydro-isoquinolin-6-yl)-amide;
1-Methanesulfonyl-4-methyl-piperidine-4-carboxylic acid (7-chloro-1-oxo-1,2-dihydro-isoquinolin-6-yl)-amide;
2-Chloro-N-(7-chloro-1-oxo-1,2-dihydro-isoquinolin-6-yl)-4-nitro-benzamide;
N-(7-Chloro-1-oxo-1,2-dihydro-isoquinolin-6-yl)-4-nitro-benzamide;
(R)-Pyrrolidine-3-carboxylic acid (7-chloro-1-oxo-1,2-dihydro-isoquinolin-6-yl)-amide;
4-Amino-cyclohexanecarboxylic acid (7-chloro-1-oxo-1,2-dihydro-isoquinolin-6-yl)-amide;
4-Amino-cyclohexanecarboxylic acid (7-chloro-1-oxo-1,2-dihydro-isoquinolin-6-yl)-amide;
4-(7-Chloro-1-oxo-1,2-dihydro-isoquinolin-6-ylcarbamoyl)-cyclohexanecarboxylic acid;
(R)—N-(7-Chloro-1-oxo-1,2-dihydro-isoquinolin-6-yl)-2-isopropoxy-2-phenyl-1-acetamide;
(R)—N-(7-Chloro-1-oxo-1,2-dihydro-isoquinolin-6-yl)-2-phenoxy-propionamide;
(S)—N-(7-Chloro-1-oxo-1,2-dihydro-isoquinolin-6-yl)-2-phenoxy-propionamide;
4-Phenyl-piperidine-4-carboxylic acid (7-chloro-1-oxo-1,2-dihydro-isoquinolin-6-yl)-amide;
4-(4-Chloro-phenyl)-piperidine-4-carboxylic acid (7-chloro-1-oxo-1,2-dihydro-isoquinolin-6-yl)-amide;
4-Benzyl-piperidine-4-carboxylic acid (7-chloro-1-oxo-1,2-dihydro-isoquinolin-6-yl)-amide;
(R)-Piperidine-3-carboxylic acid (1-oxo-1,2-dihydro-isoquinolin-6-yl)-amide;
(S)-Piperidine-3-carboxylic acid (1-oxo-1,2-dihydro-isoquinolin-6-yl)-amide;
1-Methyl-piperidine-4-carboxylic acid (1-oxo-1,2-dihydro-isoquinolin-6-yl)-amide;
(R)—N-(7-Chloro-1-oxo-1,2-dihydro-isoquinolin-6-yl)-2-hydroxy-3-methyl-butyramide;
Piperazine-2-carboxylic acid (7-chloro-1-oxo-1,2-dihydro-isoquinolin-6-yl)-amide;
4-Methyl-piperidine-4-carboxylic acid (7-chloro-1-oxo-1,2-dihydro-isoquinolin-6-yl)-amide;
(3S,4S-Methyl-piperidine-4-carboxylic acid (7-chloro-1-oxo-1,2-dihydro-isoquinolin-6-yl)-amide;
(3R,4S)-4-Phenyl-piperidine-3-carboxylic acid (7-chloro-1-oxo-1,2-dihydro-isoquinolin-6-yl)-amide;
Acetic acid 4-(7-chloro-1-oxo-1,2-dihydro-isoquinolin-6-ylcarbamoyl)-cyclohexyl ester (1R,3S)-3-Amino-cyclopentanecarboxylic acid (7-chloro-1-oxo-1,2-dihydro-isoquinolin-6-yl)-amide;
4-Hydroxy-cyclohexanecarboxylic acid (7-chloro-1-oxo-1,2-dihydro-isoquinolin-6-yl)-amide;
(S)—N-(7-Chloro-1-oxo-1,2-dihydro-isoquinolin-6-yl)-2-cyclohexyl-2-hydroxy-acetamide;
(R)—N-(7-Chloro-1-oxo-1,2-dihydro-isoquinolin-6-yl)-2-cyclohexyl-2-hydroxy-acetamide;
(S)—N-(7-Chloro-1-oxo-1,2-dihydro-isoquinolin-6-yl)-2-hydroxy-2-phenyl-propionamide;
(R)—N-(7-Chloro-1-oxo-1,2-dihydro-isoquinolin-6-yl)-2-hydroxy-2-phenyl-propionamide;
(1R,3S)-3-Amino-cyclohexanecarboxylic acid (7-chloro-1-oxo-1,2-dihydro-isoquinolin-6-yl)-amide;
(1R,3S)-3-Amino-cyclohexanecarboxylic acid (7-methoxy-1-oxo-1,2-dihydro-isoquinolin-6-yl)-amide;
(3R,4S)-3-Methyl-piperidine-4-carboxylic acid (7-chloro-1-oxo-1,2-dihydro-isoquinolin-6-yl)-amide;
4-Dimethylamino-cyclohexanecarboxylic acid (7-chloro-oxo-1,2-dihydro-isoquinolin-6-yl)-amide;
3-Amino-cyclobutanecarboxylic acid (7-chloro-1-oxo-1,2-dihydro-isoquinolin-6-yl)-amide;
4-Amino-1-(4-chloro-phenyl)-cyclohexanecarboxylic acid (7-chloro-1-oxo-1,2-dihydro-isoquinolin-6-yl)-amide;
N-(7-Chloro-1-oxo-1,2-dihydro-isoquinolin-6yl)-4-methanesulfonyl-2-methyl-benzamide;
(1S,3S)-3-Amino-cyclohexanecarboxylic acid (7-chloro-1-oxo-1,2-dihydro-isoquinolin-6-yl)-amide;
(S)—N-(7-Chloro-1-oxo-1,2-dihydro-isoquinolin-6-yl)-2-cyclohexyl-2-isopropylamino-acetamide;
4-(4-Fluoro-phenyl)-pyrrolidine-3-carboxylic acid (1-oxo-1,2-dihydro-isoquinolin-6-yl)-amide;
(1S,2S)-2-Methyl-4-oxo-cyclohexanecarboxylic acid (7-chloro-1-oxo-1,2-dihydro-isoquinolin-6-yl)-amide;
3-Phenyl-pyrrolidine-3-carboxylic acid (7-chloro-1-oxo-1,2-dihydro-isoquinolin-6-yl)-amide;

1-Isopropyl-piperidine-4-carboxylic acid (7-chloro-1-oxo-1,2-dihydro-isoquinolin-6-yl)-amide;
4-Phenyl-pyrrolidine-3-carboxylic acid (1-oxo-1,2-dihydro-isoquinolin-6-yl)-amide;
1-Cyclohexyl-piperidine-4-carboxylic acid (7-chloro-1-oxo-1,2-dihydro-isoquinolin-6-yl)-amide;
1-Pyridin-4-ylmethyl-piperidine-4-carboxylic acid (7-chloro-1-oxo-1,2-dihydro-isoquinolin-6-yl)-amide;
N-(7-Chloro-1-oxo-1,2-dihydro-isoquinolin-6-yl)-2-methyl-4(piperazine-1-sulfonyl)-benzamide;
(R)—N-(7-Chloro-1-oxo-1,2-dihydro-isoquinolin-6-yl)-2-(2-chloro-phenyl)-2-hydroxy-acetamide;
(R)—N-(7-Chloro-1-oxo-1,2-dihydro-isoquinolin-6-yl)-2-(3-chloro-phenyl)-2-hydroxy-acetamide;
(2S,3R)-2-Amino-3-methyl-pentanoic acid (7-chloro-1-oxo-1,2-dihydro-isoquinolin-6-yl)-amide;
N-(7-Chloro-1-oxo-1,2-dihydro-isoquinolin-6-yl)-2-phenyl-isobutyramide;
1-Benzyl-piperidine-4-carboxylic acid (7-chloro-1-oxo-1,2-dihydro-isoquinolin-6-yl)-amide;
(3R,4S)-4-Phenyl-pyrrolidine-3-carboxylic acid (7-chloro-1-oxo-1,2-dihydro-isoquinolin-6-yl)-amide;
(3R,4S)-4-(4-Fluoro-phenyl)-pyrrolidine-3-carboxylic acid (7-chloro-1-oxo-1,2-dihydro-isoquinolin-6-yl)-amide;
(3R,4S)-1,3-Dimethyl-piperidine-4-carboxylic acid (7-chloro-1-oxo-1,2-dihydro-isoquinolin-6-yl)-amide;
5-Phenyl-piperidine-3-carboxylic acid (7-chloro-1-oxo-1,2-dihydro-isoquinolin-6-yl)-amide;
1,2,3,4-Tetrahydro-isoquinolin-7-carboxylic acid (7-chloro-1-oxo-1,2-dihydro-isoquinolin-6-yl)-amide;
1,2,3,4-Tetrahydro-isoquinolin-6-carboxylic acid (7-chloro-1-oxo-1,2-dihydro-isoquinolin-6-yl)-amide;
4-(3-Amino-propane-1-sulfonyl)-2-chloro-N-(7-chloro-1-oxo-1,2-dihydro-isoquinolin-6-yl)-benzamide;
4-(3-Bromo-phenyl)-pyrrolidine-3-carboxylic acid (7-chloro-1-oxo-1,2-dihydro-isoquinolin-6-yl)-amide;
4-(4-chloro-phenyl)-pyrrolidine-3-carboxylic acid (7-chloro-1-oxo-1,2-dihydro-isoquinolin-6-yl)-amide;
(1R,5S,6R)-3-Aza-bicyclo[3.1.0]hexane-6-carboxylic acid (7-chloro-1-oxo-1,2-dihydro-isoquinolin-6-yl)-amide;
(1R,5S,6S)-3-Aza-bicyclo[3.1.0]hexane-6-carboxylic acid (7-chloro-1-oxo-1,2-dihydro-isoquinolin-6-yl)-amide;
(R)—N-(7-Chloro-1-oxo-1,2-dihydro-isoquinolin-6-yl)-2-(4-chloro-phenyl)-2-hydroxy-propionamide;
1-Methyl-piperidine-4-carboxylic acid (7-bromo-1-oxo-1,2-dihydro-isoquinolin-6-yl)-amide;
1-Methyl-piperidine-4-carboxylic acid (7-fluoro-1-oxo-1,2-dihydro-isoquinolin-6-yl)-amide;
1-Methyl-piperidine-4-carboxylic acid (7-chloro-1-oxo-1,2-dihydro-isoquinolin-6-yl)-amide;
1-Methyl-piperidine-4-carboxylic acid (7-cyano-1-oxo-1,2-dihydro-isoquinolin-6-yl)-amide;
4-Phenyl-pyrrolidine-3-carboxylic acid (7-bromo-1-oxo-1,2-dihydro-isoquinolin-6-yl)-amide; and
4-(4-Chloro-phenyl)-pyrrolidine-3-carboxylic acid (7-bromo-1-oxo-1,2-dihydro-isoquinolin-6-yl)-amide.

In another embodiment of the invention, there are provided compounds of the formula (I) selected from the group below or a tautomer thereof or a salt thereof, preferably a pharmaceutically acceptable salt thereof:
1-(4-Chloro-phenyl)-cyclopentanecarboxylic acid (4-oxo-3,4-dihydro-quinazolin-7-yl)-amide;
Piperidine-4-carboxylic acid (4-oxo-3,4-dihydro-quinazolin-7-yl)-amide;
2-Benzylamino-N-(4-oxo-3,4-dihydro-quinazolin-7-yl)-acetamide;
1-Benzyl-piperidine-4-carboxylic acid (4-oxo-3,4-dihydro-quinazolin-7-yl)-amide;
Piperidine-3-carboxylic acid (4-oxo-3,4-dihydro-quinazolin-7-yl)-amide;
Pyrrolidine-2-carboxylic acid (4-oxo-3,4-dihydro-quinazolin-7-yl)-amide;
2-Amino-4-methyl-pentanoic acid (4-oxo-3,4-dihydro-quinazolin-7-yl)-amide;
(R)-2-Amino-N-(4-oxo-3,4-dihydro-quinazolin-7-yl)-3-phenyl-propionamide;
(S)-2-Amino-N-(4-oxo-3,4-dihydro-quinazolin-7-yl)-3-phenyl-propionamide;
2-(Cyclohexylmethyl-amino)-N-(4-oxo-3,4-dihydro-quinazolin-7-yl)-acetamide;
2-Methylamino-N-(4-oxo-3,4-dihydro-quinazolin-7-yl)-2-phenyl-acetamide;
2-Amino-N-(4-oxo-3,4-dihydro-quinazolin-7-yl)-2-phenyl-acetamide;
2-Cyclopropylamino-N-(4-oxo-3,4-dihydro-quinazolin-7-yl)-2-phenyl-acetamide;
(R)-2-Amino-N-(4-oxo-3,4-dihydro-quinazolin-7-yl)-2-phenyl-acetamide;
(R)-Pyrrolidine-2-carboxylic acid (4-oxo-3,4-dihydro-quinazolin-7-yl)-amide;
(R)-2-Amino-3-methyl-N-(4-oxo-3,4-dihydro-quinazolin-7-yl)-butyramide;
2-(Cyclopropylmethyl-amino)-N-(4-oxo-3,4-dihydro-quinazolin-7-yl)-acetamide;
N-(4-oxo-3,4-dihydro-quinazolin-7-yl)-2-(2-thiophen-2-yl-ethylamino)-acetamide;
2-(Cyclohexyl-methyl-amino)-N-(4-oxo-3,4-dihydro-quinazolin-7-yl)-acetamide;
N-(6-Chloro-4-oxo-3,4-dihydro-quinazolin-7-yl)-2-dimethylamino-2-phenyl-acetamide;
N-(6-Chloro-4-oxo-3,4-dihydro-quinazolin-7-yl)-2-cyclopropylamino-2-phenyl-acetamide;
2,5-Dimethyl-2H-pyrazole-3-carboxylic acid (4-oxo-3,4-dihydro-quinazolin-7-yl)-amide;
4-(3-Bromo-phenyl)-pyrrolidine-3-carboxylic acid (6-chloro-4-oxo-3,4-dihydro-quinazolin-7-yl)-amide;
(R)—N-(6-Chloro-4-oxo-3,4-dihydro-quinazolin-7yl)-2-(4-chloro-phenyl)-2-hydroxy-propionamide;
and
(R)-2-(4-Chloro-phenyl)-2-hydroxy-N-(4-oxo-3,4-dihydro-quinazolin-7-yl)-propionamide;

For the compounds disclosed hereinabove in this application, in the event the nomenclature is in conflict with the structure, it shall be understood that the compound is defined by the structure.

In another embodiment of the invention the above described compounds of formula (I) are used in methods of treating a disease-state or condition mediated by Rho kinase in an individual, the method comprising administering to the individual an effective amount of a compound of formula (I) or tautomer thereof, or salt thereof, preferably a pharmaceutically acceptable salt thereof.

In another embodiment of the invention the above described compounds of formula (I) are used in methods of treating a cardiovascular disease or condition in an individual, the method comprising administering to the individual an effective amount of a compound of formula (I) or tautomer thereof, or salt thereof, preferably a pharmaceutically acceptable salt thereof.

Preferred cardiovascular disease or conditions are hypertension, atherosclerosis, restenosis, stroke, heart failure, coronary vasospasm, cerebral vasospasm, ischemia/reperfusion injury, pulmonary hypertension, angina, myocardial infarction, peripheral artery disease, coronary artery disease and combinations thereof.

In yet another embodiment of the invention the above described compounds of formula (I) are used in methods of treating renal disease, erectile dysfunction, asthma, glaucoma, or organ failure resulting from hypertension in an individual, the method comprising administering to the individual an effective amount of a compound of formula (I) or tautomer thereof, or salt thereof, preferably a pharmaceutically acceptable salt thereof.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

The compounds of the invention are meant to embrace compounds of Formula (I) as herein described, including the prodrugs, and the solvates and hydrates thereof.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows: Carbocycles including Cycloalkyl and Cycloalkenyl groups, are hydrocarbon rings containing from three to twelve carbon atoms. These carbocycles may be either aromatic or non-aromatic ring systems, monocyclic or polycyclic. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N, O and S. Unless otherwise stated, such heteroaryls include thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

The term "heteroatom" used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle, such as phenyl or naphthyl or heteroaryl as defined above. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydronaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$alkyl and —S(O)$_2$—$C_{1-6}$ alkyl, likewise, —S—$R_a$ may be represented as phenyl-S(O)$_m$— when $R_a$ is phenyl and where m is 0, 1 or 2.

The term "halogen" as used in the present specification shall be understood to mean bromine, chlorine, fluorine or iodine, preferably fluorine or chlorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —CH$_2$CHF$_2$, —CF$_3$ etc.

The compounds of the invention ate only those which are contemplated to be 'chemically stable' as will be appreciated by those skilled in the art. For example, a compound which would have a 'dangling valency', or a 'carbanion' are not compounds contemplated by the inventive methods disclosed herein.

In another aspect of the invention, the compounds of the invention are formulated into pharmaceutical compositions comprising an effective amount, preferably a pharmaceutically effective amount of a compound of the invention or a tautomer, or salt thereof and a pharmaceutically acceptable excipient or carrier. Pharmaceutically acceptable salts are preferred.

The invention also provides a kit for the in vitro diagnostic determination of Rho kinase function in a sample, comprising: (a) a diagnostically effective amount of a compound according to the invention or a tautomer thereof, or salt thereof; and (b) instructions for use of the diagnostic kit.

The invention includes pharmaceutically acceptable derivatives of compounds of formula (I). A "pharmaceutically acceptable derivative" refers to any pharmaceutically acceptable salt or ester, or any other compound which, upon administration to an individual, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and $N-(C_1-C_4\ alkyl)_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to an individual, the prodrug may be transformed into a compound disclosed hereinabove, thereby imparting the desired pharmacological effect.

General Synthetic Methods

The invention additionally provides for methods for making the compounds of the formula (I). The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Reaction progress may be monitored by conventional methods such as thin layer chromatography (TLC). Intermediates and products may be purified by methods known in the art, including column chromatography, HPLC or recrystallization.

The isoquinolinone core structures used to prepare compounds of formula (I) having x=C may be prepared by methods known in the art (for example. F. Eloy and A. Deryckere, J. Heterocyclic Chem, 1971, 8, 57; N. Briet et al., Tetrahedron, 2002, 58, 5761) and outlined in Scheme 1.

Scheme 1

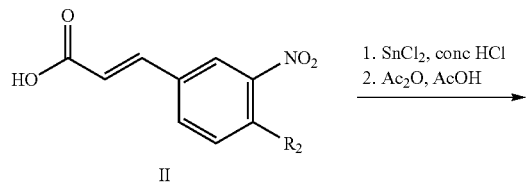

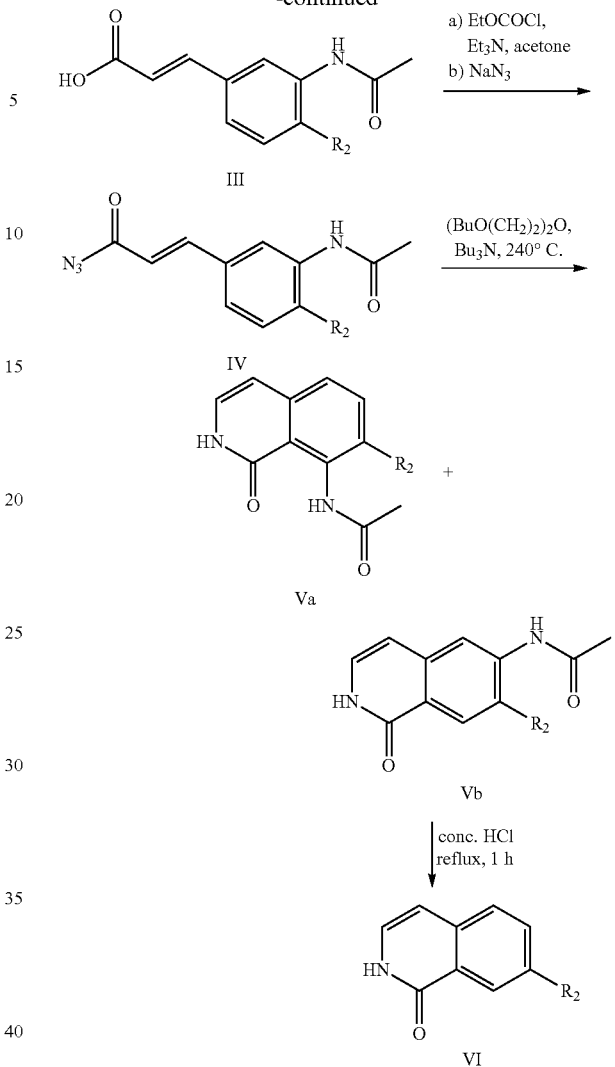

A nitro substituted cinnamic acid (II) is reduced to the corresponding amine using for example tin II chloride in hydrochloric acid. The amine is protected with a protecting group compatible with the cyclization conditions, such as an acetyl group. The resulting amide substituted cinnamic acid (III) is converted to the corresponding acyl azide by methods known in the art, for example, activation of the carboxylic acid by treatment with a chloroformate such as ethyl chloroformate, in the presence of an amine such as triethylamine, followed by treatment of the resulting mixed anhydride with an aqueous solution of an azide such as sodium azide. The resulting acyl azide (IV) is converted to the isoquinolone by heating in a solvent such as an ether of diethylene glycol, such as diethylene glycol dibutyl ether (dibutyl carbitol) or diphenyl ether, preferably in the presence of a base such as tributyl amine, at a temperature of 200-300° C., preferably 230-260° C. In some cases, depending on the nature of $R_1$, a mixture of regioisomeric products is formed, (Va and Vb) which can be separated by chromatography.

The protecting group may be removed from the separated 6-amino isomer by hydrolysis, preferably under acidic conditions using an acid such as concentrated hydrochloric acid. The resulting amino isoquinolinone formed (VI) can be used to prepare amide derivatives of formula (I) (X=C, Y=—NHC(O)—) by coupling with a carboxylic acid or carboxylic acid derivative using methods well known in the art and described in the Synthetic Examples section below. Ureas (X=C, Y=—NHC(O)NH—) and carbamates (X=C, Y=—NHC(O)O—) may be prepared by reaction of the isoquinolinome VI with an isocyanate or chloroformate respectively.

Quinazolinone intermediates (IX) used to prepare compounds of formula (I) having X.dbd.N may be prepared by methods known in the art as described in Scheme 2.

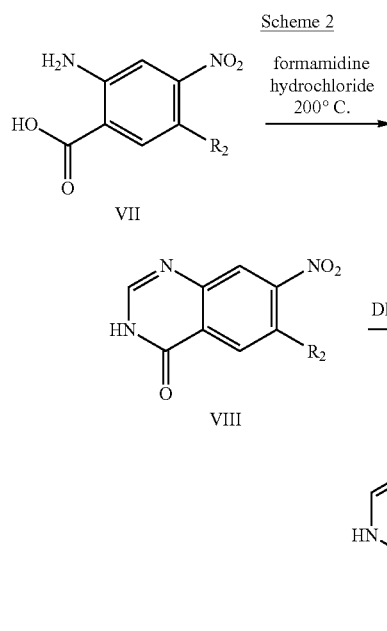

Heating the nitro anthranilic acid (VII) with a salt of formamidine, preferably the hydrochloride or acetate salt, at a temperature of about 200° C., provides VIII (Q. Chao et al., J. Med. Chem. 1999, 42, 3860). Alternatively, the anthranilic acid may be heated with formamide at a temperature of 130 to 150° C. in a microwave reactor (F.-R. Alexandre et al., Tet. Lett. 2002, 43, 3911, and F.-R. Alexandre et al., Tet. Lett. 2003, 44, 4455) to provide VIII. Reduction of the nitro group to the amine (IX) may be carried out by standard methods, such as catalytic hydrogenation over palladium, or transfer hydrogenation using a palladium catalyst and ammonium formate as the hydrogen source. The resulting amino quinazolinone formed (IX) can be used to prepare amide derivatives of formula (I) (X=N, Y=—NHC(O)—) by coupling with a carboxylic acid or carboxylic acid derivative) using methods well known in the art and described in the Synthetic Examples section below. Ureas (X=N, Y=—NHC(O)NH—) and carbamates (X=C, Y=—NHC(O)O—) may be prepared by reaction of the isoquinolinome VI with an isocyanate or chloroformate respectively.

SYNTHETIC EXAMPLES

Examples 1-7 illustrate the synthesis of 6-aminoisoquinolin-1-one and 7-aminoquinazolin-4-one intermediates that may be used to prepare desired compounds of formula (I).

Example 1: Synthesis of 6-aminoisoquinolin-1-one

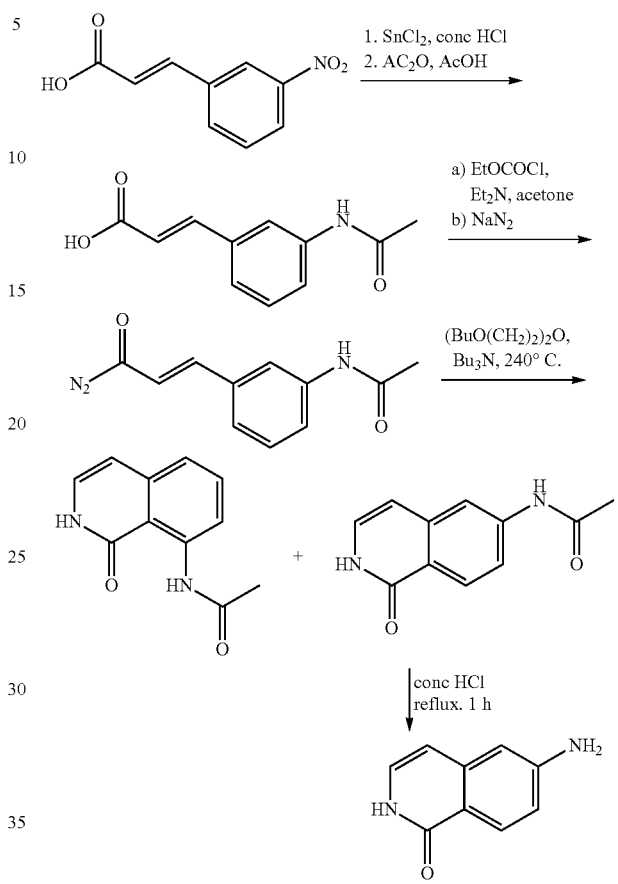

Tin II chloride dihydrate (1.70 g, 0.75 mol) was dissolved in concentrated HCl (200 mL). Warming was necessary to obtain a clear solution. 3-Nitrocinnamic acid (35 g, 0.181 mol) was added portionwise with stirring. After about 20% of the 3-nitrocinnamic acid had been added, the mixture was warmed with a heat gun to 45° C. to initiate reaction. The rate of addition was controlled to maintain a temperature of 65-75° C. The reaction was exothermic, but not vigorous on this scale. After the addition was complete, and the reaction started to subside, the flask was transferred to an oil bath at 65° C. for 1 h. The mixture was then cooled to room temperature. The solid was filtered, washed with 2 N HCl, (100 mL) and sucked dry. The filter cake was dried in a vacuum oven for 1 h, then in air overnight, to give about 65 g of the crude amine. This material was suspended in acetic acid (300 mL) and acetic anhydride (150 mL, 1.6 mol) was added gradually with stirring. After the initial exotherm subsided, the mixture was stirred in an oil bath at 110° C. for 2 h, resulting in a clear solution. LCMS showed complete conversion to the desired acetanilide. The solution was cooled and water (50 mL) was added. After standing overnight the solution was concentrated to about 300 mL. More water (100 mL) and 2 N HCl (50 mL) were added. The precipitate was filtered, washed with water and dried to give 3-acetamido cinnamic acid (33.2 g, 89%).

A solution of 3-acetamido cinnamic acid (3.0 g, 15 mmol) and triethylamine (4.2 mL, 30 mmol) in acetone (27 mL) was cooled in an ice bath. Ethyl chloroformate (1.86 mL, 19.5 mmol) was added, and the solution was stirred in ice for 40 min. Triethylamine hydrochloride precipitated. A solution of sodium azide (1.46 g, 22.5 mmol) in water (3 mL) was added. The mixture was stirred in ice for 40 min, then for 1 h at room temperature. Water (15 mL) was added, and the solution was extracted three times with dichloromethane. The combined organic layers were dried over magnesium sulfate and evaporated to dryness to give the crystalline azide.

While this reaction was in progress, a 100 mL 3-neck round bottom flask, equipped with magnetic stirrer, pressure-equalizing addition funnel, thermocouple connected to a J-KEM controller and an air condenser topped by short-path distillation head and receiver, was charged with a mixture of diethyleneglycol dibutyl ether (dibutyl carbitol) (10 mL) and tributyl amine (3.3 mL, 15 mmol). The stirred solution was heated to 240° C. using a heating mantle connected to the J-KEM controller. Nitrogen was passed through the apparatus via an inlet connected to the top of the addition funnel. The azide was redissolved in dichloromethane (80 mL, with warming), and this solution was placed in the addition funnel. The nitrogen stream was stopped. The azide solution was added slowly dropwise, to maintain the temperature between 230° C. and 240° C. Very vigorous gas evolution occurred as the azide was added. The dichloromethane boiled off as the solution was added. The addition took 2 h 10 min, during which time a distillate collected in the receiver, which was a mixture of dichloromethane and dibutyl carbitol. Periodically during the addition, the receiver was changed. The dichloromethane was evaporated, and the liquid remaining in the flask was returned to the reaction vessel. After the addition was complete, the temperature was maintained at 240° C. for 40 min. The healing mantle was removed. A dark solid had deposited on the walls of the flask. On cooling, a crystalline precipitate formed. The precipitate was collected by filtration, and washed with ether. The dark solid remained in the flask. More solid crystallized from the ether filtrate on standing. The supernatant was decanted, and the solid combined with the filtered precipitate. The supernatant was distilled under high vacuum, to remove the carbitol and tributylamine. The combined solids and pot residue from the distillation contained both the 8-acetamido isoquinolin-1-one and 6-acetamido isoquinolin-1-one. This material was purified by chromatography on silica, using a dichloromethane/methanol gradient from 2% to 15%. The first eluted component was the 8-acetamido isomer (700 mg isolated pure). The second eluted component was the desired 6-acetamido isomer (600 mg). This component contained impurities, which were removed by triturating the material with a little methanol (ca. 3 mL). The crystals were filtered, washed with a few drops of methanol and dried to give pure 6-acetamido isoquinolin-1-one (354 mg, 12%).

A stirred suspension of 6-acetamidoisoquinolin-1-one (1.62 g, 8.0 mmol) in 6 M HCl (60 mL) was healed in an oil bath at 65° C. with stirring. After 2 h a clear solution was obtained, and the reaction was complete by LCMS. The solution was cooled and evaporated almost to dryness.

Methanol was evaporated from residue to leave the hydrochloride salt as a crystalline solid. The salt was suspended in water (40 mL) and heated to at 60° C. to dissolve. To the resulting solution at 60° C., ammonium hydroxide was added dropwise, immediately forming a precipitate. The mixture was cooled in ice, the crystals filtered, and washed with water, and finally with a few drops of methanol, which removed some brown color. The crystals were dried to give the title compound (1.00 g, 78%).

Example 2: Synthesis of 6-amino-5-chloroisoquinolin-1-one

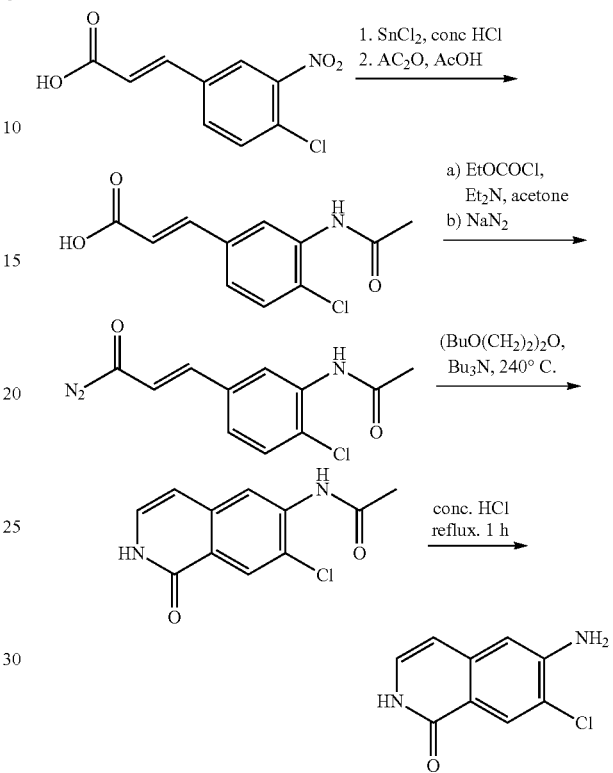

Tin II chloride dihydrate (103 g, 0.46 mol) was dissolved in concentrated HCl (120 mL). Warming was necessary to obtain a clear solution. 4-Chloro-3-nitrocinnamic acid (25 g, 0.11 mol) was added portionwise with stirring. After about 20% of the starting material had been added, the mixture was warmed with a heat gun to 45° C. to initiate reaction. The rate of addition was controlled to maintain a temperature of 65-75° C. Cooling with a water bath was used to prevent the temperature exceeding 80° C. After the addition was complete and reaction started to subside, the mixture was transferred to an oil bath at 65° C. for 1 h. The mixture was cooled to room temperature. The solid was filtered, washed with 2 M HCl, (60 mL) and sucked dry. The filter cake was dried in a vacuum oven for 1 h, then in air overnight, to give about 34 g crude product. This material was suspended in acetic acid (100 ml) with stirring and acetic anhydride (100 mL, 1.1 mol) was added in one portion. The temperature rose to 35° C. After the initial exotherm subsided, the mixture was stirred in an oil bath at 110° C. for 2 h, but did not dissolve. LCMS showed complete conversion to the desired acetanilide. The solution was cooled and water (50 mL) was added cautiously. The mixture was concentrated to about 200 mL. More water (100 mL) and 2 M HCl (50 mL) were added. The precipitate was filtered, washed with water and dried to give 3-acetamido-4-chlorocinnamic acid (25.0 g, 95%).

A suspension of 3-acetamido-4-chlorocinnamic acid (7.19 g, 30 mmol) and triethylamine (8.4 mL, 60 mmol) in acetone (100 mL) was cooled in an ice bath. Ethyl chloroformate (3.73 mL, 39 mmol) was added, and the solution was stirred in ice for 40 min. The acid dissolved and a precipitate formed. A solution of sodium azide (2.93 g, 45 mmol) in water (10 mL) was added. The mixture was stirred in ice for 40 min, then for 1 h at room temperature. Water (75 mL) was added, and the solution was extracted three times with dichloromethane. The combined organic layers were dried over magnesium sulfate and evaporated to dryness, to give the crystalline azide.

While this reaction was in progress, the apparatus described above in Example 1 was assembled, using a 250 mL 3-neck round bottom flask, which was charged with diethyleneglycol dibutyl ether (dibutyl carbitol) (75 mL) and tributyl amine (7.2 mL, 30 mmol). The stirred solution was heated to 240° C. using a heating mantle connected to the J-KEM controller. Nitrogen was passed through the apparatus via an inlet connected to the top of the addition funnel. The azide was redissolved in dichloromethane (160 mL), with warming, and this solution was placed in the addition funnel. The nitrogen stream was stopped. The azide solution was added dropwise, to maintain temp between 230° C. and 250° C., so that the dichloromethane boiled off as the solution was added. The addition took 1 h 40 min. A distillate collected in the receiver, which was a mixture of dichloromethane and dibutyl carbitol. Periodically during the addition, the receiver was changed. The dichloromethane was evaporated, and the liquid remaining in the flask was returned to the reaction vessel. After the addition was complete, the temperature was maintained at 240° C. for 30 min. The heating mantle was removed. On cooling, a crystalline precipitate formed. The cooled solution was diluted with ether (150 mL) and stirred overnight. The precipitate was collected by filtration, washed well with ether, then with a few drops of MeOH, which removed some dark color. The resulting off-white solid was dried at 60° C. under vacuum to give 6-acetamido-5-chloroisoquinoline-1-one (3.1 g). This material contained a minor component which was not removed at this stage.

A stirred suspension of 6-acetamido-5-chloroisoquinolin-1-one (1.4 g, 5.9 mmol) in concentrated HCl (50 mL) was heated in an oil bath at 65.degree. C. with stirring. After 1 h, a clear solution was obtained, and the reaction was complete by LCMS. The solution was cooled and evaporated almost to dryness. Methanol was evaporated from the residue to leave the hydrochloride salt as a crystalline solid. The salt was dissolved in methanol and treated with excess ammonium hydroxide to form the free base. The solution was evaporated to dryness and was purified by chromatography on a Combiflash system, using a dichloromethane/methanol gradient from 2% to 10%. The major, second eluting, spot was collected to yield the title compound (883 mg, 72%).

Analogous procedures were used to make the 7-H, 7-bromo, 7-fluoro, and 7-trifluoromethyl derivatives using commercially available starting materials. The 7-cyano and 7-methoxy analogs were made by the following methods below.

Example 3: Synthesis of 6-amino-7-cyano isoquinolin-1-one

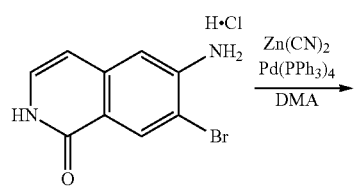

A reaction vial was charged with 7-bromo-6-aminoisoquinolone hydrochloride (203 mg, 0.74 mmol), Zn(CN)$_2$ (155 mmol) and Pd(Ph$_3$P)$_4$ (0.37 mmol) in 1.5 mL of dry dimethylacetamide. The vial was sealed and warmed to 100° C. for 20 minutes in a microwave. The reaction was recharged with additional Pd(Ph$_3$P)$_4$ (0.37 mmol) and warmed for another 20 minutes. The reaction was then diluted with 1 N aqueous NaOH and the resulting solids were isolated by filtration (615 mg). The desired product was present in both the solids as well as the filtrate. The solids were purified by suspension in dimethylacetamide, filtration to remove insoluble material and reverse phase HPLC chromatography of the filtrate to afford the desired product as a white solid (62 mg, 46%). The aqueous filtrate from above was neutralized with 1 N aqueous HCl and the resulting crude product was isolated by filtration (233 mg). This additional material was used without further purification.

Example 4: Synthesis of 6-Amino-7-methoxy isoquinolin-1-one

-continued

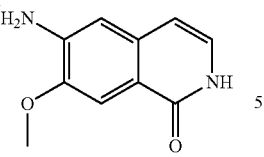

To a solution of 3-methoxy-4-nitrobenzoic acid (10.00 g, 50.72 mmol) in CH$_2$Cl$_2$ (250 mL) was added pyridine (4.89 mL, 60.87 mmol) followed by SOCl$_2$ (4.06 mL, 55.80 mmol). The reaction was stirred for 5 min then volatiles were removed in vacuo. The crude was dissolved in CH$_2$Cl$_2$ (200 mL) and a solution of triethylamine (8.72 mL, 60.87 mmol) and aminoacetaldehyde dimethyl acetal (6.40 g, 60.87 mmol) in CH$_2$Cl$_2$ (50 mL) was added via syringe. The mixture was stirred for 5 min then diluted with CH$_2$Cl$_2$ (250 mL), washed with saturated aqueous NaHCO$_3$ (2.times.200 mL), dried with MgSO$_4$, filtered, and concentrated to afford the crude product (14.0 g) which was used as is in the next transformation.

A solution of the above nitro compound (14.0 g) and 20% Pd(OH)$_2$ on carbon (1.8 g) was dissolved in MeOH (150 mL). A balloon filled with hydrogen was attached and the system was purged and evacuated (3×). The suspension was allowed to stir for 20 h then was filtered through a pad of diatomaceous earth. The filtrate was concentrated in vacuo to afford the desired aniline intermediate as a gold foam (12.25 g, 98%). MS (ES+) m/e 255 [M+H]$^+$.

A solution of the aniline (11.00 g, 43.26 mmol) in concentrated H$_2$SO4 (100 mL) was stirred at 100° C. for 1 h. The mixture was cooled to 0° C. and carefully treated with 6 M NaOH to pH=10. The aqueous mixture was extracted with EtOAc (5×300 mL), dried with MgSO$_4$, filtered, and concentrated to give a crude beige solid that was purified by suspending in CH$_2$Cl$_2$ (50 mL) and filtering the solid. The solid was dried to give the desired 6-amino-7-methoxy-isoquinolin-1-one (1.55 g, 19%). MS (ES+) m/e 191 [M+H]$^+$.

Example 5: Synthesis of 6-amino-5-chloro isoquinolin-1-one

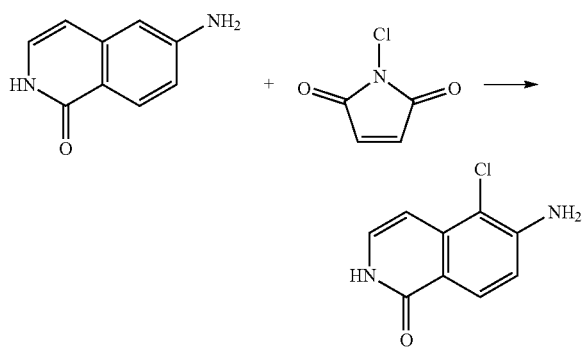

To a solution of 0.500 g (3.12 mmol) of 6-amino-2H-isoquinolin-1-one in DMF (30 mL) was added 0.45 g (3.4 mol) of N-chlorosuccinimide. The mixture was stirred at room temperature for 15 h then poured over ice and stirred until all the ice was melted during which time a solid precipitated from solution. The tan solid was collected by filtration, washed with water and dried on the filter pad to provide 0.50 g (82% yield) of the title compound. MS calc. for C$_9$H$_8$ClN$_2$O [M+H]$^+$; 195.63. Found: 195.23.

Example 7: Synthesis or 6-amino-7-chloro-5-fluoro-isoquinolin-1-one

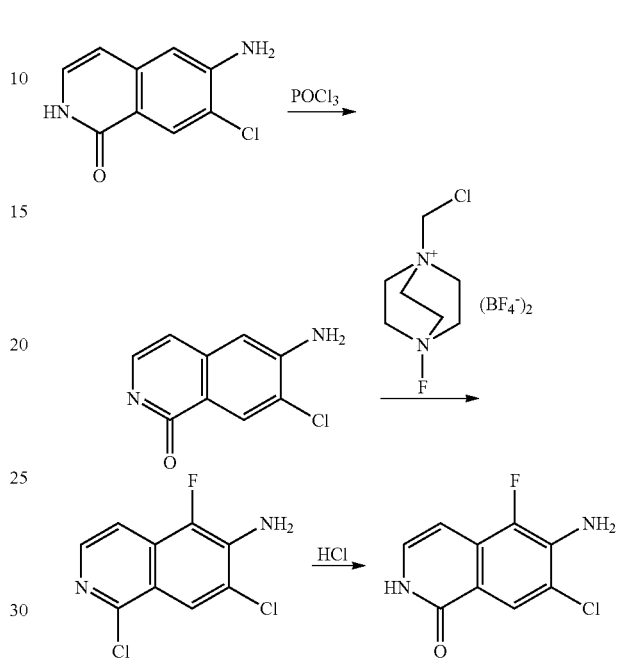

To 20.0 mL (215 mmol) of phosphorous oxychloride, cooled to 0° C., was added 5.00 g (25.7 mmol) of 6-amino-7-chloro-2H-isoquinolin-1-one in portions. The mixture was heated to 100° C. for 3 h then cooled to room temperature and poured over ice. After all of the ice had melted the pH of the mixture was adjusted to slightly alkaline by the slow addition of a 10% aqueous NaOH solution. A yellow solid precipitated from solution and was collected by filtration, washed with water and dried over anhydrous Na$_2$SO$_4$ to provide 3.0 g (55%) of 1,7-dichloro-isoquinolin-6-ylamine. MS calc. for C$_9$H$_7$Cl$_2$N$_2$[M+H]$^+$: 214.08. Found: 213.23 and 215.23.

To a solution of 2.62 g (12.3 mmol) of 1,7-dichloro-isoquinolin-6-ylamine in DMF (130 mL) was added 5.5 g (15.5 mmol) of Selectfluor® as a solid in one portion. The mixture was stirred at room temperature for 15 h. The mixture was poured over ice and stirred until all of the ice had melted during which time a solid precipitated from solution. The brown solid was collected by filtration, washed with water and dried on the filter pad to provide 1.0 g (60% by .sup.1H-NMR, 21%) of 1,7-dichloro-5-fluoro-isoquinolin-6-ylamine. MS calc. for C$_9$H$_5$Cl$_2$FN$_2$ [M]$^+$: 231.05. Found: 231.68.

A mixture of 1.0 g (4.3 mmol) of the above crude intermediate in 50 mL (100 mmol) of a 2 N solution of hydrochloric acid was heated at 100° C. for 15 h then cooled to room temperature. The pH of the solution was adjusted to slightly alkaline by the addition of a 10% NaOH solution. A solid precipitated from solution and was collected by filtration and dried on the filter pad. The residue was purified by flash silica gel chromatography using a 0-50% gradient of MeCN to hexanes to provide 0.15 g (16%) of the title compound. MS calc. for C$_9$H$_7$ClFN$_2$O [M+H]$^+$: 213.62. Found: 213.42.

Example 8: Synthesis of 7-aminoquinazolin-4-one

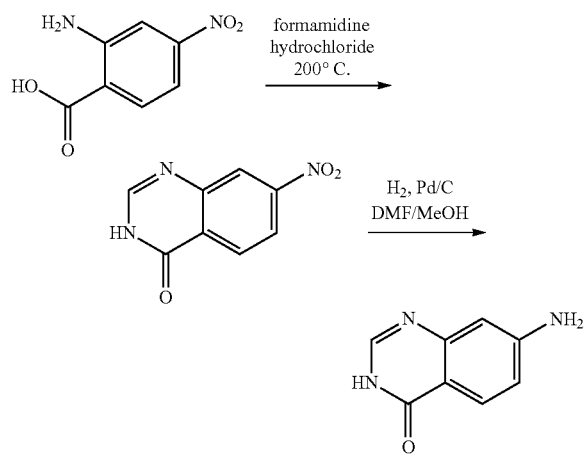

4-Nitroanthranilic acid (10.0 g. 54.9 mmol) and formamidine hydrochloride (6.63 g, 82.4 mmol) were ground together in a mortar and pestle to produce a fine, intimate mixture. The mixture was placed in a 250 mL round-bottom flask, and spread evenly over the surface. The flask was placed in an oil bath at 200° C. The solid underwent a color change, and a distillate was seen on the side of flask, but did not really melt. After 30 min the flask was removed from the heating bath. 0.3M sodium hydroxide solution (150 mL) was added to the cooled flask, the black solid mass was broken up with a spatula, and stirred for 1 h. The solid was filtered off and washed with water. The filtrate was discarded. The black solid was suspended in dichloromethane/methanol (10:1) and filtered through a plug of silica, eluting with the same solvent until no more product came off. The material was one spot by TLC, plus black baseline material, but was poorly soluble, so a large volume of solvent was needed. The filtrate was evaporated to dryness and the solid residue triturated with a little methanol and filtered to give 7-nitroquinazolin-4-one (4.65 g, 44%).

A suspension of 7-nitroquinazolinone (5.2 g, 22.7 mmol) in DMF (150 mL) and methanol (100 mL) was hydrogenated over 10% palladium on carbon (600 mg) in a Parr shaker at 50 psi. The starting material was consumed in 3 h, but hydrogenation was continued for 18 h to ensure complete reaction. The mixture was filtered through diatomaceous earth, washing with methanol/DMF 2:1 until all of the product was eluted. The filtrate was evaporated to dryness. The solid residue was stirred with methanol (20 mL) for 1 h, filtered, washed with methanol and dried to give the crude amine (3.88 g), which contained a minor component (ca. 10%). The crude product was dissolved in 2 N HCl (100 mL), with warming, and the resulting solution was evaporated to dryness to give the hydrochloride salt. The salt was dissolved in boiling water (30 mL) and ethanol (30 mL) was added. The solvent was boiled down to 50 mL. The hydrochloride crystallized on cooling. The crystals were filtered, washed with a little ethanol and dried to give the pure salt (3.02 g). The salt was dissolved in water (30 mL) with warming to 65° C. in an oil bath. Ammonium hydroxide was added dropwise, causing immediate precipitation of the free base. The flask was cooled in ice, the crystals filtered, washed with water and dried to give the title compound (2.35 g, 54%).

Example 9: Synthesis of 6-Chloro-7-aminoquinazolin-4-one

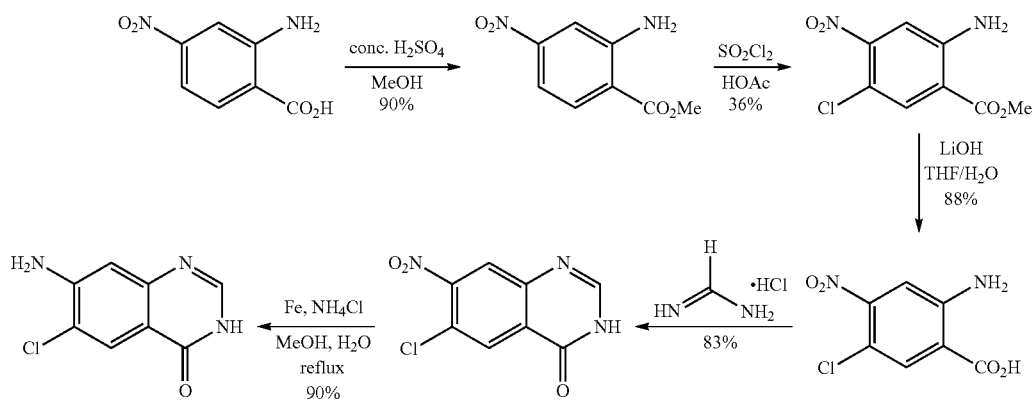

Methanol (500 mL) and concentrated $H_2SO_4$ (25 mL) were added to 4-nitroanthranilic acid (30.0 g, 165.0 mmol) and the reaction mixture was heated at reflux for 48 h. The resulting solution was concentrated and saturated $NaHCO_3$ (200 mL) was added. The aqueous layer was extracted with EtOAc (2.times.150 mL). The combined organic extracts were washed with water (100 mL), and brine (100 mL), dried over $Na_2SO$, filtered, and concentrated to give the methyl ester (29.0 g, 90%) as an intense orange solid.

To a suspension of 4-nitroanthranilic acid methyl ester (16.5 g, 84 mmol) in glacial acetic acid (500 mL), a solution of sulfuryl chloride (13.6 g, 0.1 mol) in glacial acetic acid (20 mL) was added dropwise. The homogeneous mixture was stirred at room temperature for 18 h and the solvent was evaporated in vacuo. The residue was dissolved in $CH_2Cl_2$ (200 mL) and washed with saturated $NaHCO_3$ (100 mL) and water (100 mL). The organic layer was dried over $Na_2SO_4$, filtered, and concentrated. The $^1H$ NMR spectrum of the crude compound revealed the formation of a mixture of products, namely the desired 5-chloro regioisomer, and the byproducts 3-chloro regioisomer and the 3,5-dichlorinated compound. The crude mixture was purified by flush chromatography (silica gel, gradient 30-100% hexanes/CH₂Cl₂) to afford the desired 5-Chloro-4-nitroanthranilic acid methyl ester (7.1 g, 36%) as a pale yellow solid.

To a solution of 5-chloro-4-nitroanthranilic acid methyl ester (10.0 g, 43 mmol) in THF (120 mL) was added LiOH (2.7 g, 65 mmol) dissolved in water (40 mL). The reaction mixture was stirred at room temperature for 18 h and acidified to pH .about.4 with 1 N HCl. The aqueous layer was extracted with EtOAc (2.times.150 mL); the combined organic layers were dried over Na₂SO₄, filtered, and concentrated to give 5-chloro-4-nitroanthranilic acid (8.7 g, 88%) as an orange solid.

A mixture of 5-chloro-4-nitroanthranilic acid (8.7 g, 0.040 mol) and formamidine hydrochloride (4.9 g, 60 mmol) were ground to a fine, intimate powder using a mortar and pestle. The mixture was transferred into a 250 mL round bottomed flask and immersed in an oil bath maintained at 205° C. After 40 min, LCMS analysis of the reaction mixture showed mass corresponding to the product. The reaction mixture was cooled and the crude product was crushed into pieces and washed several times with saturated NaHCO₃ (300 mL) and water (200 mL). The solid was air dried and triturated with a minimum amount of MeOH (20 mL) to obtain 6-chloro-7-nitroquinazolin-4-one (7.6 g, 83%) as a tan powder.

To a suspension of 6-chloro-7-nitroquinazolin-4-one (7.5 g, 33 mmol) in MeOH (250 mL) was added NH₄Cl (17.7 g, 0.33 mol) dissolved in water (75 mL). Iron powder (18.5 g, 330 mmol) was added and the suspension was heated at 65° C. for 2 h. The warm reaction mixture was filtered over diatomaceous earth and washed several times with THF (1 L) and methanol (500 mL). The filtrate was concentrated, washed with water and dried under vacuum at 50° C. to afford the title compound (6.5 g, 90%) as a brown solid. ESI-MS m/z 196 [C₈H₆ClN₃O+H]⁺.

Example 10: Parallel Synthesis of Amides of Formula (I). Method 1

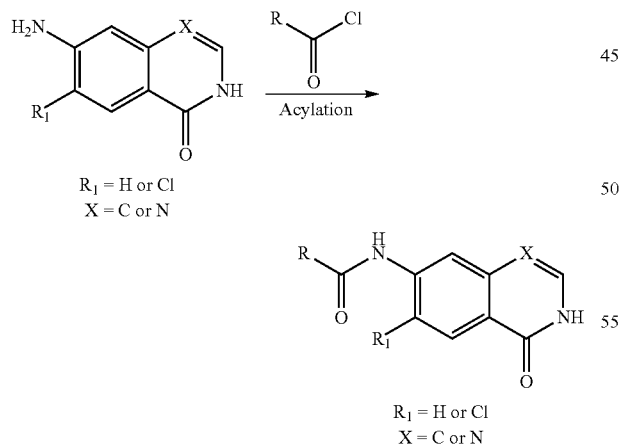

R₁ = H or Cl
X = C or N

Intermediates from Examples 1-4 were acylated with a variety of acid chlorides as follows: Acid chlorides were dissolved in dimethylacetamide (DMA) to give a 0.67 mM solution. The amine intermediates were dissolved in DMA to give a 0.171 mM solution. 150 microL (100 micromol) of acid chloride solution was transferred to each well of a deep-well microtitre plate. 350 microL (60 micromol) of the appropriate amine solution was added to each well. The plate was sealed and placed on a shaker for 24 h. Silica-bound amine scavenger (about 50 mg) was added to each well, and the plate was shaken for 30 min. Silica-bound carbonate scavenger (about 125 mg) was added to each well, and the plates were shaken for a further 20 h. The contents of the plate were transferred to a filter plate and filtered into a fresh deep-well plate. The scavenger was washed with two 400 microL portions of DMA. Aliquots were removed from each well for LCMS analysis. The solutions were evaporated in a Genevac. The purity was assessed by UV at 240 nm. Samples below 80% purity were purified by preparative HPLC.

Example 11: Synthesis of N-(7-Chloro-1-oxo-1,2-dihydro-isoquinolin-6-yl)-2-cyclopropylamino-2-phen-yl-acetamide. Method 2

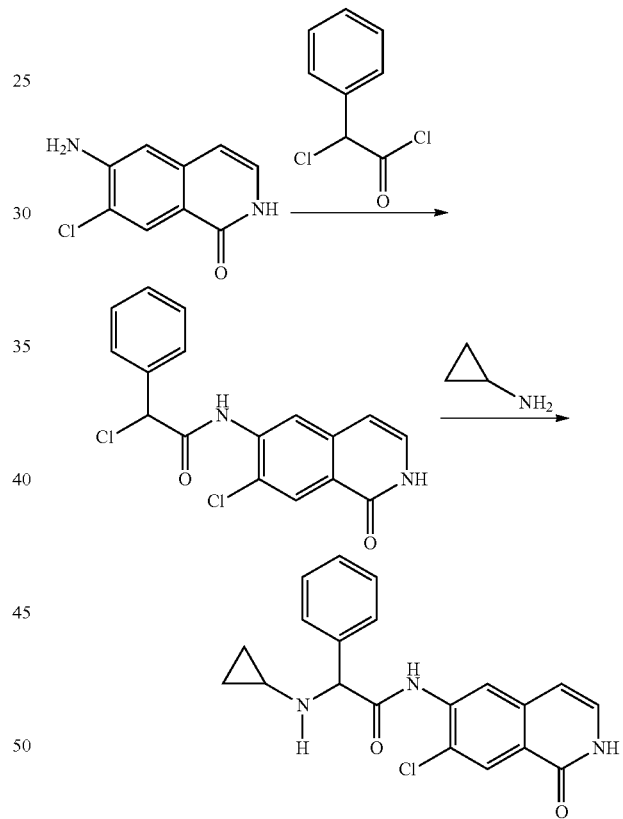

7-Chloro, 6-aminoisoquinolone (25 mg, 0.13 mmol) was dissolved in DMF. 2-Chlorophenylacetyl chloride (1.2 eq, 22 microL, 0.15 mmol) was added followed by diisopropylethylamine (2 eq., 45 microL, 0.26 mmol). The reaction mixture was shaken for 3 hr on a reaction block at 75° C. This crude mixture was carried on to the next step without purification.

The crude reaction mixture from the previous step was taken as is and excess cyclopropylamine (100 microL, 11 eq.) was added. The reaction mixture was shaken on a reaction block for 16 hr at 75° C. This crude reaction mixture was purified directly as is on preparative LC-MS. N-(7-Chloro-1-oxo-1,2-dihydro-isoquinolin-6-yl)-2-cyclopropylamino-2-phen-yl-acetamide (21 mg, 0.05 mmol) was isolated as an amorphous solid in 40% yield. ES+=368.

Example 12: Synthesis of 2-amino-N-(7-chloro-1-oxo-1,2-dihydro-isoquinolin-6-yl)-3-phenyl-propionamide. Method 3

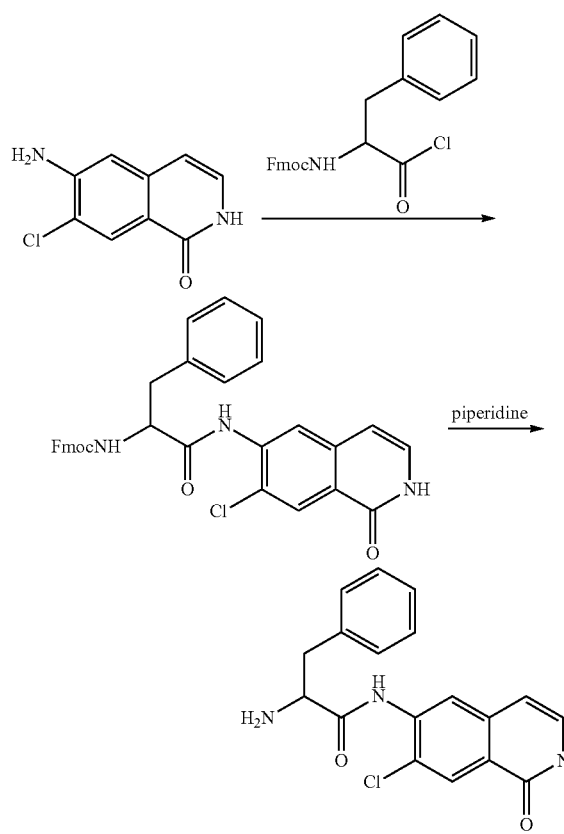

6-Amino-7-chloro-2H-isoquinolin-1-one (0.2 mmol, 39 mg) and L-Fmoc-2-amino-3-phenyl-propionyl chloride (0.2 mmol, 81 mg) were dissolved in 3 mL DMF. The mixture was allowed to stir at room overnight. HPLC-MS confirmed the product had formed. The crude product was carried on to the next step without further purification. MS (M+1) 565.

The above crude product in DMF was treated with piperidine (5-10% total concentration), and the reaction mixture was allowed to stir at room overnight. The title compound was obtained after prep-HPLC purification. MS (M+1) 342.

Example 13: Synthesis of 1-benzyl-3-(1-oxo-1,2-dihydro-isoquinolin-6-yl)-urea. Method 4

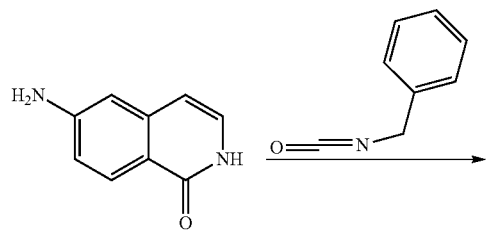

-continued

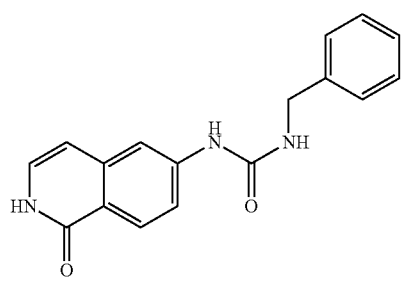

6-Amino-2H-isoquinolin-1-one (0.2 mmol, 39 mg) and benzyl isocyanate (0.2 mmol, 27 mg) were dissolved in 1 mL DMA. The mixture was allowed to stir at 60° C. overnight. The product was obtained by HPLC purification. MS (M+1) 294.

Example 14: Synthesis of 4-(4-chloro-phenyl)-pyrrolidine-3-carboxylic acid (7-chloro-1-oxo-1,2-dihydro-isoquinolin-6-yl)-amide

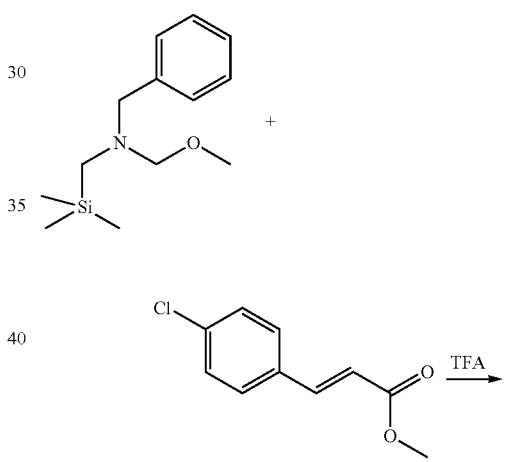

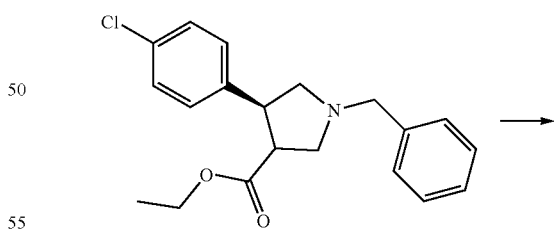

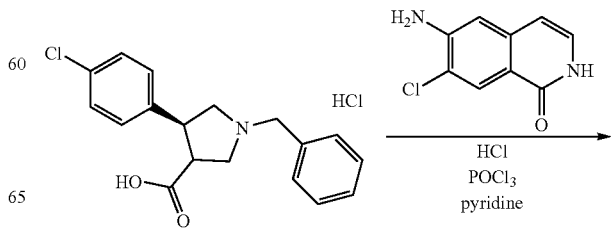

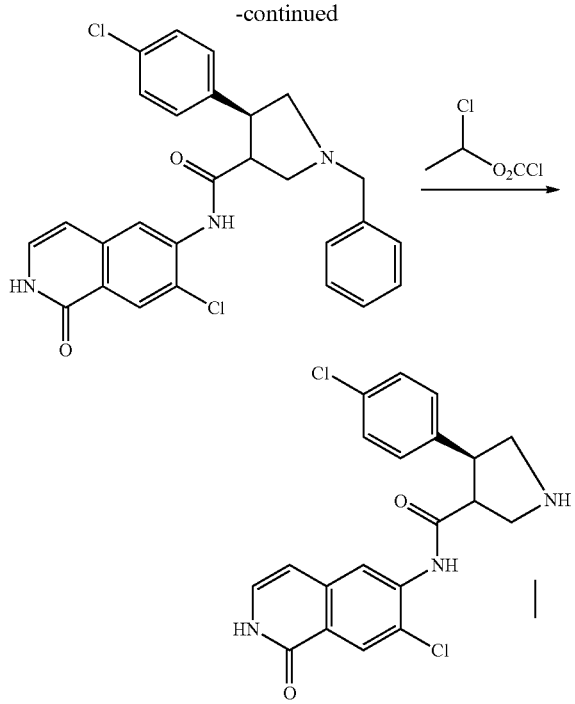

To a solution of benzyl-methoxymethyl-trimethylsilanyl-methyl-amine (2.05 mL, 8.0 mmol) and (E)-3-(4-chloro-phenyl)-acrylic acid methyl ester (1.57 g, 8.0 mmol) in dichloromethane (16 mL) was added TFA (275 mg, 2.4 mmol). The mixture was stirred at 23° C. for 30 min then treated with saturated aqueous NaHCO₃ (20 mL), extracted with dichloromethane (2×50 mL), dried with MgSO₄, filtered, and concentrated. Purification of the crude by flash chromatography (SiO₂, hexane to 1:1 hexane:EtOAc) gave (trans)-1-benzyl-4-(4-chloro-phenyl)-pyrrolidine-3-carboxylic acid ethyl ester (2.11 g, 80%).

A solution of the ester from above (1.01 g, 2.94 mmol) in MeOH (15 mL) and THF (5 mL) was treated with a 6 M aqueous NaOH solution (4.9 mL, 29.4 mmol) and heated at reflux for 2 h. The mixture was then acidified to pH=1 with 6 M aqueous HCl, extracted with dichloromethane, dried with MgSO₄, filtered, and concentrated to afford 1-benzyl-4-(4-chloro-phenyl)-pyrrolidine-3-carboxylic acid as the HCl salt (1.00 g, 97%).

To a solution of the acid from above (1.06 g, 3.0 mmol) and 6-amino-5-chloroisoquinolin-1-one (450 mg, 2.3 mmol) in pyridine (5 mL) was added POCl₃ (320 μL, 3.5 mmol). The mixture was stirred for 1 h then treated with water, extracted with EtOAc, dried with MgSO₄, filtered, and concentrated to afford 1-benzyl-4-(4-chloro-phenyl)-pyrrolidine-3-carboxylic acid (7-chloro-1-oxo-1,2-dihydro-isoquinolin-6-yl)-amide (454 mg, 40%).

The above N-benzyl pyrrolidine (216 mg, 0.44 mmol) was dissolved in dichloroethane (5 mL) and treated with alpha chloroethyl chloroformate (95 microL, 0.88 mmol) followed by proton sponge (69 mg, 0.44 mmol). The mixture was stirred at 23° C. for 1 h then heated at reflux for 3 h. The mixture was then concentrated in vacuo, diluted with MeOH (10 mL), and heated at reflux for 2 h. The solution was concentrated in vacuo then purified by RP HPLC to afford the desired product as the TFA salt (88 mg, 40%) MS MH+=402.3

The following compounds were also prepared using the methods described in the General Synthetic Methods section and the synthetic examples above:

| Name | MH+ |
|---|---|
| N-(7-Chloro-1-oxo-1,2-dihydro-isoquinolin-6-yl)-2-dimethylamino-2-phenyl-acetamide | 357 |
| N-(7-Chloro-1-oxo-1,2-dihydro-isoquinolin-6-y1)-2-(4-methyl-piperazin-1-yl)-acetamide | 336 |
| N-(7-Chloro-1-oxo-1,2-dihydro-isoquinolin-6-y1)-2-(cyclohexylmethyl-amino)-acetamide | 349 |
| N-(7-Chloro-1-oxo-1,2-dihydro-isoquinolin-6-y1)-2-(4-hydroxy-piperidin-1-yl)-2-phenyl-acetamide | 413 |
| 2-Senzylamino-N-(7-chloro-1-oxo-1,2-dihydro-isoquinolin-6-yl)-2-phenyl-acetamide | 419 |
| N-(7-Chloro-1-oxo-1,2-dihydro-isoquinolin-6-yl)-2-thiomorpholin-4-yl-propionamide | 353 |
| N-(7-Chloro-1-oxo-1,2-dihydro-isoquinolin-6-y1)-2-(1,2,3,4-tetrahydro-naphthalen-l-ylamino)-acetamide | 383 |
| N-(7-Chloro-1-oxo-1,2-dihydro-isoquinolin-6-y1)-2-(2-thiophen-2-yl-ethylamino)-propionamide | 377 |
| N-(7-Chloro-1-oxo-1,2-dihydro-isoquinolin-6-yl)-2-methylamino-2-phenyl-acetamide | 343 |
| N-(7-Chloro-1-oxo-1,2-dihydro-isoquinolin-6-yl)-2-(ethyl-methyl-amino)-2-phenyl-acetamide | 371 |
| (S)-2-Amino-N-(7-chloro-1-oxo-1,2-dihydro-isoquinolin-6-yl)-3-phenyl-propionamide | 343 |
| (R)-2-Amino-N-(7-chloro-1-oxo-1,2-dihydro-isoquinolin-6-yl)-3-phenyl-propionamide | 343 |
| (R)-2-Amino-N-(7-chloro-1-oxo-1,2-dihydro-isoquinolin-6-yl)-2-phenyl-acetamide | 329 |
| N-(7-Chloro-1-oxo-1,2-dihydro-isoquinolin-6-yl)-2-cyclobutyl-amino-2-phenyl-acetamide | 383 |
| N-(7-Chloro-1-oxo-1,2-dihydro-isoquinolin-6-yl)-2-(cyclo-propylmethyl-amino)-2-phenyl-acetamide | 383 |
| N-(7-Chloro-1-oxo-1,2-dihydro-isoquinolin-6-yl)-2-(3-ethoxy-propylamino)-2-phenyl-acetamide | 415 |
| N-(7-Chloro-1-oxo-1,2-dihydro-isoquinolin-6-yl)-2-[(2-dimethylamino-ethyl)-ethyl-amino]-2-phenyl-acctamide | 428 |
| N-(7-Chloro-1-oxo-1,2-dihydro-isoquinolin-6-yl)-2-[(tetra-hydro-pyran-4-ylmethyl)-amino]-acetamide | 351 |

-continued

| Name | MH+ |
|---|---|
| 2-(Adamantan-1-ylamino)-N-(7-chloro-1-oxo-1,2-dihydro-isoquinolin-6-yl)-acetamide | 387 |
| N-(7-Chloro-1-oxo-1,2-dihydro-isoquinolin-6-yl)-2-[(pyridin-2-ylmethyl)-amino]-acetamide | 344 |
| N-(7-Chloro-1-oxo-1,2-dihydro-isoquinolin-6-yl)-2-[(pyridin-3-ylmethyl)-amino]-acetamide | 344 |
| N-(7-Chloro-1-oxo-1,2-dihydro-isoquinolin-6-yl)-2-[(pyridin-4-ylmethyl)-amino]-acetamide | 344 |
| N-(7-Chloro-1-oxo-1,2-dihydro-isoquinolin-6-yl)-2-(cyclohexyl-methyl-amino)-acetamide | 349 |
| N-(7-Chloro-1-oxo-1,2-dihydro-isoquinolin-6-yl)-2-methylamino-propionamide | 281 |
| 2-Dimethylamino-N-(1-oxo-1,2-dihydro-isoquinolin-6-yl)-acetamide | 246 |
| 2-(Cyclohexylmethyl-amino)-N-(1-oxo-1,2-dihydro-isoquinolin-6-yl)-acetamide | 314 |
| 2-Dimethylamino-N-(1-oxo-1,2-dihydro-isoquinolin-6-yl)-2-phenyl-acetamide | 322 |
| Acetic acid (7-chloro-1-oxo-1,2-dihydro-isoquinolin-6-ylcarbamoyl)-phenyl-methyl ester | 372 |
| N-(7-Chloro-1-oxo-1,2-dihydro-isoquinolin-6-yl)-2-hydroxy-2-phenyl-acetamide | 330 |
| (R)-2-Amino-N-(1-oxo-1,2-dihydro-isoquinolin-6-yl)-2-phenyl-acetamide | 294 |
| N-(7-Chloro-1-oxo-1,2-dihydro-isoquinolin-6-yl)-2-(4-chloro-phenyl)-3-methyl-butyramide | 390 |
| 2,5-Dichloro-thiophene-3-carboxylic acid (1-oxo-1,2-dihydro-isoquinolin-6-yl)-amide | 340 |
| N-(1-Oxo-1,2-dihydro-isoquinolin-6-yl)-2-phenylsulfanyl-nicotinamide | 374 |
| 2-(3-Methoxy-phenyl)-N-(1-oxo-1,2-dihydro-isoquinolin-6-yl)-acetamide | 309 |
| 2-(4-Chloro-phenoxy)-N-(1-oxo-1,2-dihydro-isoquinolin-6-yl)-nicotinamide | 393 |
| 2-(4-Chloro-phenoxy)-2-methyl-N-(1-oxo-1,2-dihydro-isoquinolin-6-yl)-propionamide | 358 |
| N-(1-Oxo-1,2-dihydro-isoquinolin-6-yl)-succinamic acid ethyl ester | 289 |
| Thiophene-2-carboxylic acid (1-oxo-1,2-dihydro-isoquinolin-6-yl)-amide | 271 |
| 1-(4-Chloro-phenyl)-cyclopentanecarboxylic acid (1-oxo-1,2-dihydro-isoquinolin-6-yl)-amide | 368 |
| 2-(4-Chlorophenoxy)-N-(1-oxo-1,2-dihydro-isoquinolin-6-yl)-acetamide | 330 |
| N-(7-Chloro-1-oxo-1,2-dihydro-isoquinolin-6-yl)-2-methyl-benzamide | 314 |
| N-(7-Chloro-1-oxo-1,2-dihydro-isoquinolin-6-yl)-2-phenyl-acetamide | 314 |
| N-(7-Chloro-1-oxo-1,2-dihydro-isoquinolin-6-yl)-2,3,6-trifluoro-benzamide | 354 |
| N-(7-Chloro-1-oxo-1,2-dihydro-isoquinolin-6-yl)-5-fluoro-2-methyl-benzamide | 332 |
| 2-Chloro-N-(7-chloro-1-oxo-1,2-dihydro-isoquinolin-6-yl)-4-nitro-benzamide | 379 |
| 2-Bromo-N-(7-chloro-1-oxo-1,2-dihydro-isoquinolin-6-yl)-benzamide | 379 |
| N-(7-Chloro-1-oxo-1,2-dihydro-isoquinolin-6-yl)-2-(4-fluoro-phenyl)-acetamide | 332 |
| N-(7-Chloro-1-oxo-1,2-dihydro-isoquinolin-6-yl)-2,2-dimethyl-propionamide | 280 |
| N-(7-Chloro-1-oxo-1,2-dihydro-isoquinolin-6-yl)-3,3-dimethyl-butyramide | 294 |
| N-(7-Chloro-1-oxo-1,2-dihydro-isoquinolin-6-yl)-2-phenylsulfanyl-nicotinamide | 409 |
| 2,4-Dichloro-N-(7-chloro-1-oxo-1,2-dihydro-isoquinolin-6-yl)-benzamide | 369 |
| 5-Methyl-3-phenyl-isoxazole-4-carboxylic acid (7-chloro-1-oxo-1,2-dihydro-isoquinolin-6-yl)-amide | 381 |
| N-(7-Chloro-1-oxo-1,2-dihydro-isoquinolin-6-yl)-2,4,6-trifluoro-benzamide | 354 |
| 1-(4-Chloro-phenyl)-cyclopentanecarboxylic acid (4-oxo-3,4-dihydro-quinazolin-7-yl)-amide | 368 |
| Piperidine-4-carboxylic acid (4-oxo-3,4-dihydro-quinazolin-7-yl)-amide | 273 |
| 2-Benzylamino-N-(4-oxo-3,4-dihydro-quinazolin-7-yl)-acetamide | 309 |
| 1-Benzyl-piperidine-4-carboxylic acid (4-oxo-3,4-dihydro-quinazolin-7-yl)-amide | 3b3 |
| Piperidine-3-carboxylic acid (4-oxo-3,4-dihydro-quinazolin-7-yl)-amide | 273 |
| Pyrrolidine-2-carboxylic acid (4-oxo-3,4-dihydro-quinazolin-7-yl)-amide | 259 |
| 2-Amino-4-methyl-pentanoic acid (4-oxo-3,4-dihydro-quinazolin-7-yl)-amide | Z75 |

| Name | MH+ |
|---|---|
| (R)-2-Amino-N-(4-oxo-3,4-dihydro-quinazolin-7-yl)-3-phenyl-propionamide | 309 |
| (S)-2-Amino-N-(4-oxo-3,4-dihydro-quinazolin-7-yl)-3-phenyl-propionamide | 309 |
| 2-(Cyclohexylmethyl-amino)-N-(4-oxo-3,4-dihydro-quinazolin-7-yl)-acetamide | 315 |
| 2-Methylamino-N-(4-oxo-3,4-dihydro-quinazolin-7-yl)-2-phenyl-acetamide | 309 |
| 2-Amino-N-(4-oxo-3,4-dihydro-quinazolin-7-yl)-2-phenyl-acctamide | 295 |
| 2-Cyclopropylamino-N-(4-oxo-3,4-dihydro-quinazolin-7-yl)-2-phenyl-acctamide | 335 |
| (R)-2-Amino-N-(4-oxo-3,4-dihydro-quinazolin-7-yl)-2-phenyl-acctamide | 295 |
| (R)-Pyrrolidine-2-carboxylic acid (4-oxo-3,4-dihydro-quinazolin-7-yl)-amide | 259 |
| (R)-2-Amino-3-methyl-N-(4-oxo-3,4-dihydro-quinazolin-7-y1)-butyrarnide | 261 |
| 2-(Cyclopropylmethyl-amino)-N-(4-oxo-3,4-dihydro-quinazolin-7-yl)-acetamide | 273 |
| N-(4-Oxo-3,4-dihydro-quinazolin-7-yl)-2-(2-thiophen-2-yl-ethylamino)-acctamide | 329 |
| 2-(Cyclohexyl-methyl-amino)-N-(4-oxo-3,4-dihydro-quinazolin-7-yl)-acetamide | 315 |
| N-(6-Chloro-4-oxo-3,4-dihydro-quinazolin-7-yl)-2-dimethylamino-2-phenyl-acctamide | 357 |
| N(6-Chloro-4-oxo-3,4-dihydro-quinazolin-7-yl)-2-cyclopropylamino-2-phenyl-acetamide | 369 |
| 2,5-Dimethyl-2H-pyrazole-3-carboxylic acid (4-oxo-3,4-dihydro-quinazolin-7-yl)-amide | 284 |
| 2-Amino-N-(7-chloro-1-oxo-1,2-dihydro-isoquinolin-6-yl)-3-(4-fluoro-phenyl)-propionamide | 360 |
| (R)-2-Amino-2-cyclohexyl-N-(1-oxo-1,2-dihydro-isoquinolin-6-yl)-acetamide | 300 |
| (R)-2-Amino-2-(4-chloro-phenyl)-N-(1-oxo-1,2-dihydro-isoquinolin-6-yl)-acetamide | 362 |
| (R)-Pyrrolidine-2-carboxylic acid (7-chloro-1-oxo-1,2-dihydro-isoquinolin-6-yl)-amide | 292 |
| (S)-Pyrrolidine-2-carboxylic acid (7-chloro-1-oxo-1,2-dihydro-isoquinolin-6-yl)-amide | 292 |
| 2-Amino-N-(7-chloro-1-oxo-1,2-dihydro-isoquinolin-6-yl)-acetamide | 252 |
| Piperidine-4-carboxylic acid (7-chloro-1-oxo-1,2-dihydro-isoquinolin-6-yl)-amide, | 306 |
| (R)-2-Amino-N-(7-chloro-1-oxo-1,2-dihydro-isoquinolin-6-yl)-3-(4-chloro-phenyl)-propionamide | 376 |
| (R)-2-Amino-N-(7-chloro-1-oxo-1,2-dihydro-isoquinolin-6-yl)-2-p-tolyl-acetamide | 342 |
| (S)-2-Amino-N-(7-chloro-1-oxo-1,2-dihydro-isoquinolin-6-yl)-3-cyclohexyl-propionamide | 348 |
| (R)-2-Amino-N-(7-chloro-1-oxo-1,2-dihydro-isoquinolin-6-yl)-3-cyclohexyl-propionamide | 348 |
| (R)-2-Amino-4,4-dimethyl-pentanoic acid (7-chloro-1-oxo-1,2-dihydro-isoquinolin-6-yl)-amide | 322 |
| (S)-2-Amino-4,4-dimethyl-pentanoic acid (7-chloro-1-oxo-1,2-dihydro-isoquinolin-6-yl)-amide | 322 |
| 2-Chloro-N-(7-chloro-1-oxo-1,2-dihydro-isoquinolin-6-yl)-4-methanesulfonyl-benzamide | 411 |
| 2-Chloro-N(7-chloro-1-oxo-1,2-dihydro-isoquinolin-6-yl)-4-rnorpholin-4-yl-benzamide | 418 |
| (R)-2-Amino-N-(7-chloro-1-oxo-1,2-dihydro-isoquinolin-6-yl)-3-naphthalen-2-yl-propionamide | 392 |
| (R)-2-Amino-N-(7-chloro-1-oxo-1,2-dihydro-isoquinolin-6-yl)-3-naphthalen-1-yl-propionamide | 392 |
| (R)-2-Amino-N-(7-chloro-1-oxo-1,2-dihydro-isoquinolin-6-yl)-3-pyridin-4-yl-propionamide | 343 |
| 2-Methyl-2-methylamino-N-(1-oxo-1,2-dihydro-isoquinolin-6-yl)-propionamide | 260 |
| 2-Amino-2-methyl-N-(1-oxo-1,2-dihydro-isoquinolin-6-yl)-propionamide | 246 |
| (R)-N-(7-Chloro-1-oxo-1,2-dihydro-isoquinolin-6-yl)-2-methoxy-2-phenyl-acetamide | 343 |
| (S)-N-(7-Chloro-1-oxo-1,2-dihydro-isoquinolin-6-yl)-2-methoxy-2-phenyl-acetamide | 343 |
| 3-Amino-N-(7-chloro-1-oxo-1,2-dihydro-isoquinolin-6-yl)-propionamide | 266 |
| (R)-2-Amino-N-(7-chloro-1-oxo-1,2-dihydro-isoquinolin-6-yl)-3-methyl-butyramide | 294 |

-continued

| Name | MH+ |
|---|---|
| N-(7-Chloro-1-oxo-1,2-dihydro-isoquinolin-6-yl)-3,3,3-trifluoro-2-methoxy-2-phenyl-propionamide | 411 |
| N-(7-Chloro-1-oxo-1,2-dihydro-isoquinolin-6-yl)-2-oxo-2-phenyl-acetamide | 327 |
| (R)-Piperidine-2-carboxylic acid (7-chloro-1-oxo-1,2-dihydro-isoquinolin-6-yl)-amide | 306 |
| 2-tert-Butylamino-N-(7-chloro-1-oxo-1,2-dihydro-isoquinolin-6-yl)-acetamide | 308 |
| (R)-2-Methoxy-N-(7-methoxy-1-oxo-1,2-dihydro-isoquinolin-6-yl)-2-phenyl-acetamide | 339 |
| (S)-2-Methoxy-N-(7-methoxy-1-oxo-1,2-dihydro-isoquinolin-6-yl)-2-phenyl-acetamide | 339 |
| (R)-2-Amino-2-cyclohexyl-N-(7-methoxy-1-oxo-1,2-dihydro-isoquinolin-6-yl)-acetamide | 330 |
| (S)-2-Amino-2-cyclohexyl-N-(7-methoxy-1-oxo-1,2-dihydro-isoquinolin-6-yl)-acetamide | 330 |
| 4-Bromo-2-chloro-N-(7-chloro-1-oxo-1,2-dihydro-isoquinolin-6-yl)-benzamide | 413 |
| 2-Chloro-N-(7-chloro-1-oxo-1,2-dihydro-isoquinolin-6-yl)-5-methanesulfonyl-benzamide | 412 |
| (R)-Tetrahydro-furan-2-carboxylic acid (7-chloro-1-oxo-1,2-dihydro-isoquinolin-6-yl)-amide | 293 |
| (S)-N-(7-Chloro-1-oxo-1,2-dihydro-isoquinolin-6-yl)-2-hydroxy-2-phenyl-acetamide | 329 |
| (R)-N-(7-Chloro-1-oxo-1,2-dihydro-isoquinolin-6-yl)-2-hydroxy-2-phenyl-acetamide | 329 |
| N-(7-Chloro-1-oxo-1,2-dihydro-isoquinolin-6-yl)-2-cyano-benzamide | 324 |
| N-(7-Chloro-1-oxo-1,2-dihydro-isoquinolin-6-yl)-2-methyl-4-nitro-benzamide | 358 |
| N-(7-Chloro-1-oxo-1,2-dihydro-isoquinolin-6-yl)-4-nitro-2-trifluoromethyl-benzamide | 412 |
| N-(7-Chloro-1-oxo-1,2-dihydro-isoquinolin-6-yl)-2-morpholin-4-ylmethyl-benzamide | 398 |
| 1-Amino-cyclohexanecarboxylic acid (1-oxo-1,2-dihydro-isoquinolin-6-yl)-amide | 286 |
| (R)-2-Amino-N-(7-chloro-1-oxo-1,2-dihydro-isoquinolin-6-yl)-2-cyclohexyl-acetamide | 334 |
| (R)-2-Amino-4-methyl-pentanoic acid (7-chloro-1-oxo-1,2-dihydro-isoquinolin-6-yl)-amide | 308 |
| (S)-2-Amino-N-(7-chloro-1-oxo-1,2-dihydro-isoquinolin-6-yl)-2-cyclohexyl-acetamide | 334 |
| (S)-2-Amino-4-methyl-pentanoic acid (7-chloro-1-oxo-1,2-dihydro-isoquinolin-6-yl)-amide | 308 |
| (S)-2-Amino-N-(7-chloro-1-oxo-1,2-dihydro-isoquinolin-6-yl)-3-methyl-butyramide | 294 |
| N-(7-Chloro-1-oxo-1,2-dihydro-isoquinolin-6-yl)-2-(4-methyl-piperazin-1-ylmethyl)-benzamide | 411 |
| 1,2,3,4-Tetrahydro-isoquinoline-5-carboxylic acid (7-chloro-1-oxo-1,2-dihydro-isoquinolin-6-yl)-amide | 354 |
| 1,2,3,4-Tetrahydro-isoquinoline-8-carboxylic acid (7-chloro-1-oxo-1,2-dihydro-isoquinolin-6-yl)-amide | 354 |
| 1-Methyl-piperidine-4-carboxylic acid (7-chloro-1-oxo-1,2-dihydro-isoquinolin-6-yl)-amide | 320 |
| (R)-N-(7-Chloro-1-oxo-1,2-dihydro-isoquinolin-6-yl)-3-methyl-succinamic acid methyl ester | 323 |
| 2-Chloro-N-(7-chloro-1-oxo-1,2-dihydro-isoquinolin-6-yl)-3-nitro-benzamide | 378 |
| 2-Chloro-N-(7-chloro-1-oxo-1,2-dihydro-isoquinolin-6-yl)-5-nitro-benzamide | 378 |
| (S)-Tetrahydro-furan-2-carboxylic acid (7-chloro-1-oxo-1,2-dihydro-isoquinolin-6-yl)-amide | 293 |
| N-(7-Chloro-1-oxo-1,2-dihydro-isoquinolin-6-yl)-3-methylsulfanyl-propionamide | 297 |
| N-(7-Chloro-1-oxo-1,2-dihydro-isoquinolin-6-yl)-2-cyano-acetamide | 262 |
| 2-Bromo-N-(7-chloro-1-oxo-1,2-dihydro-isoquinolin-6-yl)-4-methyl-benzamide | 392 |
| Tetrahydro-pyran-4-carboxylic acid (7-chloro-1-oxo-1,2-dihydro-isoquinolin-6-yl)-amide | 307 |
| N-(7-Chloro-1-oxo-1,2-dihydro-isoquinolin-6-yl)-3-phenyl-succinamic acid | 371 |
| N-(7-Chloro-1-oxo-1,2-dihydro-isoquinolin-6-yl)-malonamic acid ethyl ester | 309 |
| N-(7-Chloro-1-oxo-1,2-dihydro-isoquinolin-6-yl)-2-methylsulfanyl-acetamide | 283 |
| (S)-Pyrrolidine-3-carboxylic acid (7-chloro-1-oxo-1,2-dihydro-isoquinolin-6-yl)-amide | 292 |

-continued

| Name | MH+ |
|---|---|
| (S)-Piperidine-3-carboxylic acid (7-chloro-1-oxo-1,2-dihydro-isoquinolin-6-yl)-amide | 306 |
| (R)-Piperidine-3-carboxylic acid (7-chloro-1-oxo-1,2-dihydro-isoquinolin-6-yl)-amide | 306 |
| N-(7-Chloro-1-oxo-1,2-dihydro-isoquinolin-6-yl)-2-methanesulfonyl-acetamide | 315 |
| N-(7-Chloro-1-oxo-1,2-dihydro-isoquinolin-6-yl)-2-phenyl-malonamic acid | 357 |
| (S)-Piperidine-2-carboxylic acid (7-chloro-1-oxo-1,2-dihydro-isoquinolin-6-yl)-amide | 306 |
| 1-Methanesulfonyl-4-methyl-piperidine-4-carboxylic acid (7-chloro-1-oxo-1,2-dihydro-isoquinolin-6-yl)-amide | 398 |
| 2-Chloro-N(7-chloro-1-oxo-1,2-dihydro-isoquinolin-6-yl)-4-nitro-benzamide | 378 |
| N-(7-Chloro-1-oxo-1,2-dihydro-isoquinolin-6-yl)-4-methanesulfonyl-benzamide | 377 |
| (R)-Pyrrolidine-3-carboxylic acid (7-chloro-1-oxo-1,2-dihydro-isoquinolin-6-yl)-amide | 292 |
| 4-Amino-cyclohexanecarboxylic acid (7-chloro-1-oxo-1,2-dihydro-isoquinolin-6-yl)-amide | 320 |
| 4-(7-Chloro-1-oxo-1,2-dihydro-isoquinolin-6-ylcarbamoyl)-cyclohexanecarboxylic acid | 349 |
| (R)-N-(7-Chloro-1-oxo-1,2-dihydro-isoquinolin-6-yl)-2-isopropoxy-2-phenyl-acetamide | 371 |
| (R)-N-(7-Chloro-1-oxo-1,2-dihydro-isoquinolin-6-yl)-2-phenoxy-propionamide | 343 |
| (S)-N-(7-Chloro-1-oxo-1,2-dihydro-isoquinolin-6-yl)-2-phenoxy-propionamide | 343 |
| 4-Phenyl-piperidine-4-carboxylic acid (7-chloro-1-oxo-1,2-dihydro-isoquinolin-6-yl)-amide | 382 |
| 4-(4-Chloro-phenyl)-piperidine-4-carboxylic acid (7-chloro-1-oxo-1,2-dihydro-isoquinolin-6-yl)-amide | 416 |
| 4-Benzyl-piperidine-4-carboxylic acid (7-chloro-1-oxo-1,2-dihydro-isoquinolin-6-yl)-amide | 396 |
| (R)-Piperidine-3-carboxylic acid (1-oxo-1,2-dihydro-isoquinolin-6-yl)-amide | 272 |
| (S)-Piperidine-3-carboxylic acid (1-oxo-1,2-dihydro-isoquinolin-6-yl)-amide | 272 |
| 1-Methyl-piperidine-4-carboxylic acid (1-oxo-1,2-dihydro-isoquinolin-6-yl)-amide | 286 |
| (R)-N-(7-Chloro-1-oxo-1,2-dihydro-isoquinolin-6-yl)-2-hydroxy-3-methyl-butyramide | 295 |
| Piperazine-2-carboxylic acid (7-chloro-1-oxo-1,2-dihydro-isoquinolin-6-yl)-amide | 307 |
| 4-Methyl-piperidine-4-carboxylic acid (7-chloro-1-oxo-1,2-dihydro-isoquinolin-6-yl)-amide | 320 |
| (3S,4S)-3-Methyl-piperidine-4-carboxylic acid (7-chloro-1-oxo-1,2-dihydro-isoquinolin-6-yl)-amide | 306 |
| (trans)-4-Phenyl-piperidine-3-carboxylic acid (7-chloro-1-oxo-1,2-dihydro-isoquinolin-6-yl)-amide | 382 |
| (1R,3S)-3-Amino-cyclopentanecarboxylicacid (7-chloro-1-oxo-1,2-dihydro-isoquinolin-6-yl)-amide | 306 |
| 4-Hydroxy-cyclohexanecarboxylic acid (7-chloro-1-oxo-1,2-dihydro-isoquinolin-6-yl)-amide | 321 |
| (S)-N-(7-Chloro-1-oxo-1,2-dihydro-isoquinolin-6-yl)-2-cyclohexyl-2-hydroxy-acetamide | 335 |
| (R)-N-(7-Chloro-1-oxo-1,2-dihydro-isoquinolin-6-yl)-2-cyclohexyl-2-hydroxy-acetamide | 335 |
| (S)-N(7-Chloro-1-oxo-1,2-dihydro-isoquinolin-6-yl)-2-hydroxy-2-phenyl-propionamide | 343 |
| (R)-N-(7-Chloro-1-oxo-1,2-dihydro-isoquinolin-6-yl)-2-hydroxy-2-phenyl-propionamide | 343 |
| (1R,3S)-3-Amino-cyclohexanecarboxylic acid (7-chloro-1-oxo-1,2-dihydro-isoquinolin-6-yl)-amide | 320 |
| (1R,3S)-3-Amino-cyclohexanecarboxylic acid (7-methoxy-1-oxo-1,2-dihydro-isoquinolin-6-yl)-amide | 316 |
| (3R,4S)-3-Methyl-piperidine-4-carboxylic acid (7-chloro-1-oxo-1,2-dihydro-isoquinolin-6-yl)-amide | 320 |
| 4-Dimethylamino-cyclohexanecarboxylic acid (7-chloro-1-oxo-1,2-dihydro-isoquinolin-6-yl)-amide | 348 |
| Trans-3-amino-cyclobutanecarboxylic acid (7-chloro-1-oxo-1,2-dihydro-isoquinolin-6-yl)-amide | 292 |
| Cis-3-amino-cyclobutanecarboxylic acid (7-chloro-1-oxo-1,2-dihydro-isoquinolin-6-yl)-amide | 292 |
| 4-Amino-1-(cis-4-chloro-phenyl)-cyclohexanecarboxylic acid (7-chloro-1-oxo-1,2-dihydro-isoquinolin-6-yl)-amide | 430 |

| Name | MH+ |
|---|---|
| 4-Amino-1-(trans-4-chloro-phenyl)-cyclohexanecarboxylic acid (7-chloro-1-oxo-1,2-dihydro-isoquinolin-6-yl)-amide | 430 |
| (S)-N-(7-Chloro-1-oxo-1,2-dihydro-isoquinolin-6-yl)-2-cyclohexyl-2-isopropylamino-acetamide | 391 |
| (S)-N(7-Chloro-1-oxo-1,2-dihydro-isoquinolin-6-yl)-2-cyclohexyl-2-isopropylamino-acetamide | 320 |
| (S)-N-(7-Chloro-1-oxo-1,2-dihydro-isoquinolin-6-yl)-2-cyclohexyl-2-isopropylamino-acetamide | 376 |
| 4-(4-Fluoro-phenyl)-pyrrolidine-3-carboxylic acid (1-oxo-1,2-dihydro-isoquinolin-6-yl)-amide | 352 |
| (1S,2S)-2-Methyl-4-oxo-cyclohexanecarboxylic acid (7-chloro-1-oxo-1,2-dihydro-isoquinolin-6-yl)-amide | 333 |
| 3-Phenyl-pyrrolidine-3-carboxylic acid (7-chloro-1-oxo-1,2-dihydro-isoquinolin-6-yl)-amide | 368 |
| 1-Isopropyl-piperidine-4-carboxylic acid (7-chloro-1-oxo-1,2-dihydro-isoquinolin-6-yl)-amide | 348 |
| 1-Cyclohexyl-piperidine-4-carboxylic acid (7-chloro-1-oxo-1,2-dihydro-isoquinolin-6-yl)-amide | 334 |
| 1-Cyclohexyl-piperidine-4-carboxylic acid (7-chloro-1-oxo-1,2-dihydro-isoquinolin-6-yl)-amide | 388 |
| N-(7-Chloro-1-oxo-1,2-dihydro-isoquinolin-6-yl)-2-mcthyl-4-(piperazine-l-sulfonyl)-benzamidc | 397 |
| N-(7-Chloro-1-oxo-1,2-dihydro-isoquinolin-6-yl)-2-methyl-4-(piperazine-1-sulfonyl)-benzamide | 461 |
| (R)-N (7-Chloro-1-oxo-1,2-dihydro-isoquinolin-6-yl)-2-(2-chloro-phenyl)-2-hydroxy-acetamide | 363 |
| (R)-N-(7-Chloro-1-oxo-1,2-dihydro-isoquinolin-6-yl)-2-(3-chloro-phenyl)-2-hydroxy-acetamide | 363 |
| (2S,3R)-2-Amino-3-methyl-pentanoic acid (7-chloro-1-oxo-1,2-dihydro-isoquinolin-6-yl)-amide | 308 |
| N-(7-Chloro-1-oxo-1,2-dihydro-isoquinolin-6-yl)-2-phenyl-isobutyramide | 341 |
| 1-Benzyl-piperidine-4-carboxylic acid (7-chloro-1-oxo-1,2-dihydro-isoquinolin-6-yl)-amide | 396 |
| (trans)-4-Phenyl-pyrrolidine-3-carboxylic acid (7-chloro-1-oxo-1,2-dihydro-isoquinolin-6-yl)-amide | 368 |
| (trans)-4-(4-Fluoro-phenyl)-pyrrolidine-3-carboxylic acid (7-chloro-1-oxo-1,2-dihydro-isoquinolin-6-yl)-amide | 386 |
| (3R,4S)-1,3-Dimethyl-piperidine-4-carboxylic acid (7-chloro-1-oxo-1,2-dihydro-isoquinolin-6-yl)-amide | 334 |
| 5-Phenyl-piperidine-3-carboxylic acid (7-chloro-1-oxo-1,2-dihydro-isoquinolin-6-yl)-amide | 382 |
| 1,2,3,4-Tetrahydro-isoquinoline-7-carboxylic acid (7-chloro-1-oxo-1,2-dihydro-isoquinolin-6-yl)-amide | 354 |
| 1,2,3,4-Tetrahydro-isoquinoline-6-carboxylic acid (7-chloro-1-oxo-1,2-dihydro-isoquinolin-6-yl)-amide | 354 |
| 4-(3-Amino-propane-1-sulfonyl)-2-chloro-N-(7-chloro-1-oxo-1,2-dihydro-isoquinolin-6-yl)-benzamide | 454 |
| (trans)-4-(3-Bromo-phenyl)-pyrrolidine-3-carboxylic acid (7-chloro-1-oxo-1,2-dihydro-isoquinolin-6-yl)-amide | 447 |
| (trans)-4-(4-Chloro-phenyl)-pyrrolidine-3-carboxylic acid (7-chloro-1-oxo-1,2-dihydro-isoquinolin-6-yl)-amide | 402 |
| (1R,5S,6R)-3-Aza-bicyclo[3.1.0]hexane-6-carboxylic acid (7-chloro-1-oxo-1,2-dihydro-isoquinolin-6-yl)-amide | 304 |
| (1R,5S,6S)-3-Aza-bicyclo[3.1.0]hexane-6-carboxylic acid (7-chloro-1-oxo-1,2-dihydro-isoquinolin-6-yl)-amide | 304 |
| (trans)-4-(3-Bromo-phenyl)-pyrrolidine-3-carboxylic acid (6-chloro-4-oxo-3,4-dihydro-quinazolin-7-yl)-amide | 448 |
| (R)-N-(7-Chloro-1-oxo-1,2-dihydro-isoquinolin-6-yl)-2-(4-chloro-phenyl)-2-hydroxy-propionamide | 377 |
| (R)-N-(6-Chloro-4-oxo-3,4-dihydro-quinazolin-7-yl)-2-(4-chloro-phenyl)-2-hydroxy-propionamide | 378 |
| (R)-2-(4-Chloro-phenyl)-2-hydroxy-N-(4-oxo-3,4-dihydro-quinazolin-7-yl)-propionamide | 344 |
| 1-Methyl-piperidine-4-carboxylic acid (7-bromo-1-oxo-1,2-dihydro-isoquinolin-6-yl)-amide | 365 |
| 1-Methyl-piperidine-4-carboxylic acid (7-fluoro-1-oxo-1,2-dihydro-isoquinolin-6-yl)-amide | 304 |
| 1-Methyl-piperidine-4-carboxylic acid (7-cyano-1-oxo-1,2-dihydro-isoquinolin-6-yl)-amide | 311 |
| (trans)-4-Phenyl-pyrrolidine-3-carboxylic acid (7-bromo-1-oxo-1,2-dihydro-isoquinolin-6-yl)-amide | 413 |
| 4-(4-Chlorophenyl)-pyrrolidine-3-carboxylic acid (7-bromo-1-oxo-1,2-dihydro-isoquinolin-6-yl)-amide | 447 |
| (trans)-4-Phenyl-pyrrolidine-3-carboxylic acid (5-chloro-1-oxo-1,2-dihydro-isoquinolin-6-yl)-amide | 369 |

-continued

| Name | MH+ |
|---|---|
| (trans)-4-Phenyl-pyrrolidine-3-carboxylic acid (7-chloro-5-fluoro-1-oxo-1,2-dihydro-isoquinolin-6-yl)-amide | 386 |

Assessment of Biological Activity

Molecular Assay

The activity of ROCKII (1-543) kinase was measured utilizing Cambrex PKLight ATP Detection Reagent, a homogeneous assay technology using luciferin-luciferase to quantify residual ATP. The assay was performed in 384-well low-volume, white, non-binding surface microtiter plates (Corning). The assay buffer was 25 mM HEPES, pH 7.5, 10 mM $MgCl_2$, 50 mM KCl, 0.2% BSA, 0.01% CHAPS, 100 µM $Na_3VO_4$ and 0.5 mM DTT. Test compounds, dissolved in neat DMSO at 500 µg/mL, were serially diluted for dose response for a final starting concentration of 3 µg/mL in 1% DMSO of assay buffer. ROCKII (1-543) (62,408 Da) was diluted in assay buffer to a final concentration of 7.5 nM in a total volume of 15 µL. Positive controls were reaction mixtures containing no test compound; negative controls (blanks) were reaction mixtures containing no kinase. After 15 minutes of pre-incubation of the test compounds with the kinase, a mixture of ATP and peptide substrate (AKRRRLSSLRA) in assay buffer was added to each well for a final concentration of 750 nM ATP and 500 nM peptide, respectively. After 90 minutes of incubation of the kinase reaction at 28° C. temperature, 10 µL of PKLight ATP Detection Reagent (warmed to room temperature previously) was added to each well. The assay plate was incubated at room temperature for additional 15 minutes and then read on an Analyst in luminescence mode. Dose-response experiments of each test compounds were conducted in quadruplet. $IC_{50}$ values of test compounds represent 50% response of the positive control from the dose-response curve.

Preferred compounds have an $IC_{50}$<1 µM in this assay.

Selected compounds were evaluated in a Rat Aortic Rings tissue assay:

Rat Aortic Rings Tissue Assay

Segments of rat thoracic aorta were dissected from Sprague Dawley rats cleaned of excess connective tissue, and cut into 3-4 mm rings in a petri dish filled with 4° C. PBS, containing 118 mM NaCl; 4.7 mM KCl; 1.6 mM $CaCl_2$; 1.2 mM $KH_2PO_4$; 1.2 mM $MgCl_2$; 10.0 mM Dextrose; 25 mM $NaHCO_3$; 0.02 mM NaEDTA; pH 7.25, and kept on ice before dissection. The rings were then suspended on a force transducer device and placed into 37° C. temperature-controlled tissue baths containing PBS that was constantly oxygenated with 95% $O_2$ and 5% $CO_2$. Isometric force was continually measured and the data collected by a digital acquisition system. The rings were placed under a preload of 2.5 g of force for a 1 hr equilibration period to serve as baseline force. Rings were contracted with 50 mM KCl to obtain the maximum contraction level for normalization. Following a washout period of 30 min, the rings were pre-constricted with $10^{-6}$M phenylephrine and relaxed with a bolus dose of $10^{-7}$M acetylcholine to check the integrity of the endothelium. Following a second washout period of 30 min, rings were pre-constricted a second time with $10^{-6}$M phenylephrine and the contraction allowed to stabilize. A cumulative dose response of a Rho-kinase inhibitor was tested in a DMSO vehicle at a 1:1000 dilution using half log intervals. After each dose of inhibitor the response was allowed to stabilize before the addition of the next dose. Following the cumulative dose response with inhibitor, the tissues were washed 3× in PBS and allowed to equilibrate at resting tension. A second KCl contraction was performed as stated above to check the viability of the tissue. Following this, a second phenylephrine contraction and acetylcholine bolus dose were given as above to cheek for the integrity of the endothelium following inhibitor testing. The effect of the Rho-kinase inhibitors were expressed as a percentage relaxation from the phenylephrine-induced contraction at each dose. The $IC_{50}$ for each inhibitor was determined from the concentration that produced 50% relaxation from the phenylephrine-induced contraction. The data for each inhibitor represents the mean from four different segments from four different rats.

Preferred compounds have an $IC_{50}$<10 µM in this assay.

Methods of Therapeutic Use

In accordance with the invention, there are provided novel methods of using the compounds of the formula (I). The compounds disclosed therein effectively inhibit Rho kinase. The inhibition of Rho kinase is an attractive means for preventing and treating a variety of cardiovascular diseases or conditions associated with Rho kinase activation. Thus, the compounds are useful for the treatment of diseases and conditions as described in the Background section, including the following conditions and diseases; hypertension, atherosclerosis, restenosis, stroke, myocardial infarction, heart failure, coronary artery disease, peripheral artery disease, coronary vasospasm, cerebral vasospasm, ischemia/reperfusion injury, pulmonary hypertension, angina, erectile dysfunction, renal disease and organ failure. As disclosed in the Background section, the compounds of the invention will also be useful for treating diseases or conditions associated with smooth muscle hyper reactivity or with activated Rho-kinase under other pathophysiological conditions. These diseases include but are not limited to asthma, glaucoma, cancer, Alzheimer's disease, multiple sclerosis, spinal cord injury and neuropathic pain.

These disorders have been well characterized in man, but also exist with a similar etiology in other mammals, and can be treated by pharmaceutical compositions of the present invention.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutical acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

The invention claimed is:

1. A compound selected from:
    1-(4-Chloro-phenyl)-cyclopentanecarboxylic acid (4-oxo-3,4-dihydro-quinazolin-7-yl)-amide;
    2-Benzylamino-N-(4-oxo-3,4-dihydro-quinazolin-7-yl)-acetamide;
    1-Benzyl-piperidine-4-carboxylic acid (4-oxo-3,4-dihydro-quinazolin-7-yl)-amide;
    Pyrrolidine-2-carboxylic acid (4-oxo-3,4-dihydro-quinazolin-7-yl)-amide;
    2-Amino-4-methyl-pentanoic acid (4-oxo-3,4-dihydro-quinazolin-7-yl)-amide;
    (R)-2-Amino-N-(4-oxo-3,4-dihydro-quinazolin-7-yl)-3-phenyl-propionamide;
    (S)-2-Amino-N-(4-oxo-3,4-dihydro-quinazolin-7-yl)-3-phenyl-propionamide;
    2-(Cyclohexylmethyl-amino)-N-(4-oxo-3,4-dihydro-quinazolin-7-yl)-acetamide;
    2-Methylamino-N-(4-oxo-3,4-dihydro-quinazolin-7-yl)-2-phenyl-acetamide;
    2-Amino-N-(4-oxo-3,4-dihydro-quinazolin-7-yl)-2-phenyl-acetamide;
    2-Cyclopropylamino-N-(4-oxo-3,4-dihydro-quinazolin-7-yl)-2-phenyl-acetamide;
    (R)-2-Amino-N-(4-oxo-3,4-dihydro-quinazolin-7-yl)-2-phenyl-acetamide;
    (R)-Pyrrolidine-2-carboxylic acid (4-oxo-3,4-dihydro-quinazolin-7-yl)-amide;
    (R)-2-Amino-3-methyl-N-(4-oxo-3,4-dihydro-quinazolin-7-yl)-butyramide;
    2-(Cyclopropylmethyl-amino)-N-(4-oxo-3,4-dihydro-quinazolin-7-yl)-acetamide;
    N-(4-oxo-3,4-dihydro-quinazolin-7-yl)-2-(2-thiophen-2-yl-ethylamino)-acetamide;
    2-(Cyclohexyl-methyl-amino)-N-(4-oxo-3,4-dihydro-quinazolin-7-yl)-acetamide;
    N-(6-Chloro-4-oxo-3,4-dihydro-quinazolin-7-yl)-2-dimethylamino-2-phenyl-acetamide;
    N-(6-Chloro-4-oxo-3,4-dihydro-quinazolin-7-yl)-2-cyclopropylamino-2-phenyl-acetamide;
    2,5-Dimethyl-2H-pyrazole-3-carboxylic acid (4-oxo-3,4-dihydro-quinazolin-7-yl)-amide;
    (trans)-4-(3-Bromo-phenyl)-pyrrolidine-3-carboxylic acid (6-chloro-4-oxo-3,4-dihydro-quinazolin-7-yl)-amide;
    (R)—N-(6-Chloro-4-oxo-3,4-dihydro-quinazolin-7-yl)-2-(4-chloro-phenyl)-2-hydroxy-propionamide;
    (R)-2-(4-Chloro-phenyl)-2-hydroxy-N-(4-oxo-3,4-dihydro-quinazolin-7-yl)-propionamide;
    or a pharmaceutically acceptable salt thereof.

2. A composition comprising the compound of claim 1.

3. A pharmaceutical composition comprising the compound of claim 1 and a pharmaceutically acceptable excipient or carrier.

4. The compound of claim 1, wherein the compound is selected from:
    (R)-2-Amino-N-(4-oxo-3,4-dihydro-quinazolin-7-yl)-3-phenyl-propionamide;
    (S)-2-Amino-N-(4-oxo-3,4-dihydro-quinazolin-7-yl)-3-phenyl-propionamide;
    (R)-2-Amino-N-(4-oxo-3,4-dihydro-quinazolin-7-yl)-2-phenyl-acetamide;
    (R)-Pyrrolidine-2-carboxylic acid (4-oxo-3,4-dihydro-quinazolin-7-yl)-amide;
    (R)-2-Amino-3-methyl-N-(4-oxo-3,4-dihydro-quinazolin-7-yl)-butyramide;
    (trans)-4-(3-Bromo-phenyl)-pyrrolidine-3-carboxylic acid (6-chloro-4-oxo-3,4-dihydro-quinazolin-7-yl)-amide;
    (R)—N-(6-Chloro-4-oxo-3,4-dihydro-quinazolin-7-yl)-2-(4-chloro-phenyl)-2-hydroxy-propionamide;
    (R)-2-(4-Chloro-phenyl)-2-hydroxy-N-(4-oxo-3,4-dihydro-quinazolin-7-yl)-propionamide;
    or a pharmaceutically acceptable salt thereof.

5. The compound of claim 1, wherein the compound is 1-(4-Chloro-phenyl)-cyclopentanecarboxylic acid (4-oxo-3,4-dihydro-quinazolin-7-yl)-amide or a pharmaceutically acceptable salt thereof.

6. The compound of claim 1, wherein the compound is 2-Benzylamino-N-(4-oxo-3,4-dihydro-quinazolin-7-yl)-acetamide or a pharmaceutically acceptable salt thereof.

7. The compound of claim 1, wherein the compound is 1-Benzyl-piperidine-4-carboxylic acid (4-oxo-3,4-dihydro-quinazolin-7-yl)-amide or a pharmaceutically acceptable salt thereof.

8. The compound of claim 1, wherein the compound is Pyrrolidine-2-carboxylic acid (4-oxo-3,4-dihydro-quinazolin-7-yl)-amide or a pharmaceutically acceptable salt thereof.

9. The compound of claim 1, wherein the compound is 2-Amino-4-methyl-pentanoic acid (4-oxo-3,4-dihydro-quinazolin-7-yl)-amide or a pharmaceutically acceptable salt thereof.

10. The compound of claim 1, wherein the compound is 2-(Cyclohexylmethyl-amino)-N-(4-oxo-3,4-dihydro-quinazolin-7-yl)-acetamide or a pharmaceutically acceptable salt thereof.

11. The compound of claim 1, wherein the compound is 2-Methylamino-N-(4-oxo-3,4-dihydro-quinazolin-7-yl)-2-phenyl-acetamide or a pharmaceutically acceptable salt thereof.

12. The compound of claim 1, wherein the compound is 2-Amino-N-(4-oxo-3,4-dihydro-quinazolin-7-yl)-2-phenyl-acetamide or a pharmaceutically acceptable salt thereof.

13. The compound of claim 1, wherein the compound is 2-Cyclopropylamino-N-(4-oxo-3,4-dihydro-quinazolin-7-yl)-2-phenyl-acetamide or a pharmaceutically acceptable salt thereof.

14. The compound of claim 1, wherein the compound is 2-(Cyclopropylmethyl-amino)-N-(4-oxo-3,4-dihydro-quinazolin-7-yl)-acetamide or a pharmaceutically acceptable salt thereof.

15. The compound of claim 1, wherein the compound is N-(4-oxo-3,4-dihydro-quinazolin-7-yl)-2-(2-thiophen-2-yl-ethylamino)-acetamide or a pharmaceutically acceptable salt thereof.

16. The compound of claim 1, wherein the compound is 2-(Cyclohexyl-methyl-amino)-N-(4-oxo-3,4-dihydro-quinazolin-7-yl)-acetamide or a pharmaceutically acceptable salt thereof.

17. The compound of claim 1, wherein the compound is N-(6-Chloro-4-oxo-3,4-dihydro-quinazolin-7-yl)-2-dimethylamino-2-phenyl-acetamide or a pharmaceutically acceptable salt thereof.

18. The compound of claim 1, wherein the compound is N-(6-Chloro-4-oxo-3,4-dihydro-quinazolin-7-yl)-2-cyclopropylamino-2-phenyl-acetamide or a pharmaceutically acceptable salt thereof.

19. The compound of claim 1, wherein the compound is 2,5-Dimethyl-2H-pyrazole-3-carboxylic acid (4-oxo-3,4-dihydro-quinazolin-7-yl)-amide or a pharmaceutically acceptable salt thereof.

* * * * *